(12) United States Patent
Do Couto et al.

(10) Patent No.: US 7,390,635 B2
(45) Date of Patent: Jun. 24, 2008

(54) RECOMBINANT PEPTIDES DERIVED FROM THE MC3 ANTI-BA46 ANTIBODY, METHODS OF USE THEREOF, AND METHODS OF HUMANIZING ANTIBODY PEPTIDES

(75) Inventors: Fernando J. R. Do Couto, Pleasanton, CA (US); Robert L. Ceriani, Lafayette, CA (US); Jerry A. Peterson, San Francisco, CA (US)

(73) Assignee: Cancer Research Institute of Contra Costa, San Francisco, CA (US)

( * ) Notice: Subject to any disclaimer, the term of this patent is extended or adjusted under 35 U.S.C. 154(b) by 65 days.

(21) Appl. No.: 10/965,616

(22) Filed: Oct. 13, 2004

(65) Prior Publication Data

US 2005/0169915 A1    Aug. 4, 2005

Related U.S. Application Data

(63) Continuation of application No. 09/956,206, filed on Sep. 17, 2001, now abandoned, which is a continuation of application No. 08/525,539, filed as application No. PCT/US95/11683 on Sep. 14, 1995, now Pat. No. 6,309,636, and a continuation-in-part of application No. 08/487,598, filed on Jun. 7, 1995, now abandoned, which is a continuation-in-part of application No. 08/307,868, filed on Sep. 16, 1994, now abandoned.

(51) Int. Cl.
    *C12N 15/00* (2006.01)
(52) U.S. Cl. ............... 435/69.1; 530/387.3; 530/388.15; 530/387.1; 424/130.1; 424/141.1
(58) Field of Classification Search ................ 435/69.1; 530/387.3, 388.15, 387.1; 424/130.1, 141.1
    See application file for complete search history.

(56) References Cited

U.S. PATENT DOCUMENTS

| 5,618,920 A | * | 4/1997 | Robinson et al. | .......... | 530/387.1 |
| 5,639,641 A | * | 6/1997 | Pedersen et al. | .......... | 530/387.3 |
| 5,693,762 A | * | 12/1997 | Queen et al. | ............. | 530/387.3 |
| 5,766,571 A | * | 6/1998 | Ceriani et al. | .............. | 424/1.49 |

FOREIGN PATENT DOCUMENTS

| EP | 592106 | * | 4/1994 |
| WO | WO 90/07861 | * | 7/1990 |
| WO | WO 93/11794 | * | 6/1993 |

OTHER PUBLICATIONS

Eduardo A. Padlan (1991. Molecular Immunology, 28:489-498).*

* cited by examiner

*Primary Examiner*—David J. Blanchard
*Assistant Examiner*—Parithosh K. Tungaturthi
(74) *Attorney, Agent, or Firm*—DLA Piper US LLP

(57) ABSTRACT

The present invention provides recombinant peptides that specifically and selectively bind to the human milk fat globule (HMFG) antigen, BA46. In particular, the present invention provides recombinant variants of the Mc3 antibody, including humanized versions of Mc3. The variant Mc3 peptides are particularly useful for diagnostic, prognostic, and therapeutic applications in the field of breast cancer.

The present invention also provides methods for the humanization of antibodies such as murine monoclonal antibodies. The novel humanization methods are applied to the production of humanized Mc3 antibodies and it is shown that these humanized antibodies retain the ability to engage in high affinity binding to their cognate antigen. Such humanization enables the use of these antibodies for immunodiagnostic and immunotherapeutic applications in humans.

5 Claims, 30 Drawing Sheets

FIGURE 1

Fab STRUCTURES FOR WHICH COORDINATES ARE IN THE PROTEIN DATA BANK

| | ANTIBODY | RESOLUTION (A) | R-VALUE | PDB CODE |
|---|---|---|---|---|
| HUMAN: | NEWM | 2.0 | 0.46 | 3FAB |
| | KOL | 1.9 | 0.189 | 2FB4 |
| MURINE: | McPC603 | 2.7 | 0.225 | 1MCP |
| | J539 | 1.95 | 0.194 | 2FBJ |
| | HyHEL-5 | 2.54 | 0.245 | 2HFL |
| | HyHEL-10 | 3.0 | 0.24 | 3HFM |
| | R19.9 | 2.8 | 0.30 | 1F19 |
| | 4-4-20 | 2.7 | 0.215 | 4FAB |
| | 36-71 | 1.85 | 0.248 | 6FAB |
| | B1312 | 2.8 | 0.197 | 1IGF |
| | D1.3 | 2.5 | 0.184 | 1FDL |

FIGURE 2

$V_L$ FRAMEWORK RESIDUES THAT CONTACT CDR RESIDUES IN Fabs OF KNOWN THREE-DIMENSIONAL STRUCTURE

| POSITION | J539 | McPC603 | HyHEL-10 | HyHEL-5 | R19.9 | 4-4-20 | 36-71 | B1312 | D1.3 | NEWM | KOL |
|---|---|---|---|---|---|---|---|---|---|---|---|
| 1 | GLU(2) | ASP(5) | ASP(10) | ASP(3) | | ASP(8) | ASP(4) | | ASP(11) | | |
| 2 | ILE(11) | ILE(15) | ILE(17) | ILE(13) | ILE(5) | VAL(9) | ILE(20) | VAL(9) | ILE(10) | SER(3) | |
| 3 | VAL(3) | | VAL(2) | VAL(3) | GLN(2) | VAL(2) | GLN(2) | LEU(6) | | VAL(2) | |
| 4 | LEU(7) | MET(6) | LEU(6) | LEU(10) | MET(9) | MET(13) | MET(7) | MET(6) | MET(7) | LEU(4) | LEU(6) |
| 5 | | THR(1) | | | THR(1) | THR(2) | | | | THR(1) | |
| 7 | | | | | | | | THR(4) | | | |
| 22 | | | | | | | | SER(6) | | | |
| 23 | CYS(1) | CYS(1) | CYS(2) | CYS(2) | CYS(1) | CYS(1) | CYS(1) | | | | CYS(1) |
| 35 | TRP(3) | TRP(2) | TRP(4) | | TRP(2) | | TRP(6) | TRP(4) | TRP(4) | TRP(1) | TRP(2) |
| 36 | TYR(12) | TYR(16) | TYR(8) | TYR(10) | TYR(22) | TYR(13) | TYR(15) | TYR(8) | TYR(14) | TYR(13) | TYR(11) |
| 45 | | | | | LYS(12) | LYS(5) | | | | | |
| 46 | PRO(3) | LEU(6) | LEU(4) | ARG(15) | LEU(5) | VAL(14) | LEU(5) | LEU(10) | LEU(6) | LEU(2) | LEU(6) |
| 48 | ILE(1) | ILE(1) | ILE(1) | | | | ILE(3) | ILE(2) | VAL(1) | | ILE(1) |
| 49 | TYR(28) | TYR(29) | LYS(13) | TYR(12) | TYR(40) | TYR(22) | TYR(22) | TYR(16) | TYR(25) | | TYR(25) |
| 58 | VAL(3) | VAL(3) | ILE(1) | VAL(6) | VAL(5) | VAL(5) | VAL(4) | VAL(5) | VAL(1) | | VAL(6) |
| 60 | ASP(1) | | | | | ASP(2) | | ASP(4) | | | ASP(2) |
| 62 | | | | PHE(1) | | PHE(1) | PHE(1) | | | | |
| 66 | | | | | | | | | | LYS(2) | LYS(11) |
| 67 | SER(3) | | | | | | | | SER(1) | | |
| 69 | THR(3) | THR(3) | | | | THR(5) | THR(1) | THR(4) | THR(1) | SER(1) | |
| 70 | ASP(2) | | | | ASP(1) | | ASP(6) | | | SER(2) | |
| 71 | TYR(14) | PHE(23) | PHE(17) | TYR(17) | TYR(24) | PHE(17) | TYR(17) | PHE(19) | TYR(16) | ALA(3) | ALA(4) |
| 88 | CYS(1) | CYS(2) | | CYS(1) | CYS(1) | CYS(1) | CYS(1) | CYS(1) | CYS(2) | | CYS(1) |
| 98 | PHE(8) | PHE(8) | PHE(10) | PHE(5) | PHE(8) | PHE(4) | PHE(8) | PHE(14) | PHE(14) | PHE(3) | PHE(7) |

FIGURE 3

V_H FRAMEWORK RESIDUES THAT CONTACT CDR RESIDUES IN Fabs OF KNOWN THREE-DIMENSIONAL STRUCTURE

| POSITION | J539 | McPC603 | HyHEL-10 | HyHEL-5 | R19.9 | 4-4-20 | 36-71 | B13I2 | D1.3 | NEWM | KOL |
|---|---|---|---|---|---|---|---|---|---|---|---|
| 1 | VAL(11) | VAL(3) | VAL(8) | | | | GLU(3) | | | | |
| 2 | LEU(2) | LEU(5) | LEU(5) | | VAL(1) | | VAL(7) | VAL(3) | VAL(12) | | VAL(9) |
| 4 | | THR(2) | VAL(6) | | LEU(2) | LEU(1) | LEU(1) | LEU(1) | LEU(1) | | LEU(1) |
| 24 | | | | | | ALA(1) | | | | | |
| 27 | PHE(3) | PHE(2) | | TYR(14) | TYR(11) | PHE(26) | TYR(4) | PHE(4) | PHE(4) | THR(1) | PHE(3) |
| 28 | ASP(9) | THR(5) | | THR(3) | THR(6) | THR(4) | THR(2) | THR(3) | | SER(1) | ILE(2) |
| 29 | PHE(4) | PHE(4) | | PHE(10) | PHE(7) | PHE(13) | PHE(6) | PHE(3) | | | PHE(4) |
| 30 | | | THR(2) | | THR(6) | SER(7) | | | | ASP(6) | |
| 36 | | | | | | | TRP(2) | | | | |
| 37 | | VAL(1) | | | VAL(1) | | | | | | |
| 38 | ARG(1) | ARG(2) | ARG(4) | LYS(2) | LYS(1) | ARG(4) | LYS(2) | ARG(1) | VAL(1) | VAL(2) | ARG(3) |
| 40 | | | | ARG(1) | | | | | | | |
| 46 | GLU(3) | GLU(4) | GLU(1) | GLU(27) | GLU(3) | GLU(4) | GLU(9) | | GLU(1) | | GLU(1) |
| 47 | TRP(21) | TRP(29) | TYR(20) | TRP(21) | TRP(13) | TRP(18) | TRP(21) | TRP(23) | TRP(19) | TRP(22) | TRP(15) |
| 48 | ILE(1) | ILE(1) | MET(6) | ILE(12) | ILE(13) | VAL(1) | ILE(9) | VAL(3) | LEU(1) | ILE(2) | VAL(1) |
| 49 | | ALA(2) | | | | ALA(2) | | ALA(2) | | | ALA(2) |
| 66 | | ARG(11) | | | | ARG(3) | | ARG(2) | | ARG(2) | ARG(1) |
| 67 | PHE(4) | PHE(10) | ILE(9) | ALA(1) | | PHE(11) | THR(5) | PHE(12) | LEU(6) | VAL(2) | PHE(10) |
| 68 | | ILE(1) | | | THR(1) | THR(11) | | | | | THR(2) |
| 69 | ILE(8) | VAL(6) | ILE(8) | PHE(12) | LEU(5) | ILE(20) | LEU(6) | ILE(11) | ILE(8) | MET(4) | ILE(9) |
| 71 | ARG(7) | ARG(16) | ARG(2) | ALA(1) | VAL(4) | ARG(6) | VAL(6) | ARG(3) | LYS(4) | | ARG(9) |
| 73 | ASN(1) | THR(3) | | | | ASP(3) | | | | | |
| 78 | LEU(4) | LEU(7) | TYR(9) | ALA(1) | ALA(1) | VAL(2) | ALA(1) | LEU(6) | VAL(4) | PHE(5) | LEU(5) |
| 80 | | | | | | LEU(1) | | | | | |
| 82 | | | LEU(2) | | | | | | MET(1) | LEU(1) | |
| 86 | | | | | | ASP(2) | | | | | |
| 92 | | | CYS(1) | | | | | CYS(1) | CYS(1) | | |
| 93 | ALA(4) | ALA(5) | LEU(2) | | | THR(3) | CYS(1) | THR(5) | ALA(4) | ALA(1) | ALA(3) |
| 94 | ARG(38) | ARG(24) | ASN(11) | HIS(2) | ARG(30) | | ALA(1) | ARG(14) | ARG(30) | ARG(22) | ARG(27) |
| 103 | TRP(5) | TRP(9) | | | TRP(2) | TRP(2) | ARG(23) | | TRP(2) | TRP(4) | TRP(4) |
| | | | | | | | TRP(5) | | | | |

FIGURE 4

FRAMEWORK RESIDUES THAT CONTACT FRAMEWORK RESIDUES IN THE OPPOSITE DOMAIN IN Fabs OF KNOWN THREE-DIMENSIONAL STRUCTURE

IN $V_L$:

| POSITION | J539 | McPC603 | HyHEL-10 | HyHEL-5 | R19.9 | 4-4-20 | 36-71 | B1312 | D1.3 | NEWM | KOL |
|---|---|---|---|---|---|---|---|---|---|---|---|
| 36 | TYR(3) | TYR(4) | TYR(3) | TYR(5) | | TYR(11) | TYR(7) | TYR(1) | TYR(7) | | TYR(5) |
| 38 | GLN(10) | GLN(4) | GLN(9) | GLN(5) | GLN(5) | GLN(3) | GLN(6) | GLN(12) | GLN(6) | | GLN(8) |
| 43 | SER(7) | PRO(1) | SER(8) | SER(5) | THR(3) | | | SER(3) | SER(2) | | ALA(1) |
| 44 | PRO(10) | PRO(14) | PRO(8) | PRO(11) | | PRO(7) | ILE(20) | PRO(16) | PRO(16) | PRO(7) | PRO(13) |
| 46 | PRO(3) | | | | | | | | | | |
| 85 | | MET(2) | | | THR(5) | | | VAL(1) | | ASP(12) | |
| 87 | TYR(6) | PHE(6) | TYR(4) | TYR(2) | | | PHE(5) | TYR(10) | TYR(8) | TYR(6) | TYR(6) |
| 98 | PHE(11) | PHE(8) | PHE(7) | PHE(12) | PHE(12) | PHE(8) | PHE(13) | PHE(12) | PHE(10) | PHE(15) |
| 100 | | ALA(2) | | | | | | | | | |

IN $V_H$:

| POSITION | J539 | McPC603 | HyHEL-10 | HyHEL-5 | R19.9 | 4-4-20 | 36-71 | B1312 | D1.3 | NEWM | KOL |
|---|---|---|---|---|---|---|---|---|---|---|---|
| 37 | VAL(4) | | ILE(2) | VAL(1) | VAL(4) | VAL(2) | VAL(1) | VAL(2) | VAL(4) | VAL(1) | VAL(4) |
| 39 | GLN(10) | GLN(4) | LYS(8) | GLN(5) | GLN(5) | GLN(3) | GLN(6) | GLN(10) | GLN(6) | GLN(4) | GLN(7) |
| 43 | | ARG(2) | ASN(4) | GLN(7) | | | | LYS(6) | | ARG(19) | |
| 44 | | | | | | | | | | | |
| 45 | LEU(13) | LEU(12) | LEU(8) | LEU(14) | | LEU(8) | | LEU(13) | LEU(11) | LEU(11) | LEU(16) |
| 47 | TRP(1) | | TYR(2) | | TRP(2) | | | | TRP(3) | TRP(2) | |
| 91 | TYR(6) | TYR(4) | TYR(3) | TYR(8) | PHE(3) | TYR(2) | PHE(4) | TYR(3) | TYR(5) | TYR(3) | |
| 103 | TRP(11) | TRP(15) | TRP(16) | TRP(11) | TRP(4) | TRP(18) | TRP(24) | TRP(22) | TRP(19) | TRP(8) | TRP(19) |
| 105 | GLN(5) | | | | | | | | | | |

FIGURE 5

INWARD-POINTING, BURIED FRAMEWORK RESIDUES IN THE $V_L$ OF Fabs OF KNOWN THREE-DIMENSIONAL STRUCTURE

| POSITION | J539 | McPC603 | HyHEL-10 | HyHEL-5 | R19.9 | 4-4-20 | 36-71 | B1312 | D1.3 | NEWM | KOL |
|---|---|---|---|---|---|---|---|---|---|---|---|
| 2 | ILE | ILE | ILE | ILE | ILE | VAL | ILE | VAL | ILE | LEU | LEU |
| 4 | LEU | MET | LEU | LEU | MET | MET | MET | MET | MET | GLN | GLN |
| 6 | GLN | GLN | GLN | GLN | GLN | GLN | GLN | GLN | GLN | VAL | ALA |
| 11 | THR | LEU | MET | LEU | LEU | LEU | LEU | LEU | LEU | | |
| 13 | ALA | VAL | ALA | ALA | ALA | VAL | ALA | VAL | ALA | | |
| 19 | VAL | VAL | VAL | VAL | VAL | VAL | VAL | VAL | VAL | VAL | VAL |
| 21 | ILE | MET | LEU | MET | ILE | ILE | ILE | ILE | ILE | ILE | ILE |
| 23 | CYS | CYS | CYS | CYS | CYS | CYS | CYS | CYS | CYS | CYS | CYS |
| 35 | TRP | TRP | TRP | TRP | TRP | TRP | TRP | TRP | TRP | TRP | TRP |
| 37 | GLN | GLN | GLN | GLN | GLN | GLN | GLN | GLN | GLN | GLN | GLN |
| 47 | TRP | LEU | LEU | TRP | LEU | LEU | LEU | LEU | LEU | LEU | LEU |
| 48 | ILE | ILE | ILE | ILE | VAL | ILE | ILE | ILE | VAL | | ILE |
| 49 | | | | | | | | | | PHE | |
| 58 | VAL | VAL | ILE | VAL | VAL | VAL | VAL | VAL | VAL | | VAL |
| 61 | ARG | ARG | ARG | ARG | ARG | ARG | ARG | ARG | ARG | | ARG |
| 62 | PHE | PHE | PHE | PHE | PHE | PHE | PHE | PHE | PHE | PHE | PHE |
| 71 | TYR | PHE | PHE | TYR | TYR | PHE | TYR | PHE | TYR | ALA | ALA |
| 73 | LEU | LEU | LEU | LEU | LEU | LEU | LEU | LEU | LEU | LEU | LEU |
| 75 | ILE | ILE | ILE | ILE | ILE | ILE | ILE | ILE | ILE | ILE | ILE |
| 78 | MET | VAL | VAL | MET | LEU | VAL | LEU | VAL | LEU | LEU | LEU |
| 82 | ASP | ASP | ASP | ASP | ASP | ASP | ASP | ASP | ASP | ASP | ASP |
| 83 | | | | | | | | | PHE | | |
| 84 | ALA | ALA | | ALA | ALA | | ALA | | | ALA | THR |
| 86 | TYR | TYR | TYR | TYR | TYR | TYR | TYR | TYR | TYR | TYR | TYR |
| 88 | CYS | CYS | CYS | CYS | CYS | CYS | CYS | CYS | CYS | CYS | CYS |
| 102 | THR | THR | THR | THR | THR | THR | THR | THR | THR | THR | THR |
| 104 | LEU | LEU | LEU | LEU | LEU | LEU | LEU | LEU | LEU | LEU | LEU |
| 106 | LEU | ILE | ILE | ILE | LEU | LEU | ILE | ILE | | VAL | VAL |

FIGURE 6

INWARD-POINTING BURIED FRAMEWORK RESIDUES IN THE $V_H$ OF Fabs OF KNOWN THREE-DIMENSIONAL STRUCTURE

| POSITION | J539 | McPC603 | HyHEL-10 | HyHEL-5 | R19.9 | 4-4-20 | 36-71 | B1312 | D1.3 | NEWM | KOL |
|---|---|---|---|---|---|---|---|---|---|---|---|
| 2 | VAL | VAL | VAL | | | | VAL | VAL | VAL | | VAL |
| 4 | LEU | LEU | LEU | LEU | LEU | LEU | LEU | LEU | LEU | LEU | LEU |
| 6 | GLU | GLU | GLU | GLN | GLU | GLU | GLN | GLU | GLU | GLN | GLN |
| 9 | | | PRO | | | | | | | | |
| 12 | VAL | VAL | VAL | MET | VAL | VAL | VAL | VAL | VAL | VAL | VAL |
| 18 | LEU | LEU | LEU | VAL | VAL | MET | VAL | LEU | LEU | LEU | LEU |
| 20 | LEU | LEU | LEU | ILE | MET | LEU | MET | LEU | ILE | LEU | LEU |
| 22 | CYS | CYS | CYS | CYS | CYS | CYS | CYS | CYS | CYS | CYS | CYS |
| 24 | ALA | THR | VAL | ALA | ALA | ALA | ALA | ALA | VAL | VAL | SER |
| 27 | PHE | PHE | ASP | TYR | TYR | PHE | TYR | PHE | PHE | THR | PHE |
| 29 | PHE | PHE | ILE | PHE | PHE | PHE | PHE | PHE | LEU | PHE | PHE |
| 36 | TRP | TRP | TRP | TRP | TRP | TRP | TRP | TRP | TRP | TRP | TRP |
| 38 | ARG | ARG | ARG | LYS | LYS | ARG | LYS | ARG | ARG | ARG | ARG |
| 40 | | | | | | SER | | | | | |
| 46 | | GLU | GLU | GLU | | | | | | | |
| 48 | ILE | ILE | MET | ILE | ILE | VAL | ILE | VAL | LEU | ILE | VAL |
| 49 | | ALA | | | | ALA | | ALA | | | ALA |
| 66 | LYS | ARG | ARG | LYS | THR | PHE | THR | ARG | ARG | ARG | ARG |
| 67 | PHE | PHE | ILE | ALA | LEU | ILE | LEU | PHE | LEU | VAL | PHE |
| 69 | ILE | VAL | ILE | PHE | VAL | ARG | VAL | ILE | ILE | MET | ILE |
| 71 | ARG | ARG | ARG | ALA | | SER | | ARG | LYS | VAL | ARG |
| 76 | | | | | | | | | | | |
| 78 | LEU | LEU | TYR | ALA | ALA | VAL | ALA | LEU | VAL | PHE | LEU |
| 80 | LEU | LEU | LEU | MET | MET | LEU | MET | LEU | LEU | LEU | LEU |
| 82 | MET | MET | LEU | LEU | LEU | MET | LEU | MET | MET | LEU | MET |
| 82C | VAL | LEU | VAL | LEU | LEU | LEU | LEU | LEU | LEU | VAL | LEU |
| 86 | ASP | ASP | ASP | ASP | ASP | ASP | ASP | ASP | ASP | ASP | ASP |
| 88 | ALA | ALA | ALA | ALA | ALA | ALA | ALA | ALA | ALA | ALA | |
| 90 | TYR | TYR | TYR | TYR | TYR | TYR | TYR | TYR | TYR | TYR | |
| 92 | CYS | CYS | CYS | CYS | CYS | CYS | CYS | CYS | CYS | CYS | CYS |
| 94 | ARG | ARG | ASN | HIS | ARG | ARG | ARG | ARG | ARG | ARG | ARG |
| 107 | THR | THR | | THR | THR | THR | THR | THR | THR | SER | THR |
| 109 | VAL | VAL | VAL | LEU | LEU | VAL | LEU | LEU | LEU | VAL | VAL |
| 111 | VAL | VAL | VAL | VAL | VAL | VAL | VAL | VAL | VAL | VAL | VAL |

FIGURE 7

HUMAN ANTIBODIES THAT ARE MOST SIMILAR IN SEQUENCE TO MURINE ANTIBODIES
OF KNOWN THREE-DIMENSIONAL STRUCTURE

| ANTIBODY DOMAIN | MOST SIMILAR HUMAN SEQUENCE |
|---|---|
| HyHEL-10 | |
| VH | 58P2'CL (77/112) |
| VH FRAMEWORK | 15P1'CL, ML1'CL (62/87) |
| VH IMPT | 58P2'CL, Ab26'CL, C6B2'CL (28/38) |
| VL | IARC/BL41'CL (73/107) |
| VL FRAMEWORK | IARC/BL41'CL (59/80) |
| VL IMPT | IARC/BL41'CL (30/37) |
| HyHEL-5 | |
| VH | ND'CL (74/116) |
| VH FRAMEWORK | 783c'CL, X17115'CL (63/87) |
| VH IMPT | 21/28'CL, 51P1'CL, 783c'CL, 8E10'CL, AND, KAS, NEI'CL, X17115'CL (25/37) |
| VL | HF2-1/17'CL, KAS (65/105) |
| VL FRAMEWORK | HF2-1/17'CL (57/80) |
| VL IMPT | BI, DEN, HF2-1/17'CL, KUE, REI, WALKER'CL, WIL(-) (27/36) |
| R19.9 | |
| VH | 21/28'CL (73/119) |
| VH FRAMEWORK | 21/28'CL, 51P1'CL, AND, LS2'CL, NEI'CL (60/87) |
| VH IMPT | 21/28'CL, 8E10'CL, LS2'CL (28/38) |
| VL | WALKER'CL (78/107) |
| VL FRAMEWORK | RZ (62/80) |
| VL IMPT | REI, WALKER'CL (33/36) |

FIGURE 7A

| | | |
|---|---|---|
| 4-4-20 | VH | 30P1'CL (77/116) |
| | VH FRAMEWORK | 2P1'CL, 3D6'CL (65/87) |
| | VH IMPT | 4B4'CL, M26'CL (36/41) |
| | VL | RPM1-6410'CL (91/112) |
| | VL FRAMEWORK | GM-607-'CL (68/80) |
| | VL IMPT | CUM, FR, NIM (33/36) |
| J539 | VH | 30P1'CL, Vh38C1.10'CL (81/118) |
| | VH FRAMEWORK | 10/2'CL, 30P1'CL, M43 (71/87) |
| | VH IMPT | 38P1'CL, 56P1'CL, M72, M74 (36/40) |
| | VL | PA (62/105) |
| | VL FRAMEWORK | LEN, MEA (53/80) |
| | VL IMPT | BI, DEN, KUE, REI, WALKER'CL, WIL(-) (26/35) |
| McPC603 | VH | M72 (81/120) |
| | VH FRAMEWORK | 4G12'CL, Ab18'CL, M72 (70/87) |
| | VH IMPT | 56P1'CL, M72, M74, RF-SJ2'CL (36/42) |
| | VL | FK-001'CL, LEN (91/113) |
| | VL FRAMEWORK | LEN (70/80) |
| | VL IMPT | LEN (38/42) |
| 36-71 | VH | 21/28'CL (74/119) |
| | VH FRAMEWORK | 21/28'CL, 51P1'CL, 783c'CL, AND'CL, NEI'CL, X17115'CL (61/87) |
| | VH IMPT | 21/28'CL, 8E10'CL (28/38) |
| | VL | AG (76/105) |
| | VL FRAMEWORK | R2 (63/80) |
| | VL IMPT | REI, RZ, WALKER'CL (34/37) |

FIGURE 7B

B13I2
VH
VH FRAMEWORK    56P1'CL (83/119)
                4B4'CL, 4G12'CL, M26'CL, M72, RF-SJ2'CL, Vh38C1.10'CL (68/87)
VH IMPT         56P1'CL, M72, M74, RF-SJ2'CL (37/39)

VL
VL FRAMEWORK    RPM1-6410'CL (86/112)
                GM-607-'CL (69/80)
VL IMPT         CUM, NIM (36/39)

D1.3
VH
VH FRAMEWORK    C6B2'CL (72/116)
                C6B2'CL (62/87)
VH IMPT         M60'CL (32/37)

VL
VL FRAMEWORK    BR (75/107)
                HF2-1/17'CL (64/80)
VL IMPT         3D6'CL, BI, DEN, EU, KUE, PA, REI, WALKER'CL, WIL(-) (32/36)

FIGURE 8

|  | | | CDR1 | |
|---|---|---|---|---|
| J539 | EI.L.Q... | ...T.A... | ...V.I.C | sas------svsslh WYQQ....SP.PWIY |
| McPC603 | DIVMTQ... | ...L.V... | ...V.M.C | ksqslnsgnknfls WYQQ....PP.LLIY |
| HyHEL-10 | DIVL.Q... | ...L.V... | ...V.L.C | rasq------signnlh WYQQ....SP.LLIK |
| HyHEL-5 | DIVL.Q... | ...M.A... | ...V.M.C | sas------svnymy WYQQ....SP.RWIY |
| R19.9 | .IQMTQ... | ...L.A... | ...V.I.C | rasq------dissyln WYQQ....T.KLLVY |
| 4-4-20 | DVVMTQ... | ...L.V... | ...A.I.C | rasq-slvhsgngntylr WYLQ.....PKVLIY |
| 36-71 | DIQM.Q... | ...L.A... | ...V.I.C | rasq------dinnfln WYQQ.....I.LLIY |
| B1312 | .VLM.QT... | ...L.V... | ...A.ISC | rsnq-tilsdgdtyls WYLQ....SP.LLIY |
| D1.3 | DI.M.Q... | ...L.A... | ...V.I.C | rasg------alhayls WYQQ....SP.LLVY |

|  | CDR2 | | | | CDR3 | |
|---|---|---|---|---|---|---|
| J539 | eisklas | .V..RF... | ......Y.L.I..M...D.A.YYC | qgwtyplit | F...T.L.L. |
| McPC603 | gastres | .V.DRF... | ....S.TDF.L.I..V...D.A.YYC | qndhsyplt | F.A.T.L.I. |
| HyHEL-10 | yasqsis | .I..RF... | ......T.F.L.I..V...D..MYFC | qqsnswpyt | F...T.L.I. |
| HyHEL-5 | dtsklas | .V..RF... | ......Y.L.I..M...D.A.YYC | qqwgr-npt | F...T.L.I. |
| R19.9 | ytsrlhs | .V..RF... | ......DY.L.I..L...D.ATY.C | qggsttprt | F...T.L... |
| 4-4-20 | kvsnrfs | .V.DRF... | ......T.F.L.I..V...D...Y.C | sqsthvpwt | F...T.L... |
| 36-71 | ftsrsqs | .V..RF... | ......TDY.L.I..L...D.A.YFC | qqgnalprt | F...T.L.I. |
| B1312 | kvsnrfs | .V.DRF... | ......T.F.L.I..V...D..VYYC | fggshvppt | F...T.L.I. |
| D1.3 | ytttlad | .V..RF... | ....S.T.Y.L.I..L...DF..YYC | qhfwstprt | F...T.L... |

FIGURE 9

Framework Residues In V$_H$ That Probably Need
To Be Preserved In Order To Reproduce The
Ligand Binding Properties Of The Original
Antibody

```
                                          CDR1
J539         .V.L.E.....V.....L.L.C.A..FDF. kywms WVRQ.....LEWI.
McPC603      .V.L.E.....V.....L.L.C.T..FTF. dfyme WVRQ....RLEWIA
HyHEL-10     .V.L.E...P..V.....L.L.C.V..D.IT sdyws WIRK...N.LEYM.
HyHEL-5      ...L.Q.....M.....V.I.C.A..YTF. dywie WVKQR....LEWI.
R19.9        .V.L.E.....V.....V.M.C.A..YTFT sygvn WVKQ...Q..EWI.
4-4-20       ...L.E.....V.....M.L.C.A..FTFS dywmn WVRQS....LEWVA
36-71        EV.L.Q.....V.....V.M.C.A..YTF. sngin WVKQ.....LEWI.
B1312        .V.L.E.....V.....L.L.C.A..FTF. rcams WVRQ...K.L.WVA
D1.3         .V.L.E.....V.....L.I.C.V..F.L. gygvn WVRQ.....LEWL.

CDR2
J539         eihp--dsgtinytpslkd KF.I.R.N....L.L.M..V...D.A.YYCAR
McPC603      asrnkgnkytteysasvkg RFIV.R.T....L.L.M..L...D.A.YYCAR
HyHEL-10     yvs---ysgstyynpslks RI.I.R......Y.L.L..V...D.A.YYC.N
HyHEL-5      eilp--gsgstnyherfkg KA.F.A......A.M.L..L...D...YYCLH
R19.9        yinp--gkgylaynekfkg .TTL.V......A.M.L..L...D.A.YFC.R
4-4-20       qirnkpynyetyysdsvkg RFTI.R.D..S.V.L.M..L...D...YYCT.
36-71        ynnp--gngyiaynekfkg .T.L.V......A.M.L..L...D.A.YFCAR
B1312        giss--ggsytfypdtvkg RF.I.R......L.L.M..L...D.A.YYCTR
D1.3         miw---gdgntdynsalks RL.I.K......V.L.M..L...D.A.YYCAR CDR3
J539         lhyygyn------ay W.Q.T.V.V..
McPC603      nyygstwyf----dv W...T.V.V..
HyHEL-10     wdg----------dy W.....V.V..
HyHEL-5      gnydf--------dg W...T.L.V..
R19.9        sfyggsdlavyyfds W...T.L.V..
4-4-20       syygm--------dy W...T.V.V..
36-71        seyyggsykf---dy W...T.L.V..
B1312        yssdpfyf-----dy W...T.L.V..
D1.3         erdyrl-------dy W...T.L.V..
```

Figure 10: MuMc3 $V_H$

```
atg aaa tgc agc tgg gtc att ctc ttc CTC CTG TCA GGA ACT GCA GGT GTC CAC
 m   k   c   s   w   v   i   l   f   L   L   S   G   T   A   G   V   H TCT GAG GTC CAG CTG CAA CAG TCT GGA CCT GAG CTG GTG AAG CCT GGA GCT TCA
 S   E   V   Q   L   Q   Q   S   G   P   E   L   V   K   P   G   A   S ATG AAG ATA TCC TGC AAG GCT TCT GGT TAC TCA TTC ACT GGC TAT ACC ATG CAC
 M   K   I   S   C   E   A   S   G   Y   S   F   T   G   Y   T   M   H TGG GTG AAG CAG AGC CAT GGA ATG AAC CTT GAG TGG ATT GGA CTT ATT AAT CCT
 W   V   K   Q   S   H   G   M   N   L   E   W   I   G   L   I   N   P TAC AAT GGT GGT ACT GTC TAC AAC CAG AAG TTC CAG GAC AAG GCC ACA TTA ACT
 Y   N   G   G   T   V   Y   N   Q   K   F   Q   D   K   A   T   L   T GTA GAC AAG TCA TCC GGC ACA GCC TAC ATG GAG CTC CTC AGT CTG ACA TCT GAG
 V   D   K   S   S   G   T   A   Y   M   E   L   L   S   L   T   S   E GAC TCT GCA GTC TAT TTC TGT GCA AGA CGT TGG AGA TAT ACT ATG GAC TAT TGG
 D   S   A   V   Y   F   C   A   R   R   W   R   Y   T   M   D   Y   W GGT CAA GGA ACC TCA GTC ACC GTC TCC TCA G
 G   Q   G   T   S   V   T   V   S   S
```

Figure 11: MuMc3 $V_\kappa$

```
atg gag ttc cag acc cag gtC TTT GTA TTC GTG TTT CTC TGG TTG TCT GGT GTT
 m   e   f   q   t   q   v   f   v   f   v   f   L   W   L   S   G   V GAC GGA GAC ATT GTG ATG ACC CAG TCT CAC AAA TTC ATG TCC ACA TCA GAG GGA
 d   g   D   I   V   M   T   Q   S   H   K   F   M   S   T   S   E   G GAC TGG GTC AGC ATC ACC TGC AAG GCC AGT CAG GAT GTG AGT ATT GGT GTA GCC
 D   W   V   S   I   T   C   K   A   S   Q   D   V   S   I   G   V   A TGG TAT CAA CAG AAA CCA GGA CAA TCT CCT AAA CTG CTG ATT TAC TCG GCA TCC
 W   Y   Q   Q   K   P   G   Q   S   P   K   L   L   I   Y   S   A   S TCC CGG TAC ACT GGA GTC CCT GAT CGC TTC AGT GGC AGT GGA TCT GGG ACG GAT
 S   R   Y   T   G   V   P   D   R   F   S   G   S   G   S   G   T   D TTC ACT TTC ACC ATC AGC AGT GTG CAG GCT GAA GAC CTG GCA GTT TAT TAC TGT
 F   T   F   T   I   S   S   V   Q   A   E   D   L   A   V   Y   Y   C CAG CAA CAT TAT ACT TCT CCA TTC ACG TTC GGC TCG GGG ACA AAC TTG GAA ATA
 Q   Q   H   Y   T   S   P   F   T   F   G   S   G   T   N   L   E   I

AAA C
 K
```

| $V_H$ | Murine MC3 | Human Consensus ($V_HI$) | Humanization Protocol | | Humanized MC3 |
|---|---|---|---|---|---|
| | | | Murine Retained | Humanized | |
| 1 | E | Q | Yes (contact CDR) | Not humanized | E |
| 2 | V | V | Yes (same as human) | n/a | V |
| 3 | Q | Q | Yes (same as human) | n/a | Q |
| 4 | L | L | Yes (same as human) | n/a | L |
| 5 | Q | V | No | Humanized | V |
| 6 | Q | Q | Yes (same as human) | n/a | Q |
| 7 | S | S | Yes (same as human) | n/a | S |
| 8 | G | G | Yes (same as human) | n/a | G |
| 9 | P | A | No | Humanized (BR) | A |
| 10 | E | E | Yes (same as human) | n/a | E |
| 11 | L | V | No | Humanized | V |
| 12 | V | K | No | Humanized (BR) | K |
| 13 | K | K | Yes (same as human) | n/a | K |
| 14 | P | P | Yes (same as human) | n/a | P |
| 15 | G | G | Yes (same as human) | n/a | G |
| 16 | A | A | Yes (same as human) | n/a | A |
| 17 | S | S | Yes (same as human) | n/a | S |
| 18 | M | V | No | Humanized (BR) | V |
| 19 | K | K | Yes (same as human) | n/a | K |
| 20 | I | V | No | Humanized (BR) | V |
| 21 | S | S | Yes (same as human) | n/a | S |
| 22 | C | C | Yes (same as human) | n/a | C |
| 23 | E | K | No | Humanized | K |
| 24 | A | A | Yes (same as human) | n/a | A |
| 25 | S | S | Yes (same as human) | n/a | S |
| 26 | G | G | Yes (same as human) | n/a | G |
| 27 | Y | Y | Yes (same as human) | n/a | Y |
| 28 | S | T | Yes (contact CDR) | Not humanized | S |
| 29 | P | P | Yes (same as human) | n/a | P |
| 30 | T | T | Yes (same as human) | n/a | T |
| 31 | G | S | Yes (CDR) | Not humanized | G |
| 32 | Y | Y | Yes (CDR) | n/a | Y |

Figure 12 - 1

| $V_H$ | Murine MC3 | Human Consensus $(V_H I)$ | Humanization Protocol | | Humanized MC3 |
|---|---|---|---|---|---|
| | | | Murine Retained | Humanized | |
| 33 | T | A | Yes (CDR) | Not humanized | T |
| 34 | M | I | Yes (CDR) | Not humanized | M |
| 35 | H | S | Yes (CDR) | Not humanized | H |
| 36 | W | W | Yes (same as human) | n/a | W |
| 37 | V | V | Yes (same as human) | n/a | V |
| 38 | K | R | Yes (contact CDR) | Not humanized | K |
| 39 | Q | Q | Yes (same as human) | n/a | Q |
| 40 | S | A | Yes (contact CDR) | Not humanized | S |
| 41 | H | P | No | Humanized | P |
| 42 | G | G | Yes (same as human) | n/a | G |
| 43 | M | Q | Yes (interchain cont.) | Not humanized | M |
| 44 | N | G | Yes (interchain cont.) | Not humanized | N |
| 45 | L | L | Yes (same as human) | n/a | L |
| 46 | E | E | Yes (same as human) | n/a | E |
| 47 | W | W | Yes (same as human) | n/a | W |
| 48 | I | M | Yes (contact CDR) | Not humanized | I |
| 49 | G | G | Yes (same as human) | n/a | G |
| 50 | L | W | Yes (CDR) | Not humanized | L |
| 51 | I | I | Yes (CDR) | n/a | I |
| 52 | N | N | Yes (CDR) | n/a | N |
| 52a | P | P | Yes (CDR) | n/a | P |
| 52b | Y | Y | Yes (CDR) | n/a | Y |
| 53 | N | G | Yes (CDR) | Not humanized | N |
| 54 | G | N | Yes (CDR) | Not humanized | G |
| 55 | G | G | Yes (CDR) | n/a | G |
| 56 | | D | Yes (CDR) | Not humanized | |
| 57 | T | T | Yes (CDR) | n/a | T |
| 58 | V | N | Yes (CDR) | Not humanized | V |
| 59 | Y | Y | Yes (CDR) | n/a | Y |
| 60 | N | A | Yes (CDR) | Not humanized | N |
| 61 | Q | Q | Yes (CDR) | n/a | Q |
| 62 | K | K | Yes (CDR) | n/a | K |

Figure 12 - 2

| $V_H$ | Murine MC3 | Human Consensus ($V_H$I) | Humanization Protocol | | Humanized MC3 |
|---|---|---|---|---|---|
| | | | Murine Retained | Humanized | |
| 63 | F | F | Yes (CDR) | n/a | F |
| 64 | Q | Q | Yes (CDR) | n/a | Q |
| 65 | D | G | Yes (CDR) | Not humanized | D |
| 66 | K | R | Yes (contact CDR) | Not humanized | K |
| 67 | A | V | Yes (contact CDR) | Not humanized | A |
| 68 | T | T | Yes (same as human) | n/a | T |
| 69 | L | I | Yes (contact CDR) | Not humanized | L |
| 70 | T | T | Yes (same as human) | n/a | T |
| 71 | V | A | Yes (contact CDR) | Not humanized | V |
| 72 | D | D | Yes (same as human) | n/a | D |
| 73 | K | T | Yes (contact CDR) | Not humanized | K |
| 74 | S | S | Yes (same as human) | n/a | S |
| 75 | S | T | No | Humanized | T |
| 76 | G | S | No | Humanized (BR) | S |
| 77 | T | T | Yes (same as human) | n/a | T |
| 78 | A | A | Yes (same as human) | n/a | A |
| 79 | Y | Y | Yes (same as human) | n/a | Y |
| 80 | M | M | Yes (same as human) | n/a | M |
| 81 | E | E | Yes (same as human) | n/a | E |
| 82 | L | L | Yes (same as human) | n/a | L |
| 82a | L | S | No | Humanized | S |
| 82b | S | S | Yes (same as human) | n/a | S |
| 82c | L | L | Yes (same as human) | n/a | L |
| 83 | T | R | No | Humanized | R |
| 84 | S | S | Yes (same as human) | n/a | S |
| 85 | E | E | Yes (same as human) | n/a | E |
| 86 | D | D | Yes (same as human) | n/a | D |
| 87 | S | T | No | Humanized | T |
| 88 | A | A | Yes (same as human) | n/a | A |
| 89 | V | V | Yes (same as human) | n/a | V |
| 90 | Y | Y | Yes (same as human) | n/a | Y |
| 91 | F | Y | Yes (interchain cont.) | Not humanized | F |

Figure 12 - 3

| $V_H$ | Murine MC3 | Human Consensus ($V_H I$) | Humanization Protocol | | Humanized MC3 |
|---|---|---|---|---|---|
| | | | Murine Retained | Humanized | |
| 92 | C | C | Yes (same as human) | n/a | C |
| 93 | A | A | Yes (same as human) | n/a | A |
| 94 | R | R | Yes (same as human) | n/a | R |
| 95 | R | A | Yes (CDR) | Not humanized | R |
| 96 | - | P | Yes (CDR) | Not humanized | - |
| 97 | - | G | Yes (CDR) | Not humanized | - |
| 98 | - | Y | Yes (CDR) | Not humanized | - |
| 99 | - | G | Yes (CDR) | Not humanized | - |
| 100 | - | S | Yes (CDR) | Not humanized | - |
| 100a | - | G | Yes (CDR) | Not humanized | - |
| 100b | - | G | Yes (CDR) | Not humanized | - |
| 100c | - | G | Yes (CDR) | Not humanized | - |
| 100d | - | C | Yes (CDR) | Not humanized | - |
| 100e | W | Y | Yes (CDR) | Not humanized | W |
| 100f | R | R | Yes (CDR) | n/a | R |
| 100g | - | G | Yes (CDR) | Not humanized | - |
| 100h | - | D | Yes (CDR) | Not humanized | - |
| 100i | Y | Y | Yes (CDR) | n/a | Y |
| 100j | T | X | Yes (CDR) | Not humanized | T |
| 100k | M | F | Yes (CDR) | Not humanized | M |
| 101 | D | D | Yes (CDR) | n/a | D |
| 102 | Y | Y | Yes (CDR) | n/a | Y |
| 103 | W | W | Yes (same as human) | n/a | W |
| 104 | G | G | Yes (same as human) | n/a | G |
| 105 | Q | Q | Yes (same as human) | n/a | Q |
| 106 | G | G | Yes (same as human) | n/a | G |
| 107 | T | T | Yes (same as human) | n/a | T |
| 108 | S | L | No | Humanized | L |
| 109 | V | V | Yes (same as human) | n/a | V |
| 110 | T | T | Yes (same as human) | n/a | T |
| 111 | V | V | Yes (same as human) | n/a | V |
| 112 | S | S | Yes (same as human) | n/a | S |

Figure 12 - d

| $V_H$ | Murine MC3 | Human Consensus ($V_H I$) | Humanization Protocol | | Humanized MC3 |
|---|---|---|---|---|---|
| | | | Murine Retained | Humanized | |
| 113 | S | S | Yes (same as human) | n/a | S |

Figure 12 - 5

| $V_K$ | Murine MC3 | Human Consensus ($V_K$IV) | Humanization Protocol | | Humanized MC3 |
|---|---|---|---|---|---|
| | | | Murine Retained | Humanized | |
| 1 | D | D | Yes (same as human) | n/a | D |
| 2 | I | I | Yes (same as human) | n/a | I |
| 3 | V | V | Yes (same as human) | n/a | V |
| 4 | M | M | Yes (same as human) | n/a | M |
| 5 | T | T | Yes (same as human) | n/a | T |
| 6 | Q | Q | Yes (same as human) | n/a | Q |
| 7 | S | S | Yes (same as human) | n/a | S |
| 8 | H | P | No | Humanized | P |
| 9 | K | D | No | Humanized | D |
| 10 | P | S | No | Humanized | S |
| 11 | M | L | No | Humanized (BR) | L |
| 12 | S | A | No | Humanized | A |
| 13 | T | V | No | Humanized (BR) | V |
| 14 | S | S | Yes (same as human) | n/a | S |
| 15 | E | L | No | Humanized | L |
| 16 | G | G | Yes (same as human) | n/a | G |
| 17 | D | E | No | Humanized | E |
| 18 | W | R | No | Humanized | R |
| 19 | V | A | No | Humanized (BR) | A |
| 20 | S | T | No | Humanized | T |
| 21 | I | I | Yes (same as human) | n/a | I |
| 22 | T | N | Yes (contact CDR) | Not humanized | T |
| 23 | C | C | Yes (same as human) | n/a | C |
| 24 | K | K | Yes (CDR) | n/a | K |
| 25 | A | S | Yes (CDR) | Not humanized | A |
| 26 | S | S | Yes (CDR) | n/a | S |
| 27 | Q | Q | Yes (CDR) | n/a | Q |
| 27a | D | S | Yes (CDR) | Not humanized | D |
| 27b | V | V | Yes (CDR) | n/a | V |
| 27c | S | L | Yes (CDR) | Not humanized | S |
| 27d | I | Y | Yes (CDR) | Not humanized | I |
| 27e | G | S | Yes (CDR) | Not humanized | G |

Figure 13 - 1

| $V_K$ | Murine MC3 | Human Consensus ($V_K$IV) | Humanization Protocol | | Humanized MC3 |
|---|---|---|---|---|---|
| | | | Murine Retained | Humanized | |
| 27f | - | S | Yes (CDR) | Not humanized | - |
| 28 | - | N | Yes (CDR) | Not humanized | - |
| 29 | - | N | Yes (CDR) | Not humanized | - |
| 30 | - | K | Yes (CDR) | Not humanized | - |
| 31 | - | N | Yes (CDR) | Not humanized | - |
| 32 | - | Y | Yes (CDR) | Not humanized | - |
| 33 | V | L | Yes (CDR) | Not humanized | V |
| 34 | A | A | Yes (CDR) | n/a | A |
| 35 | W | W | Yes (same as human) | n/a | W |
| 36 | Y | Y | Yes (same as human) | n/a | Y |
| 37 | Q | Q | Yes (same as human) | n/a | Q |
| 38 | Q | Q | Yes (same as human) | n/a | Q |
| 39 | K | K | Yes (same as human) | n/a | K |
| 40 | P | P | Yes (same as human) | n/a | P |
| 41 | G | G | Yes (same as human) | n/a | G |
| 42 | Q | Q | Yes (same as human) | n/a | Q |
| 43 | S | P | Yes (interchain cont.) | Not humanized | S |
| 44 | P | P | Yes (same as human) | n/a | P |
| 45 | K | K | Yes (same as human) | n/a | K |
| 46 | L | L | Yes (same as human) | n/a | L |
| 47 | L | L | Yes (same as human) | n/a | L |
| 48 | I | I | Yes (same as human) | n/a | I |
| 49 | Y | Y | Yes (same as human) | n/a | Y |
| 50 | S | W | Yes (CDR) | Not humanized | S |
| 51 | A | A | Yes (CDR) | n/a | A |
| 52 | S | S | Yes (CDR) | n/a | S |
| 53 | S | T | Yes (CDR) | Not humanized | S |
| 54 | R | R | Yes (CDR) | n/a | R |
| 55 | Y | E | Yes (CDR) | Not humanized | Y |
| 56 | T | S | Yes (CDR) | Not humanized | T |
| 57 | G | G | Yes (same as human) | n/a | G |
| 58 | V | V | Yes (same as human) | n/a | V |

Figure 13 - 2

| $V_K$ | Murine MC3 | Human Consensus ($V_K$IV) | Humanization Protocol | | Humanized MC3 |
|---|---|---|---|---|---|
| | | | Murine Retained | Humanized | |
| 59 | P | P | Yes (same as human) | n/a | P |
| 60 | D | D | Yes (same as human) | n/a | D |
| 61 | R | R | Yes (same as human) | n/a | R |
| 62 | F | F | Yes (same as human) | n/a | F |
| 63 | S | S | Yes (same as human) | n/a | S |
| 64 | G | G | Yes (same as human) | n/a | G |
| 65 | S | S | Yes (same as human) | n/a | S |
| 66 | G | G | Yes (same as human) | n/a | G |
| 67 | S | S | Yes (same as human) | n/a | S |
| 68 | G | G | Yes (same as human) | n/a | G |
| 69 | T | T | Yes (same as human) | n/a | T |
| 70 | D | D | Yes (same as human) | n/a | D |
| 71 | F | F | Yes (same as human) | n/a | F |
| 72 | T | T | Yes (same as human) | n/a | T |
| 73 | F | L | No | Humanized (BR) | L |
| 74 | T | T | Yes (same as human) | n/a | T |
| 75 | I | I | Yes (same as human) | n/a | I |
| 76 | S | S | Yes (same as human) | n/a | S |
| 77 | S | S | Yes (same as human) | n/a | S |
| 78 | V | L | No | Humanized (BR) | L |
| 79 | Q | Q | Yes (same as human) | n/a | Q |
| 80 | A | A | Yes (same as human) | n/a | A |
| 81 | E | E | Yes (same as human) | n/a | E |
| 82 | D | D | Yes (same as human) | n/a | D |
| 83 | L | V | No | Humanized (BR) | V |
| 84 | A | A | Yes (same as human) | n/a | A |
| 85 | V | V | Yes (same as human) | n/a | V |
| 86 | Y | Y | Yes (same as human) | n/a | Y |
| 87 | Y | Y | Yes (same as human) | n/a | Y |
| 88 | C | C | Yes (same as human) | n/a | C |
| 89 | Q | Q | Yes (CDR) | n/a | Q |
| 90 | Q | Q | Yes (CDR) | n/a | Q |

Figure 13 - 3

| $V_K$ | Murine MC3 | Human Consensus ($V_K$IV) | Humanization Protocol | | Humanized MC3 |
|---|---|---|---|---|---|
| | | | Murine Retained | Humanized | |
| 91 | H | Y | Yes (CDR) | Not humanized | H |
| 92 | Y | Y | Yes (CDR) | n/a | Y |
| 93 | T | S | Yes (CDR) | Not humanized | T |
| 94 | S | T | Yes (CDR) | Not humanized | S |
| 95 | P | P | Yes (CDR) | n/a | P |
| 96 | P | X | Yes (CDR) | Not humanized | P |
| 97 | T | T | Yes (CDR) | n/a | T |
| 98 | F | F | Yes (same as human) | n/a | F |
| 99 | G | G | Yes (same as human) | n/a | G |
| 100 | S | Q | Yes (interchain cont.) | Not humanized | S |
| 101 | G | G | Yes (same as human) | n/a | G |
| 102 | T | T | Yes (same as human) | n/a | T |
| 103 | N | K | No | Humanized | K |
| 104 | L | V | No | Humanized (BR) | V |
| 105 | E | E | Yes (same as human) | n/a | E |
| 106 | I | I | Yes (same as human) | n/a | I |
| 107 | K | K | Yes (same as human) | n/a | K |

Figure 13 - 4

Figure 14: HuMc3 $V_H$ (BR-R version)

```
mkcsw vilfl lsgta gvhsE VQLVQ SGPEV VKPGA SMKIS CKASG YSFTG   50

YTMH  WVKQSP GMNLE WIGLI NPYNG GTVYN QKFQD KATLT VDKST GTAYM  100

ELSSL RSEDT AVYFC ARRWR YTMDY WGQGT LVTVS S                   136
```

Figure 15: HuMc3 $V_\kappa$ (BR-R version)

```
mefqt qvfvf vflwl sgvdg DIVMT QSPDS MATSL GERVT ITCKA SQDVS   50

IGVAW YQQKP GQSPK LLIYS ASSRY TGVPD RFSGS GSGTD FTFTI SSVQA   100

EDLAV YYCQQ HYTSP FTFGS GTKLE IK                              127
```

FIGURE 16

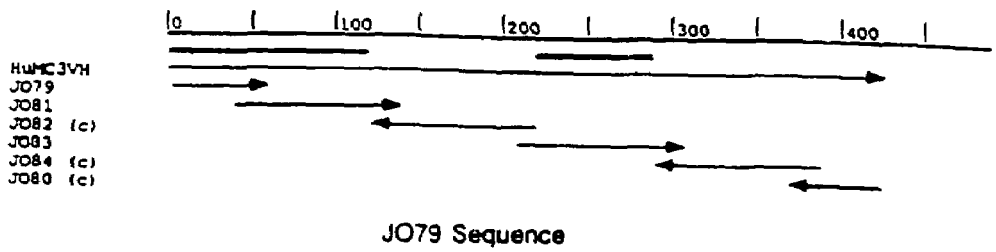

JO79 Sequence

```
         10         20         30         40         50
1234567890 1234567890 1234567890 1234567890 1234567890
GATATCCACC ATGAAATGCA GCTGGGTCAT TCTCTTCCTC CTGTCAGGAA     50
CTGCAGGT                                                  58
```

JO80 Sequence

```
         10         20         30         40         50
1234567890 1234567890 1234567890 1234567890 1234567890
GCTAGCTGAG GAGACGGTGA CCAGGGTTCC TTGACCCCAA TAGTCCATAG     50
TATATCT                                                   57
```

JO82 Sequence

```
         10         20         30         40         50
1234567890 1234567890 1234567890 1234567890 1234567890
TAAGTCCAAT CCACTCAAGG TTCATTCCAG GGCTCTGCTT CACCCAGTGC     50
ATGGTATAGC CAGTGAATGA GTAACCAGAA GCCTTGCAGG AGACCTTCAC    100
```

JO83 Sequence

```
         10         20         30         40         50
1234567890 1234567890 1234567890 1234567890 1234567890
GATTGGACTT ATTAATCCTT ACAATGGTGG TACTGTCTAC AACCAGAAGT     50
TCCAGGACAA GGCCACATTA ACTGTAGACA AGTCAACGAG CACAGCCTAC    100
```

JO84 Sequence

```
         10         20         30         40         50
1234567890 1234567890 1234567890 1234567890 1234567890
CAATAGTCCA TAGTATATCT CCAACGTCTT GCACAGAAAT AGACTGCCGT     50
GTCCTCAGAT CTCAGACTGC TGAGCTCCAT GTAGGCTGTG CTGGTTGACT    100
```

JO81 Sequence

```
         10         20         30         40         50
1234567890 1234567890 1234567890 1234567890 1234567890
TCCTGTCAGG AACTGCAGGT GTCCACTCTG AGGTCCAGCT GGTGCAGTCT     50
CGAGCTCAGG TGAAGAAGCC TGGAGCTTCA GTGAAGGTCT CCTGCAAGGC    100
```

FIGURE 17

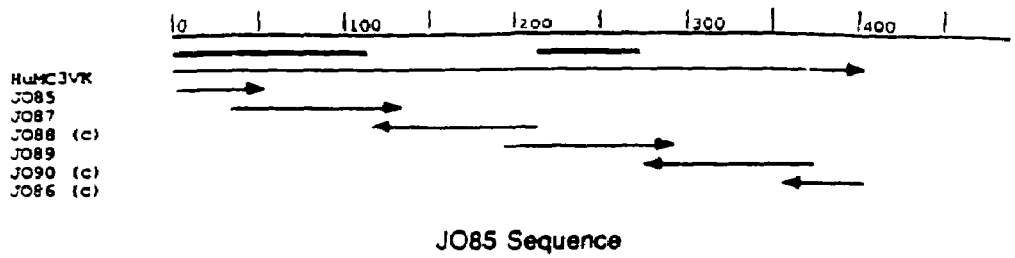

JO85 Sequence

```
         10         20         30         40         50
1234567890 1234567890 1234567890 1234567890 1234567890
GATATCCACT ATGGAGTTCC AGACCCAGGT CTTTGTATTC GTGTTTCTCT    50
GG                                                       52
```

JO86 Sequence

```
         10         20         30         40         50
1234567890 1234567890 1234567890 1234567890 1234567890
gtcgacTTAC GTTTTATTTC CACCTTTGTC CCCGAGCCGA ACGTGAATGG    50
```

JO87 Sequence

```
         10         20         30         40         50
1234567890 1234567890 1234567890 1234567890 1234567890
TTGTATTGGT GTTTCTCTGG TTGTCTGGTG TTGACGGAGA CATTGTGATG    50
ACCCAGTCTC CAGACTCCCT GGCTGTGTCA CTGGGAGAGA GGGCCACCAT   100
```

JO88 Sequence

```
         10         20         30         40         50
1234567890 1234567890 1234567890 1234567890 1234567890
TCAGCAGTTT AGGAGATTGT CCTGGTTTCT GTTGATACCA GGCTACACCA    50
ATACTCACAT CCTGACTGGC CTTGCAGGTG ATGGTGGCCC TCTCTCCCAG   100
```

JO89 Sequence

```
         10         20         30         40         50
1234567890 1234567890 1234567890 1234567890 1234567890
ACAATCTCCT AAACTGCTGA TTTACTCGGC ATCCTCCCGG TACACTGGAG    50
TCCCTGATCG CTTCAGTGGC AGTGGATCTG GGACGGATTT CACTCTCACC   100
```

JO90 Sequence

```
         10         20         30         40         50
1234567890 1234567890 1234567890 1234567890 1234567890
CCCGAGCCGA ACGTGAATGG AGAAGTATAA TGTTGCTGAC AGTAATAAAC    50
TGCCACGTCT TCAGCCTCCA GACTGCTGAT GGTGAGAGTG AAATCCGTCC   100
```

Figure 18: HuMc3 V$_H$ (BR-M version)

Fig. 18A

```
--g ata tcc acc ATG AAA TGC AGC TGG GTC ATT CTC TTC CTC CTG TCA GGA    49

ACT GCA GGT GTC CAC TCT GAG GTC CAG CTG GTG CAG TCT GGA GCT GAG GTG   100

AAG AAG CCT GGA GCT TCA GTG AAG GTC TCC TGC AAG GCT TCT GGT TAC TCA   151

TTC ACT GGC TAT ACC ATG CAC TGG GTG AAG CAG AGC CCT GGA ATG AAC CTT   202

GAG TGG ATT GGA CTT ATT AAT CCT TAC AAT GGT GGT ACT GTC TAC AAC CAG   253

AAG TTC CAG GAC AAG GCC ACA TTA ACT GTA GAC AAG TCA ACG AGC ACA GCC   304

TAC ATG GAG CTC AGC AGT CTG AGA TCT GAG GAC ACG GCA GTC TAT TTC TGT   355

GCA AGA CGT TGG AGA TAT ACT ATG GAC TAT TGG GGT CAA GGA ACC CTG GTC   406

ACC GTC TCC TCA gct agc                                               424
```

Fig. 18B

```
MKCSW VILFL LSGTA GVHSE VQLVQ SGAEV KKPGA SVKVS CKASG YSFTG     50

YTMHW VKQSP GMNLE WIGLI NPYNG GTVYN QKFQD KATLT VDKST STAYM   100

ELSSL RSEDT AVYFC ARRWR YTMDY WGQGT LVTVS S                   136
```

Figure 19: HuMc3 V$_K$ (BR-M version)

Fig. 19A

```
--g ata tcc acc ATG GAG TTC CAG ACC CAG GTC TTT GTA TTC GTG TTT CTC    49

TGG TTG TCT GGT GTT GAC GGA GAC ATT GTG ATG ACC CAG TCT CCA GAC TCC   100

CTG GCT GTG TCA CTG GGA GAG AGG GCC ACC ATC ACC TGC AAG GCC AGT CAG   151

GAT GTG AGT ATT GGT GTA GCC TGG TAT CAA CAG AAA CCA GGA CAA TCT CCT   202

AAA CTG CTG ATT TAC TCG GCA TCC TCC CGG TAC ACT GGA GTC CCT GAT CGC   253

TTC AGT GGC AGT GGA TCT GGG ACG GAT TTC ACT CTC ACC ATC AGC AGT CTG   304

CAG GCT GAA GAC GTG GCA GTT TAT TAC TGT CAG CAA CAT TAT ACT TCT CCA   355

TTC ACG TTC GGC TCG GGG ACA AAG GTG GAA ATA AAA cgt aag tcg ac        404
```

Fig. 19B

```
MEFQT QVFVF VFLWL SGVDG DIVMT QSPDS LAVSL GERAT ITCKA SQDVS     50

IGVAW YQQKP GQSPK LLIYS ASSRY TGVPD RFSGS GSGTD FTLTI SSLQA    100

EDVAV YYCQQ HYTSP FTFGS GTKVE IK                              127
```

Figure 23
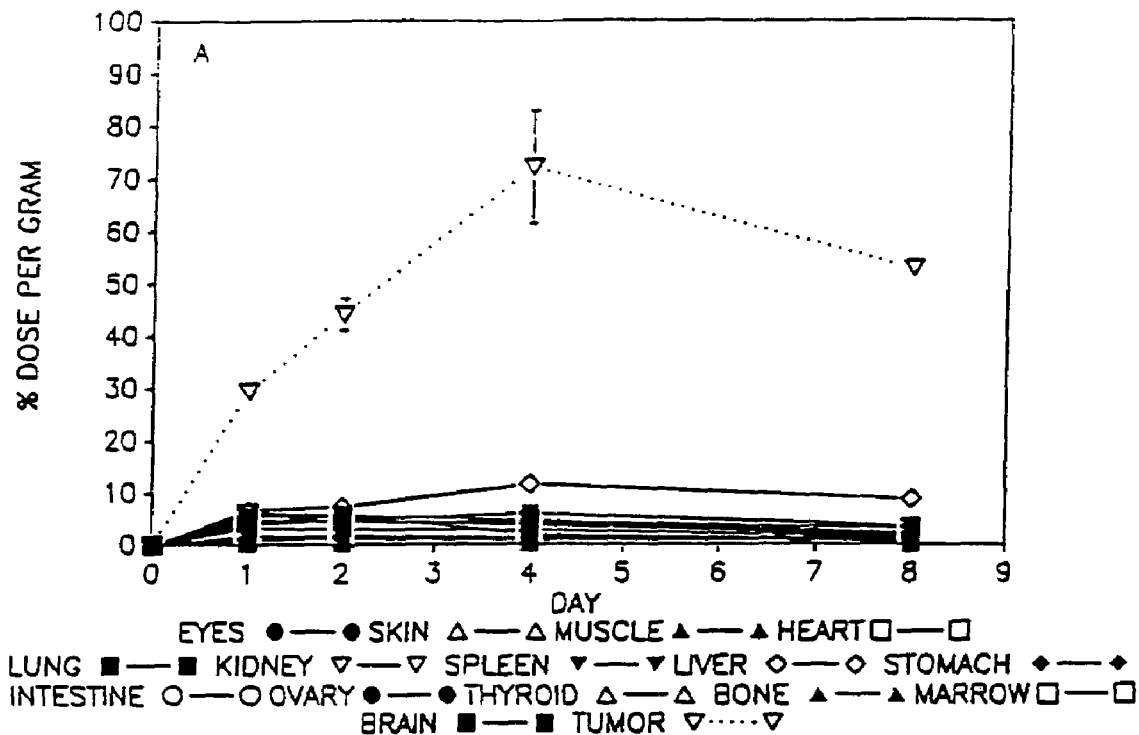
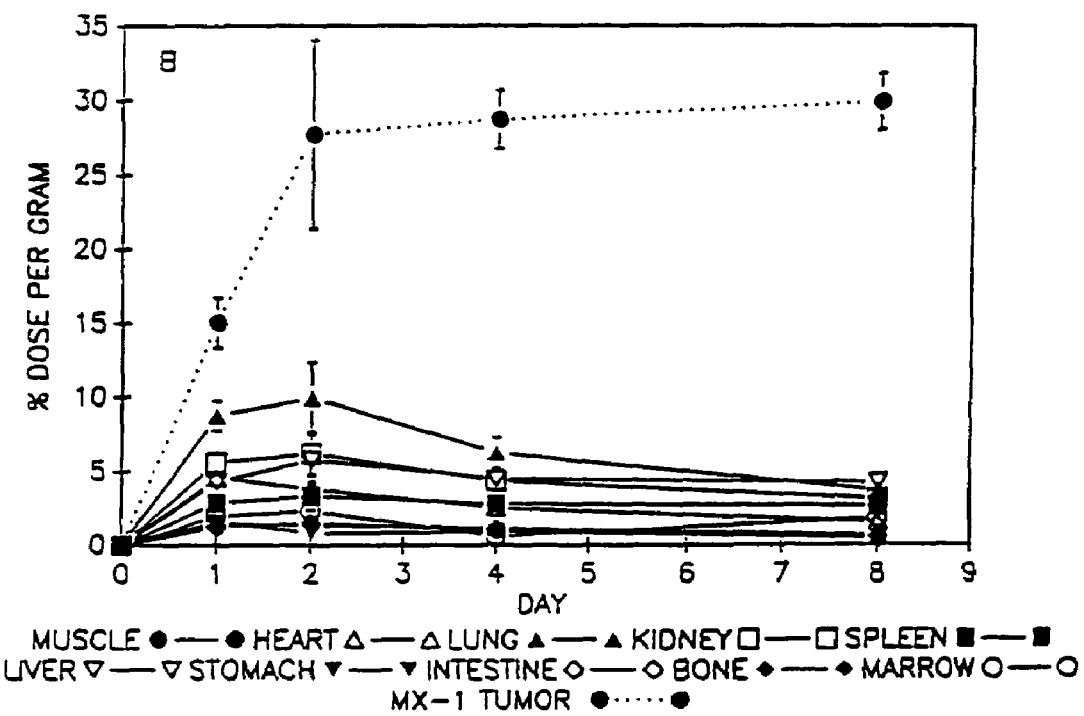

SEQUENCE LISTING (1) GENERAL INFORMATION:

(iii) NUMBER OF SEQUENCES: 81

(2) INFORMATION FOR SEQ ID NO: 1:

(i) SEQUENCE CHARACTERISTICS:
       (A) LENGTH: 29 amino acids
       (B) TYPE: amino acid
       (C) STRANDEDNESS: single
       (D) TOPOLOGY: linear (xi) SEQUENCE DESCRIPTION: SEQ ID NO: 1:

Glu Ile Leu Gln Thr Ala Val Ile Cys Ser Ala Ser Ser Val Ser
1               5                   10                  15

Ser Leu His Trp Tyr Gln Gln Ser Pro Pro Trp Ile Tyr
            20                  25

(2) INFORMATION FOR SEQ ID NO: 2:

(i) SEQUENCE CHARACTERISTICS:
       (A) LENGTH: 38 amino acids
       (B) TYPE: amino acid
       (C) STRANDEDNESS: single
       (D) TOPOLOGY: linear (xi) SEQUENCE DESCRIPTION: SEQ ID NO: 2:

Asp Ile Val Met Thr Gln Leu Val Val Met Cys Lys Ser Ser Gln Ser
1               5                   10                  15

Leu Leu Asn Ser Gly Asn Gln Lys Asn Phe Leu Ala Trp Tyr Gln Gln
            20                  25                  30

Pro Pro Leu Leu Ile Tyr
        35

(2) INFORMATION FOR SEQ ID NO: 3:

(i) SEQUENCE CHARACTERISTICS:
       (A) LENGTH: 31 amino acids
       (B) TYPE: amino acid
       (C) STRANDEDNESS: single
       (D) TOPOLOGY: linear (xi) SEQUENCE DESCRIPTION: SEQ ID NO: 3:

Asp Ile Val Leu Gln Leu Val Val Leu Cys Arg Ala Ser Gln Ser Ile
1               5                   10                  15

Gly Asn Asn Leu His Trp Tyr Gln Gln Ser Pro Leu Leu Ile Lys
            20                  25                  30

(2) INFORMATION FOR SEQ ID NO: 4:

(i) SEQUENCE CHARACTERISTICS:
       (A) LENGTH: 30 amino acids
       (B) TYPE: amino acid
       (C) STRANDEDNESS: single
       (D) TOPOLOGY: linear (xi) SEQUENCE DESCRIPTION: SEQ ID NO: 4:

Asp Ile Val Leu Gln Met Ala Val Met Cys Ser Ala Ser Ser Ser Val
1               5                   10                  15

Asn Tyr Met Tyr Trp Tyr Gln Gln Ser Pro Arg Trp Ile Tyr
            20                  25                  30

(2) INFORMATION FOR SEQ ID NO: 5:

(i) SEQUENCE CHARACTERISTICS:
       (A) LENGTH: 31 amino acids
       (B) TYPE: amino acid
       (C) STRANDEDNESS: single
       (D) TOPOLOGY: linear (xi) SEQUENCE DESCRIPTION: SEQ ID NO: 5:

Ile Gln Met Thr Gln Leu Ala Val Ile Cys Arg Ala Ser Gln Asp Ile
1               5                   10                  15

Ser Asn Tyr Leu Asn Trp Tyr Gln Gln Thr Lys Leu Leu Val Tyr
            20                  25                  30

(2) INFORMATION FOR SEQ ID NO: 6:

(i) SEQUENCE CHARACTERISTICS:
       (A) LENGTH: 37 amino acids
       (B) TYPE: amino acid
       (C) STRANDEDNESS: single
       (D) TOPOLOGY: linear (xi) SEQUENCE DESCRIPTION: SEQ ID NO: 6:

Asp Val Val Met Thr Gln Leu Val Ala Ile Cys Arg Ser Ser Gln Ser
1               5                   10                  15

Leu Val His Ser Gln Gly Asn Thr Tyr Leu Arg Trp Tyr Leu Gln Pro
            20                  25                  30

Lys Val Leu Ile Tyr
        35

(2) INFORMATION FOR SEQ ID NO: 7:

(i) SEQUENCE CHARACTERISTICS:
       (A) LENGTH: 30 amino acids
       (B) TYPE: amino acid
       (C) STRANDEDNESS: single
       (D) TOPOLOGY: linear (xi) SEQUENCE DESCRIPTION: SEQ ID NO: 7:

Asp Ile Gln Met Gln Leu Ala Val Ile Cys Arg Ala Ser Gln Asp Ile
1               5                   10                  15

Asn Asn Phe Leu Asn Trp Tyr Gln Gln Ile Leu Leu Ile Tyr
            20                  25                  30

(2) INFORMATION FOR SEQ ID NO: 8:

(i) SEQUENCE CHARACTERISTICS:
       (A) LENGTH: 37 amino acids
       (B) TYPE: amino acid
       (C) STRANDEDNESS: single
       (D) TOPOLOGY: linear (xi) SEQUENCE DESCRIPTION: SEQ ID NO: 8:

Val Leu Met Gln Thr Leu Val Ala Ile Ser Cys Arg Ser Asn Gln Thr
1               5                   10                  15

Ile Leu Leu Ser Asp Gly Asp Thr Tyr Leu Glu Trp Tyr Leu Gln Ser
            20                  25                  30

Pro Leu Leu Ile Tyr
        35

(2) INFORMATION FOR SEQ ID NO: 9:

(i) SEQUENCE CHARACTERISTICS:
       (A) LENGTH: 30 amino acids
       (B) TYPE: amino acid (C) STRANDEDNESS: single
        (D) TOPOLOGY: linear (xi) SEQUENCE DESCRIPTION: SEQ ID NO: 9:

Asp Ile Met Gln Leu Ala Val Ile Cys Arg Ala Ser Gly Asn Ile His
1               5                  10                  15

Asn Tyr Leu Ala Trp Tyr Gln Gln Ser Pro Leu Leu Val Tyr
            20                  25                  30

(2) INFORMATION FOR SEQ ID NO: 10:

(i) SEQUENCE CHARACTERISTICS:
        (A) LENGTH: 32 amino acids
        (B) TYPE: amino acid
        (C) STRANDEDNESS: single
        (D) TOPOLOGY: linear (xi) SEQUENCE DESCRIPTION: SEQ ID NO: 10:

Glu Ile Ser Lys Leu Ala Ser Val Arg Phe Tyr Leu Ile Met Asp Ala
1               5                  10                  15

Tyr Tyr Cys Gln Gln Trp Thr Tyr Pro Leu Ile Thr Phe Thr Leu Leu
            20                  25                  30

(2) INFORMATION FOR SEQ ID NO: 11:

(i) SEQUENCE CHARACTERISTICS:
        (A) LENGTH: 37 amino acids
        (B) TYPE: amino acid
        (C) STRANDEDNESS: single
        (D) TOPOLOGY: linear (xi) SEQUENCE DESCRIPTION: SEQ ID NO: 11:

Gly Ala Ser Thr Arg Glu Ser Val Asp Arg Phe Ser Thr Asp Phe Leu
1               5                  10                  15

Ile Val Asp Ala Tyr Tyr Cys Gln Asn Asp His Ser Tyr Pro Leu Thr
            20                  25                  30

Phe Ala Thr Leu Ile
        35

(2) INFORMATION FOR SEQ ID NO: 12:

(i) SEQUENCE CHARACTERISTICS:
        (A) LENGTH: 33 amino acids
        (B) TYPE: amino acid
        (C) STRANDEDNESS: single
        (D) TOPOLOGY: linear (xi) SEQUENCE DESCRIPTION: SEQ ID NO: 12:

Tyr Ala Ser Gln Ser Ile Ser Ile Arg Phe Thr Phe Leu Ile Val Asp
1               5                  10                  15

Met Tyr Phe Cys Gln Gln Ser Asn Ser Trp Pro Tyr Thr Phe Thr Leu
            20                  25                  30

Ile (2) INFORMATION FOR SEQ ID NO: 13:

(i) SEQUENCE CHARACTERISTICS:
        (A) LENGTH: 31 amino acids
        (B) TYPE: amino acid
        (C) STRANDEDNESS: single
        (D) TOPOLOGY: linear (xi) SEQUENCE DESCRIPTION: SEQ ID NO: 13:

Asp Thr Ser Lys Leu Ala Ser Val Arg Phe Tyr Leu Ile Met Asp Ala

```
                 1               5                  10                 15
Tyr Tyr Cys Gln Gln Trp Gly Arg Asn Pro Thr Phe Thr Leu Ile
                20                  25                 30

(2) INFORMATION FOR SEQ ID NO: 14:

(i) SEQUENCE CHARACTERISTICS:
        (A) LENGTH: 32 amino acids
        (B) TYPE: amino acid
        (C) STRANDEDNESS: single
        (D) TOPOLOGY: linear (xi) SEQUENCE DESCRIPTION: SEQ ID NO: 14:

Tyr Thr Ser Arg Leu His Ser Val Arg Phe Asp Tyr Leu Ile Leu Asp
1               5                   10                  15
Ala Thr Tyr Cys Gln Gln Gly Ser Thr Thr Pro Arg Thr Phe Thr Leu
                20                  25                 30

(2) INFORMATION FOR SEQ ID NO: 15:

(i) SEQUENCE CHARACTERISTICS:
        (A) LENGTH: 31 amino acids
        (B) TYPE: amino acid
        (C) STRANDEDNESS: single
        (D) TOPOLOGY: linear (xi) SEQUENCE DESCRIPTION: SEQ ID NO: 15:

Lys Val Ser Asn Arg Phe Ser Val Asp Arg Phe Thr Phe Leu Ile Val
1               5                   10                  15
Asp Tyr Cys Ser Gln Ser Thr His Val Pro Trp Thr Phe Thr Leu
                20                  25                 30

(2) INFORMATION FOR SEQ ID NO: 16:

(i) SEQUENCE CHARACTERISTICS:
        (A) LENGTH: 34 amino acids
        (B) TYPE: amino acid
        (C) STRANDEDNESS: single
        (D) TOPOLOGY: linear (xi) SEQUENCE DESCRIPTION: SEQ ID NO: 16:

Phe Thr Ser Arg Ser Gln Ser Val Arg Phe Thr Asp Tyr Leu Ile Leu
1               5                   10                  15
Asp Ala Tyr Phe Cys Gln Gln Gly Asn Ala Leu Pro Arg Thr Phe Thr
                20                  25                 30
Leu Ile (2) INFORMATION FOR SEQ ID NO: 17:

(i) SEQUENCE CHARACTERISTICS:
        (A) LENGTH: 34 amino acids
        (B) TYPE: amino acid
        (C) STRANDEDNESS: single
        (D) TOPOLOGY: linear (xi) SEQUENCE DESCRIPTION: SEQ ID NO: 17:

Lys Val Ser Asn Arg Phe Ser Val Asp Arg Phe Thr Phe Leu Ile Val
1               5                   10                  15
Asp Val Tyr Tyr Cys Phe Gln Gly Ser His Val Pro Pro Thr Phe Thr
                20                  25                 30
Leu Ile (2) INFORMATION FOR SEQ ID NO: 18:
```

(i) SEQUENCE CHARACTERISTICS:
        (A) LENGTH: 33 amino acids
        (B) TYPE: amino acid
        (C) STRANDEDNESS: single
        (D) TOPOLOGY: linear (xi) SEQUENCE DESCRIPTION: SEQ ID NO: 18:

Tyr Thr Thr Thr Leu Ala Asp Val Arg Phe Ser Thr Tyr Leu Ile Leu
1               5                   10                  15

Asp Phe Tyr Tyr Cys Gln His Phe Trp Ser Thr Pro Arg Thr Phe Thr
            20                  25                  30

Leu (2) INFORMATION FOR SEQ ID NO: 19:

(i) SEQUENCE CHARACTERISTICS:
        (A) LENGTH: 24 amino acids
        (B) TYPE: amino acid
        (C) STRANDEDNESS: single
        (D) TOPOLOGY: linear (xi) SEQUENCE DESCRIPTION: SEQ ID NO: 19:

Val Leu Glu Val Leu Leu Cys Ala Phe Asp Phe Lys Tyr Trp Met Ser
1               5                   10                  15

Trp Val Arg Gln Leu Glu Trp Ile
            20

(2) INFORMATION FOR SEQ ID NO: 20:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO: 20:

Val Leu Glu Val Leu Leu Cys Thr Phe Thr Phe Asp Phe Tyr Met Glu
1               5                   10                  15

Trp Val Arg Gln Arg Leu Glu Trp Ile Ala
            20                  25

(2) INFORMATION FOR SEQ ID NO: 21:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO: 21:

Val Leu Glu Pro Val Leu Leu Cys Val Asp Ile Thr Ser Asp Tyr Trp
1               5                   10                  15

Ser Trp Ile Arg Lys Asn Leu Glu Tyr Met
            20                  25

(2) INFORMATION FOR SEQ ID NO: 22:

(i) SEQUENCE CHARACTERISTICS:
        (A) LENGTH: 24 amino acids
        (B) TYPE: amino acid
        (C) STRANDEDNESS: single
        (D) TOPOLOGY: linear (xi) SEQUENCE DESCRIPTION: SEQ ID NO: 22:

```
Leu Gln Met Val Ile Cys Ala Tyr Thr Phe Asp Tyr Trp Ile Glu Trp
1               5                   10                  15

Val Lys Gln Arg Leu Glu Trp Ile
            20
```

(2) INFORMATION FOR SEQ ID NO: 23:

(i) SEQUENCE CHARACTERISTICS:
        (A) LENGTH: 25 amino acids
        (B) TYPE: amino acid
        (C) STRANDEDNESS: single
        (D) TOPOLOGY: linear (xi) SEQUENCE DESCRIPTION: SEQ ID NO: 23:

```
Val Leu Glu Val Val Met Cys Ala Tyr Thr Phe Thr Ser Tyr Gly Val
1               5                   10                  15

Asn Trp Val Lys Gln Gln Glu Trp Ile
            20                  25
```

(2) INFORMATION FOR SEQ ID NO: 24:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO: 24:

```
Leu Glu Val Met Leu Cys Ala Phe Thr Phe Ser Asp Tyr Trp Met Asn
1               5                   10                  15

Trp Val Arg Gln Ser Leu Glu Trp Val Ala
            20                  25
```

(2) INFORMATION FOR SEQ ID NO: 25:

(i) SEQUENCE CHARACTERISTICS:
        (A) LENGTH: 25 amino acids
        (B) TYPE: amino acid
        (C) STRANDEDNESS: single
        (D) TOPOLOGY: linear (xi) SEQUENCE DESCRIPTION: SEQ ID NO: 25:

```
Glu Val Leu Gln Val Val Met Cys Ala Tyr Thr Phe Ser Asn Gly Ile
1               5                   10                  15

Asn Trp Val Lys Gln Leu Glu Trp Ile
            20                  25
```

(2) INFORMATION FOR SEQ ID NO: 26:

(i) SEQUENCE CHARACTERISTICS:
        (A) LENGTH: 25 amino acids
        (B) TYPE: amino acid
        (C) STRANDEDNESS: single
        (D) TOPOLOGY: linear (xi) SEQUENCE DESCRIPTION: SEQ ID NO: 26:

```
Val Leu Glu Val Leu Leu Cys Ala Phe Thr Phe Arg Cys Ala Met Ser
1               5                   10                  15

Trp Val Arg Gln Lys Leu Trp Val Ala
            20                  25
```

(2) INFORMATION FOR SEQ ID NO: 27:

(i) SEQUENCE CHARACTERISTICS:
        (A) LENGTH: 23 amino acids

```
        (B) TYPE: amino acid
        (C) STRANDEDNESS: single
        (D) TOPOLOGY: linear (xi) SEQUENCE DESCRIPTION: SEQ ID NO: 27:

Val Leu Glu Val Leu Ile Cys Val Phe Leu Gly Tyr Gly Val Asn Trp
1               5                   10                  15

Val Arg Gln Leu Glu Trp Leu
            20

(2) INFORMATION FOR SEQ ID NO: 28:

(i) SEQUENCE CHARACTERISTICS:
        (A) LENGTH: 33 amino acids
        (B) TYPE: amino acid
        (C) STRANDEDNESS: single
        (D) TOPOLOGY: linear (xi) SEQUENCE DESCRIPTION: SEQ ID NO: 28:

Glu Ile His Pro Asp Ser Gly Thr Ile Asn Tyr Thr Pro Ser Leu Lys
1               5                   10                  15

Asp Lys Phe Ile Arg Asn Leu Leu Met Val Asp Ala Tyr Tyr Cys Ala
            20                  25                  30

Arg (2) INFORMATION FOR SEQ ID NO: 29:

(i) SEQUENCE CHARACTERISTICS:
        (A) LENGTH: 36 amino acids
        (B) TYPE: amino acid
        (C) STRANDEDNESS: single
        (D) TOPOLOGY: linear (xi) SEQUENCE DESCRIPTION: SEQ ID NO: 29:

Ala Ser Arg Asn Lys Gly Asn Lys Tyr Thr Thr Glu Tyr Ser Ala Ser
1               5                   10                  15

Val Lys Gly Arg Phe Ile Val Arg Thr Leu Leu Met Leu Asp Ala Tyr
            20                  25                  30

Tyr Cys Ala Arg
        35

(2) INFORMATION FOR SEQ ID NO: 30:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO: 30:

Tyr Val Ser Tyr Ser Gly Ser Thr Tyr Tyr Asn Pro Ser Leu Lys Ser
1               5                   10                  15

Arg Ile Ile Arg Tyr Leu Leu Val Asp Ala Tyr Tyr Cys Asn
            20                  25                  30

(2) INFORMATION FOR SEQ ID NO: 31:

(i) SEQUENCE CHARACTERISTICS:
        (A) LENGTH: 31 amino acids
        (B) TYPE: amino acid
        (C) STRANDEDNESS: single
        (D) TOPOLOGY: linear (xi) SEQUENCE DESCRIPTION: SEQ ID NO: 31:
```

```
Glu Ile Leu Pro Gly Ser Gly Ser Thr Asn Tyr His Glu Arg Phe Lys
1               5                   10                  15

Gly Lys Ala Phe Ala Ala Met Leu Leu Asp Tyr Tyr Cys Leu His
                20                  25                  30
```

(2) INFORMATION FOR SEQ ID NO: 32:

(i) SEQUENCE CHARACTERISTICS:
        (A) LENGTH: 31 amino acids
        (B) TYPE: amino acid
        (C) STRANDEDNESS: single
        (D) TOPOLOGY: linear (xi) SEQUENCE DESCRIPTION: SEQ ID NO: 32:

```
Tyr Ile Asn Pro Gly Lys Gly Tyr Leu Ser Tyr Asn Glu Lys Phe Lys
1               5                   10                  15

Gly Thr Thr Leu Val Ala Met Leu Leu Asp Ala Tyr Phe Cys Arg
                20                  25                  30
```

(2) INFORMATION FOR SEQ ID NO: 33:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO: 33:

```
Gln Ile Arg Asn Lys Pro Tyr Asn Tyr Glu Thr Tyr Tyr Ser Asp Ser
1               5                   10                  15

Val Lys Gly Arg Phe Thr Ile Arg Asp Ser Val Leu Met Leu Asp Tyr
                20                  25                  30

Tyr Cys Thr
        35
```

(2) INFORMATION FOR SEQ ID NO: 34:

(i) SEQUENCE CHARACTERISTICS:
        (A) LENGTH: 31 amino acids
        (B) TYPE: amino acid
        (C) STRANDEDNESS: single
        (D) TOPOLOGY: linear (xi) SEQUENCE DESCRIPTION: SEQ ID NO: 34:

```
Tyr Asn Asn Pro Gly Asn Gly Tyr Ile Ala Tyr Asn Glu Lys Phe Lys
1               5                   10                  15

Gly Thr Leu Val Ala Met Leu Leu Asp Ala Tyr Phe Cys Ala Arg
                20                  25                  30
```

(2) INFORMATION FOR SEQ ID NO: 35:

(i) SEQUENCE CHARACTERISTICS:
        (A) LENGTH: 32 amino acids
        (B) TYPE: amino acid
        (C) STRANDEDNESS: single
        (D) TOPOLOGY: linear (xi) SEQUENCE DESCRIPTION: SEQ ID NO: 35:

```
Gly Ile Ser Ser Gly Gly Ser Tyr Thr Phe Tyr Pro Asp Thr Val Lys
1               5                   10                  15

Gly Arg Phe Ile Arg Leu Leu Met Leu Asp Ala Tyr Tyr Cys Thr Arg
                20                  25                  30
```

(2) INFORMATION FOR SEQ ID NO: 36:

(i) SEQUENCE CHARACTERISTICS:
        (A) LENGTH: 31 amino acids
        (B) TYPE: amino acid
        (C) STRANDEDNESS: single
        (D) TOPOLOGY: linear (xi) SEQUENCE DESCRIPTION: SEQ ID NO: 36:

Met Ile Trp Gly Asp Gly Asn Thr Asp Tyr Asn Ser Ala Leu Lys Ser
1               5                   10                  15

Arg Leu Ile Lys Val Leu Met Leu Asp Ala Tyr Tyr Cys Ala Arg
            20                  25                  30

(2) INFORMATION FOR SEQ ID NO: 37:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO: 37:

Leu His Tyr Tyr Gly Tyr Asn Ala Tyr Trp Gln Thr Val Val
1               5                   10

(2) INFORMATION FOR SEQ ID NO: 38:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO: 38:

Asn Tyr Tyr Gly Ser Thr Trp Tyr Phe Asp Val Trp Thr Val Val
1               5                   10                  15

(2) INFORMATION FOR SEQ ID NO: 39:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO: 39:

Trp Asp Gly Asp Tyr Trp Val Val
1               5

(2) INFORMATION FOR SEQ ID NO: 40:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO: 40:

Gly Asn Tyr Asp Phe Asp Gly Trp Thr Leu Val
1               5                   10

(2) INFORMATION FOR SEQ ID NO: 41:

(i) SEQUENCE CHARACTERISTICS:
        (A) LENGTH: 19 amino acids
        (B) TYPE: amino acid
        (C) STRANDEDNESS: single
        (D) TOPOLOGY: linear (xi) SEQUENCE DESCRIPTION: SEQ ID NO: 41:

Ser Phe Tyr Gly Gly Ser Asp Leu Ala Val Tyr Tyr Phe Asp Ser Trp
1               5                   10                  15

Thr Leu Val (2) INFORMATION FOR SEQ ID NO: 42:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO: 42:

Ser Tyr Tyr Gly Met Asp Tyr Trp Thr Val Val
1               5                   10

(2) INFORMATION FOR SEQ ID NO: 43:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO: 43:

Ser Glu Tyr Tyr Gly Gly Ser Tyr Lys Phe Asp Tyr Trp Thr Leu Val
1               5                   10                  15

(2) INFORMATION FOR SEQ ID NO: 44:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO: 44:

Tyr Ser Ser Asp Pro Phe Tyr Phe Asp Tyr Trp Thr Leu Val
1               5                   10

(2) INFORMATION FOR SEQ ID NO: 45:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO: 45:

Glu Arg Asp Tyr Arg Leu Asp Tyr Trp Thr Leu Val
1               5                   10

(2) INFORMATION FOR SEQ ID NO: 46:

(i) SEQUENCE CHARACTERISTICS:
        (A) LENGTH: 409 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..408

(xi) SEQUENCE DESCRIPTION: SEQ ID NO: 46:

```
ATG AAA TGC AGC TGG GTC ATT CTC TTC CTC CTG TCA GGA ACT GCA GGT        48
Met Lys Cys Ser Trp Val Ile Leu Phe Leu Leu Ser Gly Thr Ala Gly
 1               5                  10                  15

GTC CAC TCT GAG GTC CAG CTG CAA CAG TCT GGA CCT GAG CTG GTG AAG        96
Val His Ser Glu Val Gln Leu Gln Gln Ser Gly Pro Glu Leu Val Lys
             20                  25                  30

CCT GGA GCT TCA ATG AAG ATA TCC TGC GAG GCT TCT GGT TAC TCA TTC       144
Pro Gly Ala Ser Met Lys Ile Ser Cys Glu Ala Ser Gly Tyr Ser Phe
         35                  40                  45

ACT GGC TAT ACC ATG CAC TGG GTG AAG CAG AGC CAT GGA ATG AAC CTT       192
Thr Gly Tyr Thr Met His Trp Val Lys Gln Ser His Gly Met Asn Leu
     50                  55                  60

GAG TGG ATT GGA CTT ATT AAT CCT TAC AAT GGT GGT ACT GTC TAC AAC       240
Glu Trp Ile Gly Leu Ile Asn Pro Tyr Asn Gly Gly Thr Val Tyr Asn
 65                  70                  75                  80

CAG AAG TTC CAG GAC AAG GCC ACA TTA ACT GTA GAC AAG TCA TCC GGC       288
Gln Lys Phe Gln Asp Lys Ala Thr Leu Thr Val Asp Lys Ser Ser Gly
                 85                  90                  95

ACA GCC TAC ATG GAG CTC CTC AGT CTG ACA TCT GAG GAC TCT GCA GTC       336
Thr Ala Tyr Met Glu Leu Leu Ser Leu Thr Ser Glu Asp Ser Ala Val
             100                 105                 110

TAT TTC TGT GCA AGA CGT TGG AGA TAT ACT ATG GAC TAT TGG GGT CAA       384
Tyr Phe Cys Ala Arg Arg Trp Arg Tyr Thr Met Asp Tyr Trp Gly Gln
         115                 120                 125

GGA ACC TCA GTC ACC GTC TCC TCA G                                     409
Gly Thr Ser Val Thr Val Ser Ser
     130                 135

(2) INFORMATION FOR SEQ ID NO: 47:

(i) SEQUENCE CHARACTERISTICS:
        (A) LENGTH: 136 amino acids
        (B) TYPE: amino acid
        (D) TOPOLOGY: linear (ii) MOLECULE TYPE: protein (xi) SEQUENCE DESCRIPTION: SEQ ID NO: 47:

Met Lys Cys Ser Trp Val Ile Leu Phe Leu Leu Ser Gly Thr Ala Gly
 1               5                  10                  15

Val His Ser Glu Val Gln Leu Gln Gln Ser Gly Pro Glu Leu Val Lys
             20                  25                  30

Pro Gly Ala Ser Met Lys Ile Ser Cys Glu Ala Ser Gly Tyr Ser Phe
         35                  40                  45

Thr Gly Tyr Thr Met His Trp Val Lys Gln Ser His Gly Met Asn Leu
     50                  55                  60

Glu Trp Ile Gly Leu Ile Asn Pro Tyr Asn Gly Gly Thr Val Tyr Asn
 65                  70                  75                  80

Gln Lys Phe Gln Asp Lys Ala Thr Leu Thr Val Asp Lys Ser Ser Gly
                 85                  90                  95

Thr Ala Tyr Met Glu Leu Leu Ser Leu Thr Ser Glu Asp Ser Ala Val
             100                 105                 110

Tyr Phe Cys Ala Arg Arg Trp Arg Tyr Thr Met Asp Tyr Trp Gly Gln
         115                 120                 125

Gly Thr Ser Val Thr Val Ser Ser
     130                 135

(2) INFORMATION FOR SEQ ID NO: 48:

(i) SEQUENCE CHARACTERISTICS:
```

(A) LENGTH: 382 base pairs
(B) TYPE: nucleic acid
(C) STRANDEDNESS: single
(D) TOPOLOGY: linear (ix) FEATURE:
(A) NAME/KEY: CDS
(B) LOCATION: 1..381

(xi) SEQUENCE DESCRIPTION: SEQ ID NO: 48:

```
ATG GAG TTC CAG ACC CAG GTC TTT GTA TTC GTG TTT CTC TGG TTG TCT        48
Met Glu Phe Gln Thr Gln Val Phe Val Phe Val Phe Leu Trp Leu Ser
        140                 145                 150

GGT GTT GAC GGA GAC ATT GTG ATG ACC CAG TCT CAC AAA TTC ATG TCC        96
Gly Val Asp Gly Asp Ile Val Met Thr Gln Ser His Lys Phe Met Ser
            155                 160                 165

ACA TCA GAG GGA GAC TGG GTC AGC ATC ACC TGC AAG GCC AGT CAG GAT       144
Thr Ser Glu Gly Asp Trp Val Ser Ile Thr Cys Lys Ala Ser Gln Asp
        170                 175                 180

GTG AGT ATT GGT GTA GCC TGG TAT CAA CAG AAA CCA GGA CAA TCT CCT       192
Val Ser Ile Gly Val Ala Trp Tyr Gln Gln Lys Pro Gly Gln Ser Pro
185                 190                 195                 200

AAA CTG CTG ATT TAC TCG GCA TCC TCC CGG TAC ACT GGA GTC CCT GAT       240
Lys Leu Leu Ile Tyr Ser Ala Ser Ser Arg Tyr Thr Gly Val Pro Asp
            205                 210                 215

CGC TTC AGT GGC AGT GGA TCT GGG ACG GAT TTC ACT TTC ACC ATC AGC       288
Arg Phe Ser Gly Ser Gly Ser Gly Thr Asp Phe Thr Phe Thr Ile Ser
        220                 225                 230

AGT GTG CAG GCT GAA GAC CTG GCA GTT TAT TAC TGT CAG CAA CAT TAT       336
Ser Val Gln Ala Glu Asp Leu Ala Val Tyr Tyr Cys Gln Gln His Tyr
            235                 240                 245

ACT TCT CCA TTC ACG TTC GGC TCG GGG ACA AAC TTG GAA ATA AAA           381
Thr Ser Pro Phe Thr Phe Gly Ser Gly Thr Asn Leu Glu Ile Lys
        250                 255                 260

C                                                                      382
```

(2) INFORMATION FOR SEQ ID NO: 49:

(i) SEQUENCE CHARACTERISTICS:
(A) LENGTH: 127 amino acids
(B) TYPE: amino acid
(D) TOPOLOGY: linear (ii) MOLECULE TYPE: protein (xi) SEQUENCE DESCRIPTION: SEQ ID NO: 49:

```
Met Glu Phe Gln Thr Gln Val Phe Val Phe Val Phe Leu Trp Leu Ser
 1               5                  10                  15

Gly Val Asp Gly Asp Ile Val Met Thr Gln Ser His Lys Phe Met Ser
            20                  25                  30

Thr Ser Glu Gly Asp Trp Val Ser Ile Thr Cys Lys Ala Ser Gln Asp
        35                  40                  45

Val Ser Ile Gly Val Ala Trp Tyr Gln Gln Lys Pro Gly Gln Ser Pro
    50                  55                  60

Lys Leu Leu Ile Tyr Ser Ala Ser Ser Arg Tyr Thr Gly Val Pro Asp
65                  70                  75                  80

Arg Phe Ser Gly Ser Gly Ser Gly Thr Asp Phe Thr Phe Thr Ile Ser
            85                  90                  95

Ser Val Gln Ala Glu Asp Leu Ala Val Tyr Tyr Cys Gln Gln His Tyr
            100                 105                 110

Thr Ser Pro Phe Thr Phe Gly Ser Gly Thr Asn Leu Glu Ile Lys
```

(2) INFORMATION FOR SEQ ID NO: 50:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (xi) SEQUENCE DESCRIPTION: SEQ ID NO: 50:

GATATCCACC ATGAAATGCA GCTGGGTCAT TCTCTTCCTC CTGTCAGGAA CTGCAGGT          58

(2) INFORMATION FOR SEQ ID NO: 51:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO: 51:

GCTAGCTGAG GAGACGGTGA CCAGGGTTCC TTGACCCCAA TAGTCCATAG TATATCT           57

(2) INFORMATION FOR SEQ ID NO: 52:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (xi) SEQUENCE DESCRIPTION: SEQ ID NO: 52:

TAAGTCCAAT CCACTCAAGG TTCATTCCAG GGCTCTGCTT CACCCAGTGC ATGGTATAGC          60

CAGTGAATGA GTAACCAGAA GCCTTGCAGG AGACCTTCAC                              100

(2) INFORMATION FOR SEQ ID NO: 53:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (xi) SEQUENCE DESCRIPTION: SEQ ID NO: 53:

GATTGGACTT ATTAATCCTT ACAATGGTGG TACTGTCTAC AACCAGAAGT TCCAGGACAA          60

GGCCACATTA ACTGTAGACA AGTCAACGAG CACAGCCTAC                              100

(2) INFORMATION FOR SEQ ID NO: 54:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (xi) SEQUENCE DESCRIPTION: SEQ ID NO: 54:

CAATAGTCCA TAGTATATCT CCAACGTCTT GCACAGAAAT AGACTGCCGT GTCCTCAGAT          60

CTCAGACTGC TGAGCTCCAT GTAGGCTGTG CTCGTTGACT                              100

(2) INFORMATION FOR SEQ ID NO: 55:

(i) SEQUENCE CHARACTERISTICS:
        (A) LENGTH: 100 base pairs
        (B) TYPE: nucleic acid

```
        (C) STRANDEDNESS: single
        (D) TOPOLOGY: linear (xi) SEQUENCE DESCRIPTION: SEQ ID NO: 55:

TCCTGTCAGG AACTGCAGGT GTCCACTCTG AGGTCCAGCT GGTGCAGTCT GGAGCTGAGG    60

TGAAGAAGCC TGGAGCTTCA GTGAAGGTCT CCTGCAAGGC                         100

(2) INFORMATION FOR SEQ ID NO: 56:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 56:

GATATCCACC ATGGAGTTCC AGACCCAGGT CTTTGTATTC GTGTTTCTCT GG           52

(2) INFORMATION FOR SEQ ID NO: 57:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO: 57:

GTCGACTTAC GTTTTATTTC CACCTTTGTC CCCGAGCCGA ACGTGAATGG              50

(2) INFORMATION FOR SEQ ID NO: 58:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (xi) SEQUENCE DESCRIPTION: SEQ ID NO: 58:

TTGTATTCGT GTTTCTCTGG TTGTCTGGTG TTGACGGAGA CATTGTGATG ACCCAGTCTC    60

CAGACTCCCT GGCTGTGTCA CTGGGAGAGA GGGCCACCAT                         100

(2) INFORMATION FOR SEQ ID NO: 59:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (xi) SEQUENCE DESCRIPTION: SEQ ID NO: 59:

TCAGCAGTTT AGGAGATTGT CCTGGTTTCT GTTGATACCA GGCTACACCA ATACTCACAT    60

CCTGACTGGC CTTGCAGGTG ATGGTGGCCC TCTCTCCCAG                         100

(2) INFORMATION FOR SEQ ID NO: 60:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (xi) SEQUENCE DESCRIPTION: SEQ ID NO: 60:

ACAATCTCCT AAACTGCTGA TTTACTCGGC ATCCTCCCGG TACACTGGAG TCCCTGATCG    60

CTTCAGTGGC AGTGGATCTG GGACGGATTT CACTCTCACC                         100
```

(2) INFORMATION FOR SEQ ID NO: 61:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (xi) SEQUENCE DESCRIPTION: SEQ ID NO: 61:

```
CCCGAGCCGA ACGTGAATGG AGAAGTATAA TGTTGCTGAC AGTAATAAAC TGCCACGTCT      60

TCAGCCTGCA GACTGCTGAT GGTGAGAGTG AAATCCGTCC                           100
```

(2) INFORMATION FOR SEQ ID NO: 62:

(i) SEQUENCE CHARACTERISTICS:
        (A) LENGTH: 424 base pairs
        (B) TYPE: nucleic acid
        (C) STRANDEDNESS: single
        (D) TOPOLOGY: linear (xi) SEQUENCE DESCRIPTION: SEQ ID NO: 62:

```
GATATCCACC ATGAAATGCA GCTGGGTCAT TCTCTTCCTC CTGTCAGGAA CTGCAGGTGT      60

CCACTCTGAG GTCCAGCTGG TGCAGTCTGG AGCTGAGGTG AAGAAGCCTG GAGCTTCAGT     120

GAAGGTCTCC TGCAAGGCTT CTGGTTACTC ATTCACTGGC TATACCATGC ACTGGGTGAA     180

GCAGAGCCCT GGAATGAACC TTGAGTGGAT TGGACTTATT AATCCTTACA ATGGTGGTAC     240

TGTCTACAAC CAGAAGTTCC AGGACAAGGC CACATTAACT GTAGACAAGT CAACGAGCAC     300

AGCCTACATG GAGCTCAGCA GTCTGAGATC TGAGGACACG GCAGTCTATT TCTGTGCAAG     360

ACGTTGGAGA TATACTATGG ACTATTGGGG TCAAGGAACC CTGGTCACCG TCTCCTCAGC     420

TAGC                                                                 424
```

(2) INFORMATION FOR SEQ ID NO: 63:

(i) SEQUENCE CHARACTERISTICS:
        (A) LENGTH: 136 amino acids
        (B) TYPE: amino acid
        (C) STRANDEDNESS: single
        (D) TOPOLOGY: linear (xi) SEQUENCE DESCRIPTION: SEQ ID NO: 63:

```
Met Lys Cys Ser Trp Val Ile Leu Phe Leu Leu Ser Gly Thr Ala Gly
1               5                   10                  15

Val His Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Ser Phe
        35                  40                  45

Thr Gly Tyr Thr Met His Trp Val Lys Gln Ser Pro Gly Met Asn Leu
    50                  55                  60

Glu Trp Ile Gly Leu Ile Asn Pro Tyr Asn Gly Gly Thr Val Tyr Asn
65                  70                  75                  80

Gln Lys Phe Gln Asp Lys Ala Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Phe Cys Ala Arg Arg Trp Arg Tyr Thr Met Asp Tyr Trp Gly Gln
        115                 120                 125

Gly Thr Leu Val Thr Val Ser Ser
```

(2) INFORMATION FOR SEQ ID NO: 64:

(i) SEQUENCE CHARACTERISTICS:
        (A) LENGTH: 402 base pairs
        (B) TYPE: nucleic acid
        (C) STRANDEDNESS: single
        (D) TOPOLOGY: linear (xi) SEQUENCE DESCRIPTION: SEQ ID NO: 64:

```
GATATCCACC ATGGAGTTCC AGACCCAGGT CTTTGTATTC GTGTTTCTCT GGTTGTCTGG    60

TGTTGACGGA GACATTGTGA TGACCCAGTC TCCAGACTCC CTGGCTGTGT CACTGGGAGA   120

GAGGGCCACC ATCACCTGCA AGGCCAGTCA GGATGTGAGT ATTGGTGTAG CCTGGTATCA   180

ACAGAAACCA GGACAATCTC CTAAACTGCT GATTTACTCG GCATCCTCCC GGTACACTGG   240

AGTCCCTGAT CGCTTCAGTG GCAGTGGATC TGGGACGGAT TTCACTCTCA CCATCAGCAG   300

TCTGCAGGCT GAAGACGTGG CAGTTTATTA CTGTCAGCAA CATTATACTT CTCCATTCAC   360

GTTCGGCTCG GGGACAAAGG TGGAAATAAA ACGTAAGTCG AC                      402
```

(2) INFORMATION FOR SEQ ID NO: 65:

(i) SEQUENCE CHARACTERISTICS:
        (A) LENGTH: 127 amino acids
        (B) TYPE: amino acid
        (C) STRANDEDNESS: single
        (D) TOPOLOGY: linear (xi) SEQUENCE DESCRIPTION: SEQ ID NO: 65:

```
Met Glu Phe Gln Thr Gln Val Phe Val Phe Val Phe Leu Trp Leu Ser
1               5                   10                  15

Gly Val Asp Gly Asp Ile Val Met Thr Gln Ser Pro Asp Ser Leu Ala
            20                  25                  30

Val Ser Leu Gly Glu Arg Ala Thr Ile Thr Cys Lys Ala Ser Gln Asp
        35                  40                  45

Val Ser Ile Gly Val Ala Trp Tyr Gln Gln Lys Pro Gly Gln Ser Pro
    50                  55                  60

Lys Leu Leu Ile Tyr Ser Ala Ser Ser Arg Tyr Thr Gly Val Pro Asp
65                  70                  75                  80

Arg Phe Ser Gly Ser Gly Ser Gly Thr Asp Phe Thr Leu Thr Ile Ser
                85                  90                  95

Ser Leu Gln Ala Glu Asp Val Ala Val Tyr Tyr Cys Gln Gln His Tyr
            100                 105                 110

Thr Ser Pro Phe Thr Phe Gly Ser Gly Thr Lys Val Glu Ile Lys
        115                 120                 125
```

(2) INFORMATION FOR SEQ ID NO: 66:

(i) SEQUENCE CHARACTERISTICS:
        (A) LENGTH: 13 amino acids
        (B) TYPE: amino acid
        (C) STRANDEDNESS: single
        (D) TOPOLOGY: linear (xi) SEQUENCE DESCRIPTION: SEQ ID NO: 66:

```
Glu Gly Lys Ser Ser Gly Ser Gly Ser Glu Lys Val Asp
1               5                   10
```

(2) INFORMATION FOR SEQ ID NO: 67:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO: 67:

Gly Gly Gly Gly Ser Gly Gly Gly Gly Ser Gly Gly Gly Gly Ser
1               5                  10                  15

(2) INFORMATION FOR SEQ ID NO: 68:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO: 68:

ATGAAATGCA GCTGGGTCAT TCTCTTCCTC CTGTCAGGAA CTGCAGGTGT CCACTCT          57

(2) INFORMATION FOR SEQ ID NO: 69:

(i) SEQUENCE CHARACTERISTICS:
        (A) LENGTH: 19 amino acids
        (B) TYPE: amino acid
        (C) STRANDEDNESS: single
        (D) TOPOLOGY: linear (xi) SEQUENCE DESCRIPTION: SEQ ID NO: 69:

Met Lys Cys Ser Trp Val Ile Leu Phe Leu Leu Ser Gly Thr Ala Gly
1               5                  10                  15

Val His Ser (2) INFORMATION FOR SEQ ID NO: 70:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO: 70:

ATGGAGTTCC AGACCCAGGT CTTTGTATTC GTGTTTCTCT GGTTGTCTGG TGTTGACGGA          60

(2) INFORMATION FOR SEQ ID NO: 71:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO: 71:

Met Glu Phe Gln Thr Gln Val Phe Val Phe Val Phe Leu Trp Leu Ser
1               5                  10                  15

Gly Val Asp Gly
            20

(2) INFORMATION FOR SEQ ID NO: 72:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 72:

GTCGACTTAC GTTTTATTTC CAAGTTTGTC CCCGAGCC                          38

(2) INFORMATION FOR SEQ ID NO: 73:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO: 73:

GCTAGCTGAG GAGACGGTGA CTGAGGTTC                                   29

(2) INFORMATION FOR SEQ ID NO: 74:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO: 74:

GATATCCACC ATGGAGTTCC AGACCCAGGT CTTTGTATT                         39

(2) INFORMATION FOR SEQ ID NO: 75:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 75:

GTTAACCACC ATGAAATGCA GCTGGGTCAT TCTCTT                            36

(2) INFORMATION FOR SEQ ID NO: 76:

(i) SEQUENCE CHARACTERISTICS:
        (A) LENGTH: 117 amino acids
        (B) TYPE: amino acid
        (C) STRANDEDNESS: single
        (D) TOPOLOGY: linear (xi) SEQUENCE DESCRIPTION: SEQ ID NO: 76:

```
Glu Val Gln Leu Gln Gln Ser Gly Pro Glu Leu Val Lys Pro Gly Ala
1               5                  10                  15

Ser Met Lys Ile Ser Cys Glu Ala Ser Gly Tyr Ser Phe Thr Gly Tyr
            20                  25                  30

Thr Met His Trp Val Lys Gln Ser His Gly Met Asn Leu Glu Trp Ile
        35                  40                  45

Gly Leu Ile Asn Pro Tyr Asn Gly Gly Thr Val Tyr Asn Gln Lys Phe
    50                  55                  60

Gln Asp Lys Ala Thr Leu Thr Val Asp Lys Ser Ser Gly Thr Ala Tyr
65                  70                  75                  80

Met Glu Leu Leu Ser Leu Thr Ser Glu Asp Ser Ala Val Tyr Phe Cys
                85                  90                  95

Ala Arg Arg Trp Arg Tyr Thr Met Asp Tyr Trp Gly Gln Gly Thr Ser
            100                 105                 110

Val Thr Val Ser Ser
        115
```

(2) INFORMATION FOR SEQ ID NO: 77:

(i) SEQUENCE CHARACTERISTICS:
        (A) LENGTH: 129 amino acids
        (B) TYPE: amino acid
        (C) STRANDEDNESS: single
        (D) TOPOLOGY: linear (xi) SEQUENCE DESCRIPTION: SEQ ID NO: 77:

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Ala Ile Ser Trp Val Arg Gln Ala Pro Gly Gln Gly Leu Glu Trp Met
        35                  40                  45

Gly Trp Ile Asn Pro Tyr Gly Asn Gly Asp Thr Asn Tyr Ala Gln Lys
    50                  55                  60

Phe Gln Gly Arg Val Thr Ile Thr Ala Asp Thr Ser Thr Ser Thr Ala
65                  70                  75                  80

Tyr Met Glu Leu Ser Ser Leu Arg Ser Glu Asp Thr Ala Val Tyr Tyr
                85                  90                  95

Cys Ala Arg Ala Pro Gly Tyr Gly Ser Gly Gly Cys Tyr Arg Gly
            100                 105                 110

Asp Tyr Xaa Phe Asp Tyr Trp Gly Gln Gly Thr Leu Val Thr Val Ser
            115                 120                 125

Ser
```

(2) INFORMATION FOR SEQ ID NO: 78:

(i) SEQUENCE CHARACTERISTICS:
        (A) LENGTH: 117 amino acids
        (B) TYPE: amino acid
        (C) STRANDEDNESS: single
        (D) TOPOLOGY: linear (xi) SEQUENCE DESCRIPTION: SEQ ID NO: 78:

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Thr Gly Tyr
            20                  25                  30

Thr Met His Trp Val Lys Gln Ser Pro Gly Met Asn Leu Glu Trp Ile
        35                  40                  45

Gly Leu Ile Asn Pro Tyr Asn Gly Gly Thr Val Tyr Asn Gln Lys Phe
    50                  55                  60

Gln Asp Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Arg Trp Arg Tyr Thr Met Asp Tyr Trp Gly Gln Gly Thr Leu
            100                 105                 110

Val Thr Val Ser Ser
            115
```

(2) INFORMATION FOR SEQ ID NO: 79:

(i) SEQUENCE CHARACTERISTICS:
        (A) LENGTH: 107 amino acids
        (B) TYPE: amino acid
        (C) STRANDEDNESS: single
        (D) TOPOLOGY: linear (xi) SEQUENCE DESCRIPTION: SEQ ID NO: 79:

Asp Ile Val Met Thr Gln Ser His Lys Phe Met Ser Thr Ser Glu Gly
1               5                   10                  15

Asp Trp Val Ser Ile Thr Cys Lys Ala Ser Gln Asp Val Ser Ile Gly
                20                  25                  30

Val Ala Trp Tyr Gln Gln Lys Pro Gly Gln Ser Pro Lys Leu Leu Ile
            35                  40                  45

Tyr Ser Ala Ser Ser Arg Tyr Thr Gly Val Pro Asp Arg Phe Ser Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Ser Pro Phe
                85                  90                  95

Thr Phe Gly Ser Gly Thr Asn Leu Glu Ile Lys
            100                 105

(2) INFORMATION FOR SEQ ID NO: 80:

(i) SEQUENCE CHARACTERISTICS:
        (A) LENGTH: 113 amino acids
        (B) TYPE: amino acid
        (C) STRANDEDNESS: single
        (D) TOPOLOGY: linear (xi) SEQUENCE DESCRIPTION: SEQ ID NO: 80:

Asp Ile Val Met Thr Gln Ser Pro Asp Ser Leu Ala Val Ser Leu Gly
1               5                   10                  15

Glu Arg Ala Thr Ile Asn Cys Lys Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Xaa Thr Phe Gly Gln Gly Thr Lys Val Glu Ile
            100                 105                 110

Lys (2) INFORMATION FOR SEQ ID NO: 81:

(i) SEQUENCE CHARACTERISTICS:
        (A) LENGTH: 107 amino acids
        (B) TYPE: amino acid
        (C) STRANDEDNESS: single
        (D) TOPOLOGY: linear (xi) SEQUENCE DESCRIPTION: SEQ ID NO: 81:

Asp Ile Val Met Thr Gln Ser Pro Asp Ser Leu Ala Val Ser Leu Gly
1               5                   10                  15

Glu Arg Ala Thr Ile Thr Cys Lys Ala Ser Gln Asp Val Ser Ile Gly
                20                  25                  30

Val Ala Trp Tyr Gln Gln Lys Pro Gly Gln Ser Pro Lys Leu Leu Ile
            35                  40                  45

Tyr Ser Ala Ser Ser Arg Tyr Thr Gly Val Pro Asp Arg Phe Ser Gly

-continued

```
                50                      55                      60
Ser Gly Ser Gly Thr Asp Phe Thr Leu Thr Ile Ser Ser Leu Gln Ala
65                   70                   75                   80

Glu Asp Val Ala Val Tyr Tyr Cys Gln Gln His Tyr Thr Ser Pro Phe
                85                   90                   95

Thr Phe Gly Ser Gly Thr Lys Val Glu Ile Lys
            100                 105
```

RECOMBINANT PEPTIDES DERIVED FROM THE MC3 ANTI-BA46 ANTIBODY, METHODS OF USE THEREOF, AND METHODS OF HUMANIZING ANTIBODY PEPTIDES

CROSS REFERENCE TO RELATED APPLICATIONS

This application is a continuation of U.S. patent application Ser. No. 09/956,206 filed Sep. 17, 2001, now abandoned which is a continuation of U.S. patent application Ser. No. 08/525,539 filed Sep. 14, 1995, now U.S. Pat. No. 6,309,636, which is a 371 application of PCT/US95/11683 filed Sep. 14, 1995, which is a continuation-in-part of U.S. patent application Ser. No. 08/307,868 filed Sep. 16, 1994 which is now abandoned, and is a continuation-in-part of U.S. patent application Ser. No. 08/487,598 filed Jun. 7, 1995, which is now abandoned, the disclosures of which are all herein incorporated by reference in their entirety.

TECHNICAL FIELD

This invention relates to the diagnosis and therapy of neoplastic tumors, particularly human breast carcinomas, as well as the field of protein engineering particularly the humanization of antibodies.

BACKGROUND

The human milk fat globule (HMFG) can be used as a source of antigenic material for the preparation of both polyclonal and monoclonal antibodies for use in the diagnosis and treatment of breast cancer, as well as in the study of the breast epithelial cell surface and the processing of its antigenic components.

The milk fat globule membrane is derived from the apical surface of the mammary epithelial cell during lactation (Patton, S. et al. (1975) *Biochim Biophys Acta* 415: 273-309). As a result, the HMFG, has been a source for isolation of breast membrane glycoproteins (Taylor, P. J., et al. (1981) *Int J Cancer* 28: 17-21). Using the HMFG membrane as an immunogen, polyclonal antisera were prepared that proved to have specificity for breast epithelial cells after absorption with non-breast tissue. These polyclonal antisera specifically bound three glycoproteins of molecular weights of 150, 70, and 46 kDa, respectively (Ceriani, R. L., et al. (1977) *Proc Natl Acad Sci USA* 74: 582-6).

Monoclonal antibodies against the HMFG have been used in the identification of a novel component of the breast epithelial cell surface, a large molecular weight mucin-like glycoprotein, that was named non-penetrating glycoprotein or NPGP (Peterson, J. A., et al. (1990) *Hybridoma* 9: 221-35; and Ceriani, R. L., et al. (1983) *Somatic Cell Genet* 9: 415-27). This molecule has been used as a target in breast cancer radioimmunotherapy (Kramer, E. L., et al. (1993) *J Nucl Med* 34: 1067-74; and Ceriani, R. L., et al. (1988) *Cancer Res* 48: 4664-72), in the development of a serum assay for breast cancer diagnosis (Ceriani, R. L., et al. (1982) *Proc Natl Acad Sci USA* 79: 54204; and Ceriani, R. L., et al. (1992) *Anal Biochem* 201: 178-84), and in breast cancer prognosis using immunohistochemistry (Ceriani, R. L., et al. (1992) *Int J Cancer* 51: 343-54). This non-penetrating glycoprotein (NPGP) appears to be extremely antigenic in mice. The vast majority of monoclonal antibodies prepared against HMFG as well as breast tumors have been found to have specificity against different epitopes of this mucin.

However, the smaller molecular weight proteins of the HMFG also appear to be important surface markers for breast epithelial cells. The 46 kDa and 70 kDa HMFG antigens are also found in the serum of breast cancer patients and thus can be used as markers for breast cancer in serum assays. In addition, the 70 kDa component has been found to co-purify with the intact NPGP complex and has been shown to be linked to NPGP by disulfide bonds.

Few monoclonal antibodies, however, have been prepared against the smaller components of the human milk fat globule system, such as the 70 kDa and 46 kDa HMFG antigens. Although, Peterson, J. A., et al. (1990) *Hybridoma* 9: 221-35 were able to generate a group of monoclonal antibodies against HMFG that did detect the 46 kDa HMFG antigen, including the Mc3 antibody. The 46 kDa component of the HMFG system, also known as BA46, has been found to be present in the serum of breast cancer patients (Salinas, F. A., et al. (1987) *Cancer Res* 47: 907-13), and an increase in circulating BA46 was found to be associated with increased tumor burden. In addition, BA46 has been a target molecule in experimental radioimmunotherapy of transplanted human breast tumors in nude mice (Ceriani, R. L. et al. (1988) *Cancer Res* 48: 4664-72).

In some breast carcinomas, there is an over-expression of the BA46 antigen (Larocca, D., et al. (1991) *Cancer Res* 51: 4994-8). Also, in human milk BA46 appears to have anti-rotavirus activity that may involve binding to rotavirus (Yolken, R. H., et al. (1992) *J Clin Invest* 90: 1984-91) and that may interfere with viral infections in newborns.

A partial cDNA sequence of BA46 has been previously reported (Larocca, D., et al. (1991) *Cancer Res* 51: 4994-8) that placed BA46 in a family of proteins possessing factors V/VIII C1/C2-like domains related to discoidin I (Johnson, J. D., et al. (1993) *Proc Natl Acad Sci USA* 90: 5677-81). BA46's closest relatives may be found among the murine MGF-E8 (Stubbs, J. D., et al. (1990) *Proc Natl Acad Sci U.S.A.* 87: 8417-21), the bovine components 15/16 (Mather, I. H., et al. (1993) *Biochem Mol Biol Int* 29: 545-54) and the guinea-pig GP55 (Mather, I. H., et al. (1993) *Biochem Mol Biol Int* 29: 545-54) proteins.

cDNA cloning and in vitro cell adhesion studies, provide evidence that BA46 is a breast epithelial cell membrane glycoprotein involved in intercellular interactions. BA46 is localized to the membrane fraction when isolated from breast carcinoma cells (Larocca, D., et al. (1991) *Cancer Res* 51: 4994-8). BA46 most likely interacts with membrane integrins via its RGD containing EGF-like domain.

Carcinomas result from the carcinogenic transformation of cells of different epithelia. Two of the most damaging characteristics of carcinomas are their uncontrolled growth and their ability to create metastases in distant sites of the host, particularly a human host. It is usually these distant metastases that cause serious consequences to the host, since frequently the primary carcinoma may usually be removed by surgery. The treatment of metastatic carcinomas, that are seldom removable, depends on irradiation therapy and systemic therapies of different natures. The systemic therapies currently include, chemotherapy, radiation, hormone therapy, immunity-boosting pharmaceutical agents and procedures, hyperthermia and systemic monoclonal antibody treatment. In the latter case the antibody proteins can be labeled with radioactive elements, immunotoxins and chemotherapeutic drugs.

Radioactively labeled monoclonal antibodies were initially used with success in lymphomas and leukemia, and recently in some carcinomas. The concept underlying the use of labeled antibodies is that the labeled antibody will specifically seek and bind to the carcinoma and the radioactive element will irradiate the tumor in situ. Since the particles discharged during radioactive decay travel some distance through the tumors it is not necessary that every carcinoma cell bind the labeled antibody. The specificity of the monoclonal antibodies permit the selective treatment of the tumor while avoiding the irradiation of non-malignant tissues. The use of systemic radiation and chemotherapeutic agents without targeting agents produce serious toxic side effects in normal, nonmalignant tissues, making, these therapies undesirable for carcinomas and the use of radiolabeled monoclonal antibodies a valid alternative.

Antibodies raised against human epitopes have been used for the diagnosis and therapy of carcinomas. Also known are methods for preparing both polyclonal and monoclonal antibodies. Examples of the latter are BrE-2, BrE-3 and KC4 (e.g., U.S. Pat. Nos. 5,077,220; 5,075,219 and 4,708,930).

SUMMARY OF THE INVENTION

The present invention provides recombinant peptides that specifically and selectively bind to the human milk fat globule (HMFG) antigen, BA46. In particular, the present invention provides recombinant variants of the Mc3 antibody, including humanized versions of Mc3. The variant Mc3 peptides are particularly useful for diagnostic, prognostic, and therapeutic applications in the field of breast cancer.

The present invention also provides methods for the humanization of antibodies such as murine monoclonal antibodies. The novel humanization methods are applied to the production of humanized Mc3 antibodies and it is shown that these humanized antibodies retain the ability to engage in high affinity binding to their cognate antigen. Such humanization enables the use of these antibodies for immunodiagnostic and immunotherapeutic applications in humans.

A number of the preferred embodiments of the present invention are enumerated below.

1. A recombinant Mc3 antibody which binds to BA46 antigen of the human milk fat globule (HMFG), said antibody comprising at least one modified variable region, said modified variable region selected from the group consisting of: (i) a modified heavy chain variable region having an amino acid sequence substantially similar to that of murine Mc3 in FIG. 12, in which at least one but fewer than about 30 of the amino acid residues of murine Mc3 have been substituted; and (ii) a modified light chain variable region having an amino acid sequence substantially similar to that of murine Mc3 in FIG. 13 in which at least one but fewer than about 30 of the amino acid residues of murine Mc3 have been substituted; and (iii) a derivative of one of said modified variable regions in which one or more residues of the variable region that are not required for binding to the antigen have been deleted or in which one of more of the residues labelled (CDR) in FIG. 12 or 13 have been modified without disrupting antigen binding. Preferably, there are between about 3 and 25 substitutions, more preferably between about 5 and 20, still more preferably between about 7 and 17. Preferably, such modifications result in the humanization of the recombinant Mc3 variable regions; more preferably the variable regions are humanized according to the buried-residue-modification technique, as described below. Residues within the CDR can also be modified (substituted, deleted, or added to) so long as these modifications do not substantially disrupt antigen binding. Preferably, all of the Mc3 variants of the present invention retain a level of avidity that is at least about 20% that of the starting antibody (i.e. the murine Mc3), more preferably at least about 40%, still more preferably at least about 60%, still more preferably at least about 80%, most preferably at least about 90%. The term "recombinant" refers to the fact that the antibodies of the present invention are not naturally occurring and are the products of recombinant techniques.

2. A recombinant murine Mc3 antibody of embodiment 1, wherein at least one of said substituted amino acids is replaced with the corresponding amino acid from the appropriate human consensus sequence of FIG. 12 or 13, for a heavy or light chain variable region, respectively. Non-consensus but commonly observed human residues can also be used, but consensus residues are the most preferred.

3. A recombinant Mc3 antibody of embodiment 1 wherein said antibody comprises a heavy chain variable region and a light chain variable region.

4. A recombinant Mc3 antibody of embodiment 3 wherein both variable regions are modified variable regions, and wherein the antibody further comprises an antibody constant region or other effector agent. Any of a variety of effector agents can be joined to the antibodies of the present invention, as described below.

5. A recombinant Mc3 antibody of embodiment 4 wherein the antibody comprises a constant region that is a human antibody constant region.

6. A recombinant Mc3 antibody of embodiment 1 wherein at least about five of the amino acid residues in one of said modified variable regions have been replaced with corresponding amino acids from the appropriate human consensus sequence of FIG. 12 or 13, for a heavy or light chain variable region, respectively.

7. A recombinant Mc3 antibody of embodiment 1 comprising a modified heavy chain variable region in which at least about half of the residues listed as humanized or humanized (BR) in FIG. 12 have been replaced with corresponding residues from the human consensus sequence of FIG. 12.

8. A recombinant Mc3 antibody of embodiment 1 comprising a modified light chain variable region in which at least about half of the residues listed as humanized or humanized (BR) in FIG. 13 have been replaced with corresponding residues from the human consensus sequence of FIG. 13.

9. A recombinant Mc3 antibody of embodiment 5 comprising a modified heavy chain variable region in which at least about 90% of the residues listed as humanized or humanized (BR) in FIG. 12 have been replaced with corresponding residues from the human consensus sequence of FIG. 12; and a modified light chain variable region in which at least about 90% of the residues listed as humanized or humanized (BR) in FIG. 13 have been replaced with corresponding residues from the human consensus sequence of FIG. 13.

10. A recombinant Mc3 antibody of embodiment 9 in which all of the residues listed as humanized or humanized (BR) have been replaced with corresponding residues from the human consensus sequences of FIG. 12 or 13, for the heavy and light chains respectively.

11. A pharmaceutical composition comprising a recombinant Mc3 antibody of embodiment 1 and a pharmaceutically acceptable carrier. Pharmaceutically acceptable carriers are well known in the art. See, e.g., Remington's Pharmaceutical Sciences, Mack Publ., Easton, Pa.

12. A nucleic acid sequence encoding a modified variable region of embodiment 1.

13. A nucleic acid sequence of embodiment 12 comprising the coding region of a modified variable region as shown in FIG. 18 or 19. Coding regions are those shown in capital letters.

14. An in vitro method of detecting the presence of an HMFG antigen or binding fragment thereof, comprising obtaining a biological sample suspected of comprising the antigen or a fragment thereof; adding a recombinant Mc3 antibody of embodiment 1 under conditions effective to form an antibody-antigen complex; and detecting the presence of said antibody-antigen complex.

15. A method of diagnosing the presence of an HMFG antigen or binding fragment thereof in a subject, comprising administering to the subject a recombinant Mc3 antibody of embodiment 1 under conditions effective to deliver it to an area of the subject's body suspected of containing an HMFG antigen or a binding fragment thereof to form an antibody-antigen complex; and detecting the presence of said antibody-antigen complex.

16. A method of delivering an agent to a target site that contains an HMFG antigen comprising binding said agent to a recombinant Mc3 antibody of embodiment 1 at a position other than the antigen binding site to create an agent-antibody complex; and introducing the agent-antibody complex to the environment of said target site under conditions suitable for binding of an antibody to its cognate antigen.

17. A method of embodiment 16, wherein the target site is within the body of a human subject and introducing the agent-antibody complex comprises administering the complex to said subject.

18. A method of humanizing a non-human antibody comprising replacing one or more framework amino acid residues in a variable region of said antibody with corresponding framework amino acids from a human variable region wherein important non-human framework residues, as defined by the buried-residue-modification technique, are retained in their original form. The buried-residue-modification technique is described below.

19. A method of humanizing a non-human antibody comprising replacing one or more framework amino acid residues in a variable region of said antibody with corresponding framework amino acids from a human variable region consensus sequence wherein important non-human framework residues, as defined by the buried-residue-modification technique, are retained in their original form.

20. A method of embodiment 19 wherein both the heavy and the light chain variable regions of said antibody are humanized. Such modified variable regions are preferably joined to corresponding constant regions derived from a human antibody. Other effector agents may also be joined as described below.

BRIEF DESCRIPTION OF THE DRAWINGS

FIG. 1 illustrates Fab structures for which coordinates are available in the Protein Data Bank.

FIGS. 2 and 3 illustrate $V_L$ and $V_H$ framework residues, respectively, that contact CDR residues in Fabs of known three-dimensional structure.

FIG. 4 illustrates framework residues that contact framework residues in the opposite domain in Fabs of known three-dimensional structure.

FIGS. 5 and 6 illustrate buried framework residues in the $V_L$ and $V_H$ regions, respectively, of Fabs of known three-dimensional structure.

FIG. 7 illustrates human antibodies that are most similar in sequence to murine antibodies of known three-dimensional structure.

FIGS. 8 and 9 illustrate framework residues in $V_L$ and $V_H$, respectively, that probably need to be preserved in order to reproduce the ligand-binding properties of the original antibody.

FIGS. 10 and 11 illustrate the nucleotide sequences and corresponding amino acid sequences of the $V_H$ and $V_L$ regions, respectively, of Mc3 and their respective leader peptides. Nucleotides and amino acids are shown as the standard one letter codes. Lower case amino acids represent the leader peptides. Lower case nucleotides represent primer sequence overlaps and may, therefore, not correspond to the natural sequences.

FIGS. 12 and 13 illustrate the humanization protocol (buried-residue-modification technique) used to modify the $V_H$ and $V_L$ regions, respectively, of the Mc3 antibody.

FIGS. 14 and 15 illustrate the amino acid sequences of the $V_H$ and $V_L$ regions of the Mc3 antibody, respectively, humanized according to the buried-residue-retention technique.

FIGS. 16 and 17 illustrate primers used in the construction of genes encoding humanized Mc3 antibody (HuMc3).

FIGS. 18 and 19 illustrate the nucleotide and derived protein sequences of the $V_H$ and $V_L$ regions, respectively, of HuMc3v2.

FIG. 23 illustrates the results of biodistribution studies in mice bearing the MX-1 tumor, in which MuMc3 and HuMc3 was radiolabeled with $^{111}$In using the chelator MXDTPA.

DETAILED DESCRIPTION OF THE INVENTION

Figure 20:
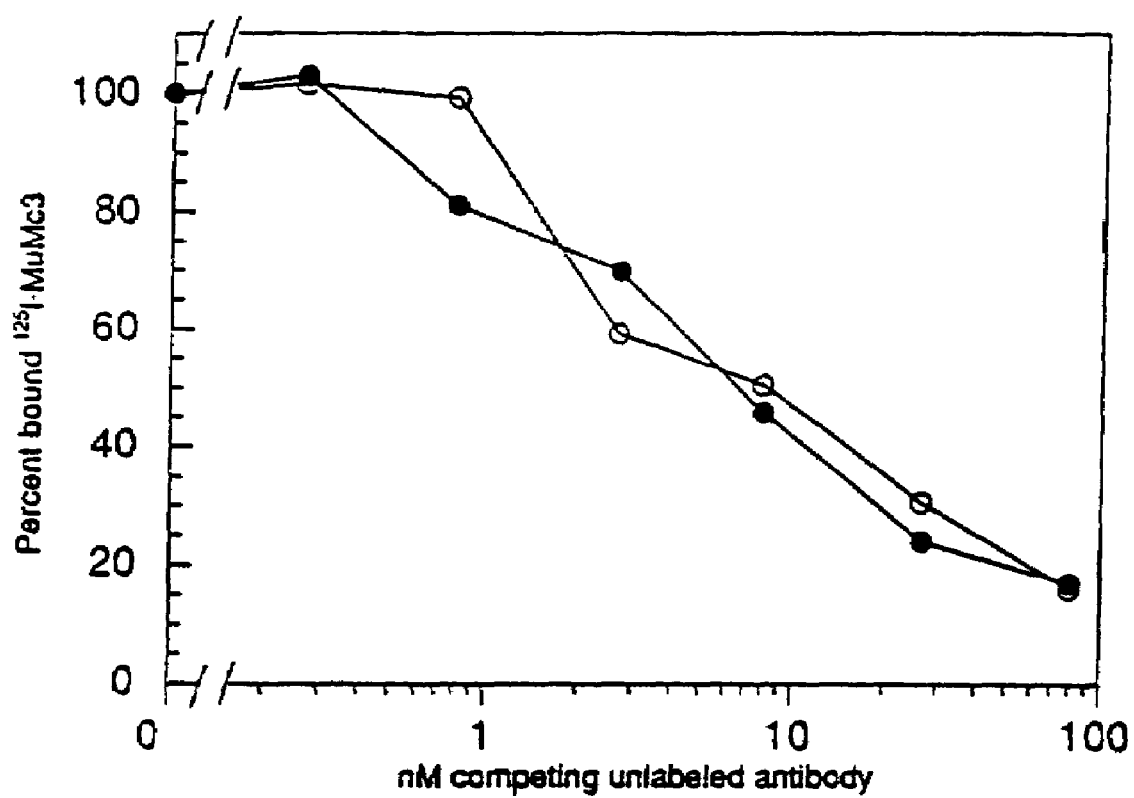
FIG. 20 illustrates the results of a competition assay between MuMc3 (wild-type murine Mc3 antibody) or HuMc3 (humanized Mc3 antibody) and $^{125}$I-MuMc3.

The Mc3 antibody offers considerable promise for use in the immunodetection and immunotherapy of breast cancer. It is known that Mc3 binds to the BA46 antigen in the human milk fat globule. See R. Ceriani et al., Proc. Natl. Acad. Sci. 79:5420-5424 (1982); R. Ceriani et al., Somatic Cell Genetics 9:415427 (1983); R. Ceriani and E. Blank, Cancer Res. 48:4664-4672 (1988); and J. Peterson et al., Hybridoma 9:221-235 (1990). See also International Publication WO92/07939, published May 14, 1992, by Ceriani & Peterson (describing the BA-46 antigen).

Recombinant variants of the Mc3 monoclonal antibody would be especially useful in order to provide a variety of Mc3-related immunodiagnostic and immunotherapeutic agents. A particularly desirable class of such variants are "humanized" Mc3 derivatives that retain the ability to interact with HMFG antigen BA-46 with high specificity and avidity; but exhibit reduced immunogenicity in humans. However, without knowing the amino acid sequences of the Mc3 antibody chains (in particular the variable regions thereof) and without having DNA sequences available, it is not feasible to develop such variants.

As described below, the present inventors have cloned and sequenced the critical regions of the Mc3 antibody, and have now described and enabled a variety of Mc3 variant peptides.

In addition, as described below, the present inventors have developed a new humanization technique for preparing antibody variants in which the tendency to elicit a human anti-mouse antibody (HAMA) reaction in humans is drastically reduced or eliminated. Using Mc3 as a first illustration, the technique has resulted in the generation of an especially preferred class of humanized Mc3 variants in which particular amino acid residues in the framework region of the variable chain have been selectively humanized. It has been shown that these humanized Mc3 variants remained quite effective at binding to their cognate antigen.

Preparing Recombinant Peptides of Mc3

The present inventors selected the following strategy for the preparation and manufacture of the recombinant and hybrid peptides of this invention. The cDNAs that encode the antibody variable regions, $V_L$ and $V_H$, of the light and heavy chains respectively can be obtained by isolation of mRNA from a hybridoma cell and reverse transcription of the mRNA, amplification of the cDNA by polymerase chain reaction (PCR) and insertion of the DNA into a vector for optional sequencing, and for restriction enzyme cutting. In general, both the $V_L$ and $V_H$ variable regions are required to effectively reproduce the binding properties of an antibody. There are two closely related kinds of $V_L$ regions (depending on whether the $V_L$ is derived from the kappa or the lambda light chain) and these are further subdivided by convention into several sequence families (see Kabat et al. 1991). There are also several sequence families for $V_H$ (id.).

The variable region cDNAs can then be modified with predesigned primers used to PCR amplify them or synthesized de novo, cloned into a vector optionally carrying DNA sequences encoding, e.g., constant region(s), optionally sequenced, and then transfected into a host cell for expression of the recombinant gene product. The binding specificity characteristics of the recombinant peptides may then be determined and compared to those of the originally isolated antibodies.

Having the sequence available, one can apply any of a number of techniques to the production of variants of the Mc3 antibody that retain antigen binding but exhibit other features that make them more desirable for particular diagnostic and/or therapeutic uses. An especially preferred class of such variants described herein are humanized variants in which the variable regions of the light and/or heavy chains have been modified to make them less likely to elicit any immunogenic (HAMA) response in humans. Such variants are thus more useful for in vivo administration. While several different humanization protocols can be utilized, as described herein, we have developed a new technique for antibody humanization that is especially useful because it achieves two highly desirable but frequently conflicting goals: (i) humanizing as many residues as possible to reduce the likelihood of immunogenicity; and (ii) retaining the avidity of the original heterologous antibody.

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, Fritsch, and Maniatis, MOLECULAR CLONING: A LABORATORY MANUAL, Second Edition (1989), OLIGONUCLEOTIDE SYNTHESIS (M. J. Gait Ed., 1984), ANIMAL CELL CULTURE (R. I. Freshney, Ed., 1987), the series METHODS IN ENZYMOLOGY (Academic Press, Inc.); GENE TRANSFER VECTORS FOR MAMMALIAN CELLS (J. M. Miller and M. P. Calos Eds. 1987), HANDBOOK OF EXPERIMENTAL IMMUNOLOGY, (D. M. Weir and C. C. Blackwell, Eds.); CELLULAR AND MOLECULAR IMMUNOLOGY, (A. K. Abbas, A. H. Lichtman and J. S. Pober, 1991 and 1993); CURRENT PROTOCOLS IN MOLECULAR BIOLOGY, (F. M. Ausubel, R. Brent, R. E. Kingston, D. D. Moore, J. G. Siedman, J. A. Smith, and K. Struhl Eds. 1987 and 1993); and CURRENT PROTOCOLS IN IMMUNOLOGY (J. E. Coligan, A. M. Kruisbeek, D. H. Margulies, E. M. Shevach and W. Strober Eds. 1991).

All patents, patent applications, and publications mentioned herein, both supra and infra, are hereby incorporated herein by reference.

By way of illustrating both the potential use of the variant antibodies described herein, and the significance of expanding their utility via humanization, one can consider the use of radioimmunoconjugates of such antibodies in both diagnostic and therapeutic applications. As an example, BrE-3 antibodies (Peterson et al. (1990) *Hybridoma* 9: 221; and U.S. Pat. No. 5,075,219 by Ceriani & Peterson) are known to bind preferentially to neoplastic carcinoma tumors because the tumors express an unglycosylated form of the breast epithelial mucin that is not expressed in normal epithelial tissue. This preferential binding combined with an observed low concentration of epitope for these antibodies in the circulation of carcinoma patients, such as breast cancer patients, makes antibodies having specificity for a mucin epitope a potentially effective carcinoma radioimmunotherapy. A $^{90}$Y—BrE-3 radioimmunoconjugate proved highly effective against human breast carcinomas transplanted into nude mice. Human clinical studies showed the $^{90}$Y—BrE-3 radioimmunoconjugate to considerably reduce the size of breast tumor metastases without any immediate toxic side effects. Moreover, an $^{111}$IN—BrE-3 radioimmunoconjugate was successfully used for imaging 15 breast cancer patients, providing excellent tumor targeting in 13 out of 15 of the patients. Out of all the breast tumor metastases occurring in another study, 86% were detected by $^{111}$IN—BrE-3. Unfortunately, 2 to 3 weeks after treatment, the patients developed a strong human anti-murine antibody (HAMA) response that prevented further administration of the radioimmunoconjugate. The HAMA response, which is observed for numerous murine monoclonal antibodies, precludes any long-term administration of murine antibodies to human patients. Similarly, other heterologous antibodies, when administered to humans, elicited similar antibody responses. The anti-heterologous human response is thus a substantial factor limiting the successful use of heterologous monoclonal antibodies as therapeutic agents.

Antibody Humanization

Based on the studies described above and others, it is apparent that in many cases monoclonal antibodies can only be administered once to a subject because of the detrimental effects of eliciting an immunogenic response. This is true for most heterologous antibodies being administered to mammalian animals.

Several different attempts have been made in an effort to circumvent these problems, including the development of so-called "chimeric antibodies" and "CDR-grafted antibodies", and attempts to generate human monoclonal hybridoma lines. These efforts have met with only limited success. "Chimeric antibodies" are direct fusions between variable domains of one species and constant domains of another. Murine/human chimeric antibodies have been shown to be less immunogenic in humans than whole murine antibodies, but, nevertheless, in some cases an immune response is mounted to the murine variable region. A further reduction of the "foreign" or heterologous nature of antibodies was achieved by "grafting" only the CDRs, from a murine monoclonal antibody onto a human supporting framework (i.e. the framework region or "FR") prior to its subsequent fusion with an appropriate constant domain, (European Patent Application, Publication No. 239, 400 to Winter; Riechmann, et al.

(1988) *Nature* 332: 323-327). However, the procedures employed to accomplish CDR-grafting can yield "humanized" antibodies that are not as effective at binding to the antigen. That is, the resultant CDR-grafted antibodies have tended to lose avidity (in many cases to less than one third of the original avidity). The third type of technique, use of human monoclonal hybridoma lines have also not been generally satisfactory. In particular, human monoclonal hybridoma cell lines have not been very stable and have, therefore, not been suitable for the large scale, repeated production of monoclonal antibodies.

An improved technique for the humanization of monoclonal antibodies is described in International Publication WO94/11509, published May 26, 1994, by Couto et al. That technique, referred to herein as the "buried-residue-retention technique" or "BR-R technique", is also described below.

A further improved technique for the humanization of monoclonal antibodies is described herein. Using this novel technique, referred to as the "buried-residue-modification technique" or "BR-M technique", we have produced humanized Mc3 peptides, as described below. Surprisingly, while the buried-residue-modification technique involved the humanization of even more residues than the earlier-described BR-R technique, and is thus expected to further reduce the possibility of eliciting a HAMA response in humans, the resulting humanized Mc3 antibody variant has been shown to retain substantially all of the avidity of the original murine antibody. A description of these techniques and illustrative applications are provided below.

As a general matter, the ligand binding characteristics of an antibody combining site are determined primarily by the structure and relative disposition of the CDRs, although some neighboring residues also have been found to be involved in antigen binding (Davies, et al. (1990) *Ann. Rev. Biochem.* 59: 439-473). The humanized derivatives of non-human antibodies rely to varying degrees upon the complementary determining regions (CDRs) to provide binding affinity to the antibody's ligand, and the framework residues (FRs) which support the CDRs to dictate their disposition relative to one another. The crystallographic analysis of numerous antibody structures has revealed that the antigen/antibody binding site is composed almost entirely of the CDR residues. The necessity of the CDRs to form these structures, combined with the appreciated hypervariability of their primary sequence, leads to a great diversity in the antigen combining site.

X-ray crystallographic studies demonstrate that the framework structures of the $F_v$ of different antibodies assume a canonical structure regardless of the species of origin, amino acid sequence, or ligand specificity. This is generally taken as evidence that the ligand-binding characteristics of an antibody combining site are determined primarily by the structure and relative disposition of the CDRs, although some neighboring framework residues may also be involved in antigen-binding. Thus, if the fine specificity of an antibody is to be preserved, its CDR structures, and probably some of the neighboring residues, their interaction with each other and with the rest of the variable domains, must also be maintained. These crystallographic studies point to the possible need for retaining most, if not all, of these residues.

While at first the necessity of retaining these amino acids might seem to prevent reaching the goal of decreasing immunogenicity by "humanization", the actual number of amino acids that must be retained is usually relatively small because of the striking similarity between, for example, human and murine variable regions.

Using either the buried-residue-retention technique ("BR-R"), or the buried-residue-modification technique ("BR-M"), humanization of the variable region of a non-human antibody, e.g., a murine antibody, begins with the identification of "important" xenogeneic amino acids to be retained. In both the BR-R technique and the BR-M technique, amino acid residues that are involved in antigen binding, or that contact the CDRs and/or an opposite chain of the antibody are assigned to the category of "important" residues to be left in their original form, e.g., in murine form.

The two methods differ strikingly, however, with respect to their treatment of buried amino acid residues, i.e. those having side-chains that are not exposed on the surface of the molecule. In particular, the BR-R technique was based in part on the following two propositions: (i) buried amino acid residues might not be expected to contribute substantially to the antibody's antigenicity (e.g., the HAMA response elicited by a murine monoclonal antibody); and (ii) varying such buried residues might disrupt the underlying structure of the antibody chain, thereby decreasing or destroying the original avidity for which it was selected. Accordingly, in the BR-R technique, these buried residues are not modified from their original form. Thus, for example, applying the BR-R technique to the humanization of a murine antibody, the buried residues would be left as they were in the original murine form. Then, among the exposed residues, those residues that make up the CDRs, and those framework residues that contact the CDRs and/or the other chain, would be retained. The other exposed residues would preferably be humanized.

The BR-M method involves making the opposite decision with respect to the buried residues. That is, rather than retaining buried residues in their original form (e.g. in the murine form), they are preferably humanized by replacement with amino acids corresponding to those in a human consensus model. The BR-M method was employed herein in the production of preferred humanized antibodies derived from Mc3. Unexpectedly, this additional humanization (which should further reduce the possibility of a HAMA response in humans) did not disrupt the ability of the CDRs to bind to the cognate antigen. On the contrary, as illustrated below, humanized Mc3 antibodies produced by the BR-M method exhibited specific high avidity binding to BA-46 that was fully comparable to that of the original murine antibody.

While the buried residues have been regarded as unlikely to contribute to immunogenicity, the present inventors believe that such residues can indeed influence immunogenicity, although the manner in which they do so may be indirect. In particular, even if a residue is relatively inaccessible to solvent, it can nevertheless exert a "pushing" or "pulling" effect on nearby surface residues. In other words, while the buried residues do not contribute to the primary structure of the antibody surface, they may well affect its shape. Since that shape can in turn influence imnimunogenicity, the present inventors have undertaken the modification of buried residues in an effort to create a more "human" antibody. Using our BR-M technique, we have succeeded in achieving such humanization without sacrificing the avidity of the heterologous antibody.

The humanization of a particular residue is accomplished by modifying that residue to resemble a residue found at the corresponding location in a "human consensus model". The human consensus model is determined by comparison to a variety of human antibodies as illustrated below.

Important residues can be identified from a well characterized three-dimensional structure. However, when direct structural data are not available, it is possible using the present methodology to predict the location of important framework residues by analyzing other related antibody structures, especially those whose variable light and heavy regions belong to the same class. The classes of variable regions can be determined from their amino acid sequence.

A method by which these important amino acids are identified has been described for the case of the amino acids with buried side chains by Padlan, E. A. (Padlan, E. A., "A Possible Procedure for Reducing the Immunogenicity of Antibody Variable Domains While Preserving Their Ligand-Binding Properties", Molecular Immunology, 28:489-494 (1991)). The variable region structures of several antibodies were compared using a computer program that determines the solvent accessibility of the framework residues as well as their contacts with the opposite domain as described by Padlan, E. A. (1991), supra. Examination of such fractional solvent accessibility reveals a very close similarity in the exposure patterns of the $V_H$ and the $V_L$ domains. Put in simple terms, regardless of the particular antibody in question, and of its amino acid sequence, the buried residues occupy similar relative positions in most antibodies.

A similar analysis can be done by computer modeling, to determine which amino acids contact the CDRs and which contact the opposite domain. At this point, the Fab structures that are currently in the Protein Data bank (Bernstein, F. C., et al., J. Mol. Biol. 112:535-542 (1977)) may be examined to determine which FRs are probably important in maintaining the structure of the combining site. Thus, after a close inspection of many high resolution three-dimensional structures of variable regions, the positions of all important framework amino acids, that is, those that contact the CDRs, and the opposite domain, may be tabulated. Keeping these amino acids, as well as those from the CDRs, and finally those FR amino acids that may be involved in ligand binding, should insure to a great extent the preservation of affinity. The precise identification of FR amino acids that are involved in ligand-binding cannot be generalized since it varies for different antibodies. Nevertheless, conservative decisions can be made to preserve the amino acids located in FR that have a high probability of contacting the antigen. Many of these residues are located adjacent to the CDRs and at the N-terminus of both chains, because the surfaces of these regions tend to be contiguous with the CDR surfaces.

As described herein, it is in fact possible to retain all of these important amino acids in their original (heterologous) form, e.g. as they were in a murine monoclonal antibody, and yet produce a humanized version thereof that substantially resembles a human antibody and is thus less likely to elicit a HAMA response.

All the amino acids that are determined to be not important by either the BR-R or BR-M method can be replaced by their corresponding human counterparts, preferably selected from a human consensus sequence as illustrated below.

Designing a Preferred Framework for Use in the Humanization of an Antibody

There are at least 11 Fab structures, 2 from human and 9 from murine antibodies, for which the atomic coordinates are known and available in the Protein Data Bank. These antibodies, listed in FIG. 1, have been used to develop a "positional consensus" of important classes of framework residues, as described below.

In a first category, certain contacts between side chains in the variable domains of the 11 Fabs have been collected and presented in FIGS. 2 to 4. The numbers shown in parentheses after each residue correspond to the number of atomic contacts in which the residue is involved. Only contacts involving side chain atoms are presented; and atoms are designated as being in contact if they are within the sum of their van der Waals radii (Case and Karplus, J. Mol. Biol. 132:343-368, 1979) plus 0.5 angstroms. The numbering scheme throughout is that of Kabat et al. ("Sequences of Proteins of Immunological Interest", 5th Ed. US Dept. of Health and Human Service, NIH Publication No. 91-3242 (1991)).

FIG. 2 illustrates framework residues in the $V_L$ domains that are believed to contact CDRs. Framework residues in the $V_H$ domains that are believed to contact CDRs are listed in FIG. 3. Framework residues that are believed to contact the opposite chain (which presumably maintain the quaternary structure of the variable domains) are listed in FIG. 4.

In a second category, inward pointing and buried residues are examined. An inward-pointing residue is designated as buried if at least 50% of its side chain is inaccessible to solvent. Solvent accessibilities can be computed using the program of M. L. Connolly (J. Appl. Crystallogr. 16, 548-558) and routines developed by S. Sheriff et al. (Proc. Natl. Acad. Sci. USA 82:1104-1107), as described by Padlan (Proteins: Struct. Funct. Genet. 7:112-124, 1990); residue exposure is defined in the context of an isolated domain. The buried residues in the $V_L$ domains, i.e., those which are located in the domain interior, are listed in FIG. 5. The buried residues in the $V_H$ domain are listed in FIG. 6.

A "conservative" positional consensus (which we typically utilize) would regard a position as important even if only one or a few of the antibodies examined had important residues at that position. By way of illustration, it can be seen in FIG. 6 that many of the positions of buried residues in $V_H$ regions were conserved across most or all of the antibodies sampled. However, position 9 was occupied by a buried residue in only one case (a proline residue in antibody HyHEL-10). Under a somewhat less conservative approach, one could exclude such positions that were only rarely occupied by an important residue.

The positional consensus sequence of important residues will vary depending on whether the buried residues are regarded as "important" or not (i.e. whether one is using the BR-R technique or BR-M technique).

Applying this methodology, one obtains the following conservative positional consensus for humanization of a $V_L$ region using the BR-R technique:

1-7, 11, 13, 19, 21-23, 35-38, 4349, 58, 60-62, 66, 67, 69-71, 73, 75, 78, 82-88, 98, 100, 102, 104 and 106.

A corresponding BR-R positional consensus for a $V_H$ region is as follows:

1, 2, 4, 6, 9, 12, 18, 20, 22, 24, 27-30, 36-40, 43-49, 66-69, 71, 73, 76, 78, 80, 82, 82c, 86, 88, 90-94, 103, 105, 107, 109 and 111.

For application of the BR-M technique, a conservative positional consensus for a $V_L$ region is as follows:

1-5, 7, 22, 23, 35, 36, 38, 43-46, 48, 49, 58, 60, 62, 66, 67, 69, 70, 71, 85, 87, 88, 98 and 100.

A corresponding BR-M positional consensus for a $V_H$ region is as follows:

1, 2, 4, 24, 27-30, 36-40, 43-49, 66-69, 71, 73, 78, 80, 82, 86, 91-94, 103 and 105.

These positional consensus sequences can be used as convenient "templates" for predicting the occurrence of an important residue in an antibody to be humanized, as illustrated below. The positional consensus sequences apply only to framework residues. (In preferred embodiments, CDR residues are always considered important and are therefore preferably retained. It is possible, however, to modify one or more of these CDR residues without substantially disrupting antigen binding.)

A search through the tables of immunoglobulin sequences (Kabat et al., "Sequences of Proteins of Immunological Interest", 5th Ed. US Dept. of Health and Human Service, NIH Publication No. 91-3242 (1991)), shows that many human variable domain sequences are already quite similar to the antibodies used for generating the positional consensus sequences. (See FIG. 7, in which the degree of sequence similarity for a number of sampled antibodies is shown in parentheses as "n/m" where "n" is the number of identities in "m" homologous positions).

In our preferred humanization method, illustrated below, we do not use any single human antibody as a framework model. Rather, we use a consensus sequence based on the framework residues most representative of a subclass of human antibodies. That is, the consensus sequence has a maximum number of amino acids in common with all human frameworks of the same subclass. This is important because the goal of humanization is to avoid an immunological response against the engineered recombinant peptide. In practice, the sequences of the xenogeneic variable chains are aligned with the consensus sequences from all variable region subclasses of the target species and then the number of differences between the consensus sequence and corresponding important residues in the xenogeneic sequence are scored. The human consensus sequence(s) that score(s) the lowest number of differences is (are) then chosen. In the humanization of the Mc3 antibody, as illustrated below, we used consensus sequences representative of the human $V_K IV$ and $V_H I$ subclasses for humanizing the light and heavy chain variable regions, respectively.

If, in a certain case, there are too many differences in the chosen framework (e.g., more than about 16), then the same alignment procedure using all tabulated human sequences may be repeated in order to find a specific human framework whose similarity with the xenogeneic sequence is maximized at the positions of the important amino acids. Thus, most preferably, the target species FR should be a consensus sequence representative of a human subclass; but next in preference would be a framework representing residues that are fairly commonly observed in human antibodies (e.g. sequences found in several antibodies even if they are not a consensus); or, absent that, the framework of any human antibody.

FIGS. 8 and 9 further illustrate that many of the important FR amino acids occur at similar positions in different antibodies, and many of these are flanking the CDRs. Among these flanking positions are most of the framework residues that are involved in contacts with the opposite domain as shown in FIG. 4, and many of those which are in contact with the CDRs as shown in FIGS. 2 and 3 above. Moreover, almost all of the framework residues that have been observed to participate in the binding to antigen (Amit, A. G., et al., Science 233:747-753 (1986); Sheriff, et al., P.N.A.S. (USA) 82:1104-1107 (1987); Padlan, E. A., et al., P.N.A.S. (USA) 86:5938-5942 (1989); Tulip, et al., Cold Spring Harbor Symp. Quant. Biol. 54:257-263 (1989); Bentley, et al., Nature (London) 348: 254-257 (1990)), are in these flanking regions.

Thus, in these preferred methods for "animalization" or "humanization", not just the CDRs are retained, but also some of the residues immediately adjacent to the CDRs. These methods provide a much better chance of retaining more of the ligand-binding properties of the original antibody and, at the same time, producing an antibody that is much less likely to elicit an immunogenic response in a heterologous species (such as a HAMA response in humans). The likelihood of retaining the antigen binding properties of the original antibody is even greater if the first few amino acids in the $NH_2$-termini of both chains are also retained, since some of them are found to be in contact with CDRs as shown in FIGS. 2 and 3.

Humanization Protocol

Designing a humanization protocol involves applying the foregoing principles on a residue-by-residue basis to an antibody to be humanized (i.e. the "xenogeneic" or "heterologous" antibody, frequently a murine antibody). The first step is to simply align the xenogeneic sequence with the human FR consensus sequence and identify all differences in framework residues. Obviously, if the human residue at a given position in the consensus is identical to the xenogeneic counterpart, then no "humanization" is required at that position.

The next step is to identify xenogeneic residues that differ from the human consensus but which are likely to be "important" residues. Using the buried-residue-retention technique (BR-R), "important" residues (i.e. those that are to be retained) include: (i) residues within a CDR; (ii) residues that are likely to contact a CDR; (iii) residues that are likely to contact the opposite antibody chain; and (iv) buried residues. Using the positional consensus sequences as templates to predict the position of important framework residues, one can readily identify a set of residues to be maintained.

Under the buried-residue-modification (or BR-M) technique, the positional consensus sequence is adjusted to reflect the removal of buried residues from the class of "important" framework residues. Suitable BR-M positional consensus sequences are described above.

We have successfully applied these methods to the humanization of a murine monoclonal antibody, Mc3, that is expected to be particularly useful in the detection and treatment of breast cancer. The methods can be readily applied to the transformation of other antibodies from a first species into a form that is likely to be less immunogenic when administered to a second species.

Once particular residues are selected for retention or modification, the actual construction of modified variable regions can be conveniently achieved using PCR amplification with primers that are custom tailored to produce the desired mutations, or by gene synthesis. In preferred embodiments, DNAs encoding the humanized variable regions (which retained certain "important" murine residues) were then joined to DNAs encoding portions of the human constant regions in a hybrid vector. After transfecting the vector into myeloma cells, the fusion polypeptides were expressed, yielding humanized versions of the Mc3 antibodies.

The humanization procedures described herein are designed to minimize potential losses in antigen binding affinity that might result from altering the antibody framework. To further minimize the likelihood of an immunological response to the humanized antibody, target human amino acid sequences were used that comprise the consensus sequences of all appropriate human variable regions. Nevertheless, neither the exemplified amino acid changes nor the exemplified human target sequences are the only choices encompassed by this invention. Thus, many other individual amino acid changes and permutations thereof can be made without substantially disrupting the avidity of the resulting antibody. These can be particularly useful in providing an expanded repertoire of antibodies, such as Mc3 derivatives, that are likely to be quite helpful in the diagnosis and treatment of breast cancer. For example, now that we have successfully sequenced the variable regions of the Mc3 antibody, a variety of recombinant Mc3 peptides can be prepared in which conservative mutations (including substitutions, deletions and additions) can be made that are calculated to be unlikely to disrupt avidity, guided by the information provided herein as well as knowledge in the art. Preferably, the variants retain a level of avidity that is at least about 20% that of the starting antibody (e.g. the murine Mc3), more preferably at least about 40%, still more preferably at least about 60%, still more preferably at least about 80%, most preferably at least about 90%.

A convenient method for predicting the suitability of potential substitutions is performed by checking to see whether a particular amino acid has been incorporated into that position in known naturally-occurring antibodies. Appearance of the amino acid in that position in known human and/or murine antibodies, especially antibodies having similar frameworks, suggests that it is not incompatible with the architecture of the variable region. Thus, although the human consensus residue is the most preferred, other preferred substitutions can be selected from residues that have been observed at corresponding positions in other antibodies, especially those that have been observed in several closely-related antibodies. An illustration of such comparisons is described, for example, in International Publication WO94/11509, published May 26, 1994, by Couto et al. (see, e.g., Tables 10 and 11).

The recombinant peptides of the present invention can be provided as non-glycosylated peptides but they are preferably used in glycosylated form. When provided in glycosylated form, the recombinant peptide may be operatively linked to a glycosyl residue(s) provided by the eukaryotic cell where it is expressed, or it may be cloned and expressed in a prokaryotic cell as the naked polypeptide and the glycosyl residue(s) added thereafter, for example by means of glycosyl transferases as is known in the art. Examples of glycosyl residue(s) that may be added to the recombinant peptide of the invention are N-glycosylated and O-glycosylated residues, among others. The glycosyl residues added to the naked recombinant peptide may have a molecular weight of about 20 to 50,000 daltons, and more preferably about 100 to 20,000 daltons or greater, depending on the size and molecular weight of the peptide to which they are attached. However, other types of polysaccharides and molecular weights may also be present. Glycosyl residues and other modifying groups can also be attached to the naked recombinant peptide of the invention by chemical means as is known in the art.

A single CDR is the smallest part of an antibody known to be capable of binding to an antigen. The sequences of the $V_L$ and $V_H$ CDRs of the Mc3 exemplary recombinant is shown below. Thus, small peptides that have the sequence of a single CDR can bind antigen and are, therefore, suitable for imaging tumors in vivo. A CDR attached to an effector agent may be synthesized chemically or recombinantly encoded in a DNA segment. Such small molecules have great tumor penetration and extremely rapid clearing properties when compared to larger antibody fragments. In some cases, it is more convenient to produce these small molecules by chemical synthesis, as is known in the art, rather than by fermentation. In many cases, these small peptides are completely non-immunogenic and an immune response, such as the HAMA response, is altogether avoided. Also preferred are 2 and 3 CDR units per chain operatively linked to one another by 1 to 10 or more amino acids and up to the entire inter-CDR segment length as positioned in the variable regions.

Heavy and light chain recombinant variable regions may be obtained individually or in $V_H/V_L$ pairs, or attached to an effector agent such as a constant region(s) or portions thereof, a drug, an enzyme, a cytokine, a toxin, a whole antibody, or any other molecule or radioisotope. The fragments of the recombinant variable regions may be synthesized chemically as is known in the art or from the DNA segments encoding the non-human variable regions. This may be attained by PCR amplification of the DNA with primers synthesized to contain the desired mutation(s) as is known in the art. Similarly, the fragments encoding recombinant variable regions may be synthesized chemically or obtained by established cloning methods of restriction digestion, ligation, mutagenesis, and the like, as is known in the art.

It is possible to combine for example a chimeric light chain with a humanized heavy chain and vice versa. Preferably, however, both the heavy and the light chains are humanized.

There are advantages to using the different molecular variants of the recombinant peptide depending on the specific applications for which they are intended, some of which are listed below.

a) Smaller molecules penetrate target tissues more efficiently and are cleared from the body much more rapidly than larger molecules.

b) Single chain molecules can be manipulated and synthesized more efficiently that multiple chain molecules.

c) Many of these variants can be synthesized efficiently and inexpensively in bacteria, including the non-glycosylated recombinants.

d) Bi-functional or multifunctional molecules may carry effector agents, such as enzymes, cytokines, toxins, radioisotopes, drugs, and other molecules, to a target tissue.

e) Having a repertoire of variants can be especially useful in diagnostic/therapeutic settings in which particular derivative-versions of a basic antibody structure can be more or less useful in a given individual or a given class of individuals, or over time of administration.

The recombinant peptides and hybrid peptides of this invention encompass CDRs and/or recombinant variable regions, antibody fragments such as Fab, Fab', F(ab')$_2$, and the like, see, e.g., O'Kennedy, R., and Roben, P. (O'Kennedy, R., and Roben, P., "Antibody Engineering: an Overview", Essays Biochem. (England) 26:59-75 (1991)). Variable regions can also be combined with constant regions, catalytic fragments, enzymes, hormones, and other molecules such as drugs and linkers, transmitters, and toxins, among others. Since the specificity and affinity of the antibody can effectively target it to a specific site containing its cognate antigen, such combinations can be especially effective tools for imaging, therapy, and diagnostics.

Single-Chain Antigen-Binding Polypeptides

A method for constructing single chain antigen-binding polypeptides has been described by Bird et al. (Bird, R. E., et al., Science 242:243-246 (1988); Bird, R. E., et al., Science 244:409 (1989)). Single Chain $F_v$ (scF$_v$ or sF$_v$) are single chain recombinant peptides containing both $V_L$ and $V_H$ with a linker such as a peptide connecting the two chains ($V_L$-linker-$V_H$). The engineering may be done at the DNA level, in which case knowledge of the sequence is required. These recombinant peptides have the conformational stability, folding, and ligand-binding affinity of single-chain variable region immunoglobulin fragments and may be expressed in E. coli. (Pantoliano, M. V., et al., Biochem. (US) 30:10117-25 (1991)). The peptide linker binding the two chains may be of variable length, for example, about 2 to 50 amino acid residues, and more preferably about 12 to 25 residues, and may be expressed in E. coli. (Pantoliano, M. V., et al. (1991), supra). A recombinant peptide such as an scF$_v$ may be expressed and prepared from E. coli and used for tumor targeting. The clearance profiles for scF$_v$ in some situations fragments are advantageous relative to those of normal antibodies, Fab, Fab' or F(ab')$_2$ fragments. (Colcher, D., et al., J. Natl. Cancer Inst. 82:1191-7 (1990)). Another type of recombinant peptide comprises a $V_H$-linker-$V_L$ and may have about 230 to 260 amino acids. A synthetic gene using E. coli codons may be used for expression in E. coli. A leader peptide of about 20 amino acids, such that of Trp LE may be used to direct protein secretion into the periplasmic space or medium. If this leader peptide is not naturally cleaved, the $sF_v$ recombinant peptide may be obtained by acid cleavage of the unique asp-pro peptide bond placed between the leader peptide and the $sF_v$-encoding region (Houston, J. S., et al., "Protein Engineering of Antibody Binding Sites: Recovery of Specific Activity in an Anti-Digoxin Single-Chain $F_v$ Recombinant Produced in *E. coli*.", PNAS (USA) 85 (16):5879-83 (1988)). The construction, binding properties, metabolism and tumor targeting of the single-chain $F_v$ recombinant peptides derived from monoclonal antibodies may be conducted as previously described (Milenic, D. E., et al., *Cancer Res.* (US) 51 (23 pt1): 6363-71 (1991); Yokota, et al., "Rapid Tumor Penetration of a single-chain $F_v$ and Comparison with Other Immunoglobulin Forms", Cancer Res. (US) 52(12):3402-8 (1992)). This type of recombinant peptide provides extremely rapid tumor penetration and even distribution throughout tumor mass compared to IgG or Ig fragments Fab and $F(ab')_2$.

Bifunctional $scF_v$-Fxn or Fxn-$scF_v$

An example of this type of recombinant peptide is a $V_L$-linker-$V_H$ with an effector agent such as a hormone, enzyme, cytokine, toxin, transmitter, and the like. These hybrid recombinant peptides may be prepared as described by McCarney et. al. (McCarney, J. E. et al., "Biosynthetic Antibody Binding Sites: Development of a Single-Chain $F_v$ Model Based on Antidinitrophenol IgA Myeloma MOPC 315", J. Protein Chem. (US) 10 (6):669-83 (1991)). A bi-functional hybrid recombinant peptide containing an $F_c$-binding fragment B of staph protein A amino terminal to a single-chain recombinant $F_v$ region of the present specificity is also encompassed and may be prepared as previously described. (Tai, M. S., et al., Biochem. 29 (35):8024-30 (1990)). In this example of a hybrid recombinant peptide of this invention is a Staph. A fragment B (anti $F_c$))-$scF_v$ polypeptide. The order is backward of normal cases. This FB-$sF_v$ may be encoded in a single synthetic gene and expressed as peptide in *E. coli*. This recombinant peptide is a good example of a useful multifunctional targetable single-chain polypeptide. A hybrid recombinant peptide also comprising antibodies to a human carcinoma receptor and angiogenin is also part of this invention. Angiogenin is a human homologue of pancreatic RNAse. This is an $F(ab')_2$-like antibody-enzyme peptide effector. Another hybrid recombinant peptide comprising a $V_H$-CH1 heavy chain-RNAse may be expressed in a cell that secretes a chimeric light chain of the same antibody. A secreted antibody of similar structure was shown to cause the inhibition of growth and of protein synthesis of K562 cells that express the human transferrin receptor (Rybak, S. M., et al., "Humanization of Immunotoxins", PNAS 89:3165-3169 (1992)).

Bi-specific Antibodies

A monoclonal antibody or antibody fragment may be incorporated into a bi-specific recombinant peptide as described, for example, by Greenman et al. (Greenman, J., et al., *Mol. Immunol.* (England) 28 (11):1243-54 (1991). In this example, a bi-specific $F(ab')_2$ was constructed, comprising two F(ab') joined by a thioether linkage. Bi-specific antibodies may also be obtained when two whole antibodies are attached. Another way to obtain bi-specific antibodies is by mixing chains from different antibodies or fragments thereof. In this manner the "left" branch of the bi-specific antibody has one function while the "right" branch has another.

Phage Display Libraries

The recombinant peptides in accordance with this invention may be screened with a filamentous phage system. This system may also be used for expressing any genes of antibodies or fragments thereof as well as for screening for mutagenized antibody variants as described by Marks et al. (Marks, J. D., et al., "Molecular Evolution of Proteins on Filamentous Phage. Mimicking the Strategy of the Immune System", J. Mol. Biol. (England) 267 (23):1607-10 (1992)). A library of $V_H$ and $V_L$ genes or recombinants thereof may be cloned and displayed on the surface of a phage. Antibody fragments binding specifically to several antigens may be isolated as reported by Marks (Marks, J. D., "By-Passing Immunization. Human Antibodies from V-gene Libraries Displayed on Phage", J. Mol. Biol. (England) 222 (3):581-97 (1991)).

Covalent Oligosaccharide Modifications

The present recombinant peptides alone or as hybrid peptides comprising antibodies and fragments thereof may be, e.g., covalently modified utilizing oxidized oligosaccharide moieties. The hybrid recombinant peptides may be modified at the oligosaccharide residue with either a peptide labeled with a radioisotope such as $^{125}I$ or with a chelate such as a diethylenetriaminepentaacetic acid chelate with $^{111}In$. The use of oligosaccharides provides a more efficient localization to a target than that obtained with antibodies radiolabeled either at the amino acid chain lysines or tyrosines (Rodwell, J. D. et al., "Site-Specific Covalent Modification of Monoclonal Antibodies: In Vitro and In Vivo Evaluations", PNAS (USA) 83:2632-6 (1986)).

Fragments derived from the variable regions can be bound by a peptide or non-peptide linker such as is known in the art. Examples of peptide linkers are polylysines, leucine zippers, EGKSSGSGSEJKVD, and (GGGGS)×3, and non-peptide polymers, among others.

Effector agents such as peptides and non-peptides may also be attached to the recombinant peptides of the invention. These include non-peptide polymers, monomers, atoms, etc., which are discussed below.

In another aspect, this invention provides a polypeptide that comprises at least recombinant peptide of the invention and at least one effector agent operatively linked to the peptide, combinations thereof and mixtures thereof. The effector agents that can utilized in this invention comprise peptides such as the constant regions of an antibody, cytokines, enzymes, toxins, non-peptide polymers, monomers, and atoms such as metals. The polypeptides of the invention encompass peptides linked by disulfide bonds, including peptide polymers produced and secreted by a cell which is expressing a peptide of the invention.

In one particularly preferred embodiment, the effector agent may comprise an atom such a radioisotope, an enzyme or a fluorescent label. These effector agents are suited for in vivo and in vitro assays because they permit the identification of complexes formed by the peptide of the invention. Radioisotopes are particularly preferred for in vivo imaging. Polypeptide labeling is known in the art (Greenwood, F. C., et al., Biochem. J. 89: 114-123 (1963)). When a glycosylated polypeptide is utilized, the radiolabel may be attached to the glycosyl residue as is known in the art (Hay, G. W. et al, in Methods in Carbohydrate Chemistry, Vol 5:357, Whistler, R. L. Ed., Academic Press, NY and London (1965)). Effector agents comprising a monomer may be therapeutic, immunogenic or diagnostic agents, radioisotopes, DNA, or RNA monomers, chemical linkers, chemical chelators, transmitter molecules, combinations thereof, or combinations thereof with peptide and non-peptide polymers or copolymers and atoms. Examples of therapeutic agents are anti-neoplastic drugs such as vincristine, intercalation drugs, adriamycin, enzymes, toxins and hormones, among others. Examples of immunogenic agents are other vaccines against tumors such as r carcinomas or for others purposes. Examples of diagnostic agents are radioisotopes and enzymes, among others. Examples of therapeutic, immunogenic and diagnostic agents are toxins, vaccines, and radioisotopes, among others. Examples of radioisotopes are $^{111}$In, $^{35}$S, $^{90}$Y, $^{186}$Re, $^{225}$Ac, $^{125}$I and $^{99m}$Tc, among others. Examples of DNA and RNA monomers are A, T, U, G, C, among others. Examples of chemical linkers are dithiobis(succinimidyl)propionate and bis-(sulfosuccinimidyl) suberate, among others. Examples of transmitter molecules are cAMP and cGMP, among others. Examples of toxins are ricin A-chain and abrin A-chain, among others.

When the effector agent is a non-peptide polymer linked to the recombinant polypeptide of the invention, it may comprise an ester, ether, vinyl, amido, imido, alkylene, arylalkylene, cyanate, urethane, or isoprene polymers, DNA polymers, RNA polymers, copolymers thereof and copolymers thereof with peptide polymers or monomers, or have labeled atoms attached thereto. Examples of these are polyesters, polyethers, polyethyleneglycols, polyvinyls, polyamido and polyimido resins, polyethylenes, polytetrafluoroethylene, poly(ethylene)terephathalate, polypropylene, silicone rubber, isoprenes and copolymers thereof, copolymers of silicone and carbonated polylactic or polyglycolic acid or collagen, and the like. Particularly preferred are biodegradable and bioresorbable or bioabsorbable materials, which if detached from the polypeptide and left in the systemic circulation will not damage endogenous tissues. The effector agent being a peptide may comprise antibodies such as IgA, IgG, IgM, IgE or IgD, the constant region of antibodies of a species different from the variable region or fragments thereof, and the CDRs, variable regions, Fab, Fab', F(ab')$_2$ fragments of antibodies of the classes described above, hormones, enzymes, peptide transmitters and whole antibodies, combinations thereof, and combinations thereof with non-peptide polymers, copolymers, monomers and atoms such as radioisotopes. Examples of peptide transmitters and hormones suitable for use herein are insulin, growth hormone, FSH, LH, endorphins, and TNF, among others. Examples of enzymes are peroxidase, LDH, alkaline phosphatase and galactosidase, among others.

The polypeptides of the present invention can be provided as an anti-tumor composition along with a carrier or diluent, preferably a pharmaceutically-acceptable carrier or diluent. The anti-tumor recombinant peptide and the hybrid polymer provided herein may be present in the composition in an amount of about 0.001 to 99.99 wt %, more preferably about 0.01 to 20 wt %, and still more preferably about 1 to 5 wt %. However, other amounts are also suitable. Carriers generally, and pharmaceutically-acceptable carriers in particular are known in the art and need not be further described herein. The carrier may be provided in a separate sterile container or in admixture with the polypeptide. Typically, saline, aqueous alcoholic solutions, albumin-saline solutions, and propylene glycol solutions are suitable. However, others may also be utilized. When utilized for therapeutic purposes the proteic material must be of a purity suitable for human administration, and the composition may contain other ingredients as is known in the art. Examples of these are other anti-neoplastic drugs such as adriamycin and mitomycin, cytoxan, PALA and/or methotrexate, among others. However, other therapeutic drugs, carriers or diluents, immunological adjuvants and the like may be also be added. When the composition described above is utilized for in vivo imaging, it may comprise about 0.001 to 99.9 wt % recombinant peptide, and more preferably about 0.01 to 25 wt % recombinant peptide. Typically, when the composition is utilized for therapeutic purposes it may contain about 0.001 to 99.9 wt % recombinant peptide, and more preferably about 0.01 to 30 wt % recombinant peptide. When utilized for the ex vivo purging of neoplastic cells from bodily fluids such as spinal fluid, the composition may comprise about 0.0001 to 50 wt %, and preferably about 0.01 to 20 wt % recombinant peptide. When applied to the in vitro diagnosis of tumors such as carcinomas the composition of the invention may comprise about 0.001 to 35 wt % recombinant peptide, and more preferably about 0.01 to 10 wt % recombinant peptide. Other amounts, however, are also suitable.

For Mc3 antibodies, in particular, such products have special utility in the treatment of tumors of the breast. "Humanized" or "partially humanized" recombinant Mc3 peptides will thus be useful for the diagnosis and treatment of breast cancers in humans. The humanized Mc3 antibodies are expected to be particularly suitable for repeated administration to a subject and for long term therapy, such as in the case of metastases and/or the reoccurrence of tumors. Of all recombinants described and encompassed herein, the ones most suitable for in vivo applications are those that exhibit low or no binding to serum antigens and to normal cells, like Mc3. Suitable for in vitro or ex vivo uses are those that exhibit good binding to tumor cell antigens such as the carcinoma cell antigen and weak or no binding to normal cells, like Mc3. Even though a patient may have in circulation an interfering amount of a molecule that can bind the recombinant peptide, the peptide may still be administered after removal of such serum molecule either by ex-vivo procedures or by administration of flush doses of the recombinant peptide, or peptide polymer of the invention.

A kit for the diagnosis of tumors such as carcinomas may comprise, for example, a composition comprising Mc3 variant polypeptides of the present invention, a solid support, immunoglobulins of a different species selectively binding the constant regions of the Mc3 variant antibody, protein G or protein A, and instructions for its use. This diagnostic kit may be utilized by covalently attaching the antigen or the recombinant peptide of the invention or a fusion protein thereof to the solid support by means of a linker as is known in the art. In a particularly preferred embodiment, the support is coated with a polypeptide such as methylated albumin as described in U.S. Pat. No. 4,572,901. When a biological sample is added to a well, the recombinant peptide or peptide polymer of the invention will bind any BA46 antigen, present in the biological sample. If a competitive assay is utilized, to the solid supported antigen or hybrid peptide thereof are added a known amount of the recombinant peptide and the sample. Thereafter, γ-globulin, protein G or protein A in labeled form may be added for detection. Monoclonal antibodies may be prepared as described by Kohler and Milstein (Kohler, G. and Milstein, C., "Continuous Culture of Fused Cell Secreting Antibody of Predefined Specificity", Nature 256:495-497 (1975)). Suitable for use in this invention are antibodies such as IgG, IgM, IgE, IgA, and IgD. Protein A, protein G and γ-globulin may be obtained commercially.

A diagnostic kit for detecting tumors such as carcinomas, and more particularly human carcinomas is provided herein that comprises an anti-BA46 composition comprising a recombinant peptide or peptide polymer and an effector agent comprising an enzyme, a radioisotope, a fluorescent label and/or a peptide comprising the constant region of an antibody of the species for which use it is intended, or fragments thereof capable of binding anti-constant region immunoglobulins, protein G or A, anti-tumor antibody, anti-constant region immunoglobulins, protein G or protein A, a solid support having operatively linked thereto an antigen which specifically binds to the anti-BA46 recombinant peptide of the invention and the antibody, and instructions for its use. When the effector agent comprises a peptide, such as the constant region of an antibody of the target species, the solid support may have operatively linked thereto an antibody which specifically binds to a portion of a fusion protein other than the antigen of the invention. This permits the binding of the anti-tumor recombinant peptide to the antigen molecule now attached to the solid support. Any complex formed between the recombinant peptide of the invention and the supported tumor antigen will, thus, remain attached to the solid substrate. A competitive assay may then be conducted by addition to the solid supported antigen of a known amount of the BA46 antigen and the sample. The amount of antigen present in the sample may be obtained from a dilution curve by addition of anti-constant region immunoglobulins, protein G, protein A or other antibody binding molecules, e.g., labeled, to bind the hybrid recombinant peptide that is now attached to the support. This kit may be used in a competitive assay where the supported antigen molecule competes with antigen in the sample for a known amount of the recombinant peptide of the invention. The assay was described by Ceriani, R. L., et al. (Ceriani, R. L., et al., Anal. Biochem. 201:178-184 (1992)), the relevant text thereof being incorporated herein by reference.

A tumor such as a carcinoma may be imaged in vivo and/or diagnosed by administering to a subject suspected of carrying a carcinoma the anti-BA46 recombinant peptide or peptide polymer of the invention in radiolabeled form, in an amount effective to reach the tumor cells and bind thereto, and detecting any localized binding of the labeled recombinant peptide or peptide polymer to the tumor. Typically, the recombinant peptide or peptide polymer of the invention may be administered in an amount of about 0.001 to 5000 mg/kg weight per treatment, more preferably about 0.01 to 5000 µg/kg weight per treatment, and more preferably about 0.1 to 500 µg/kg weight per treatment. However, other amounts may also be utilized. Radiolabels that may be utilized are $^{111}$In, $^{125}$I, $^{99m}$Tc, and $^{131}$I, among others. These radioisotopes may be detected with various radioactivity counting and imaging apparatuses known in the art, and in wide use by the medical community.

The presence of a tumor such as a carcinoma may also be diagnosed in vitro by contacting a biological sample with the anti-tumor recombinant peptide or peptide polymer of the invention to form an anti-tumor recombinant peptide-antigen complex with any tumor antigen present in the sample, and detecting any complex formed. The biological sample is typically obtained from a subject such as a human suspected of being afflicted with the tumor. Suitable biological samples are serum, blood, sputum, feces, lymph fluid, spinal fluid, lung secretions, and urine, among others, preferably blood or serum. Clearly, any source of fluid, tissue and the like may be prepared for use in this method as is known in the art.

In one preferred embodiment of the in vitro diagnostic method, the anti-carcinoma recombinant peptides or peptide polymers added to the biological sample comprises a labeled Mc3 variant polypeptide. Suitable labeling materials were described above. This method may be practiced, with the solid support containing kit described above, as a competitive assay as disclosed by Ceriani, R. L., et al. (supra).

The present recombinant peptides are also applicable to the purging of neoplastic cells, such as carcinoma cells, from biological samples, be it fluid or tissue samples. The purging of neoplastic cells from a fluid sample is part of the invention and may be practiced by contacting a biological fluid suspected of comprising neoplastic cells with the recombinant peptide of the invention, which is capable of selectively binding to an antigen of the neoplastic cells and allowing the peptide to bind to the antigen, and separating the recombinant peptide-cell complex from the remainder of the fluid.

This method may be utilized for purging unwanted cells ex vivo by extracting a biological sample from a patient, eliminating the neoplastic cells therefrom by separation of the recombinant peptide-cell complexes or by further addition of an effector such as complement or a toxin or a radioactive label that can act upon the cell and then replenishing the purged sample to the patient. This is typically suitable for use with spinal taps where spinal fluid is rid of neoplastic cells such as carcinoma cells prior to reinjection. Other fluids may also be treated in this manner.

The present recombinant peptides or peptide polymers may also be applied to the histochemical assessment of the presence of neoplastic cells such as carcinoma cells in a tissue obtained from a subject suspected of being afflicted by a carcinoma by methods that are standard in the art, like the preparation of tissue slices and fixation on a solid substrate to permit the application of the peptide and then the assessment of any binding to neoplastic cells in the sample as indicated by the formation of complexes between the recombinant peptide and antigens on or in the cells.

The growth or the size of a primary or metastasized tumor or neoplasia such as a carcinoma may be inhibited or reduced by administering to a subject in a need of the treatment an effective amount of the anti-tumor recombinant peptides or peptide polymers of the invention. Typically, the recombinant peptides or peptide polymers may be administered in an amount of about 0.001 to 2000 µg/kg body weight per dose, and more preferably about 0.01 to 500 µg/kg body weight per dose. Repeated doses may be administered as prescribed by the treating physician. However, other amounts are also suitable. Generally, the administration of the recombinant peptide or peptide polymer is conducted by infusion so that the amount of radiolabel, toxin or other effector agent present that may produce a detrimental effect may be kept under control by varying the rate of administration. Typically, the infusion of one dose may last a few hours. However, also contemplated herein is the constant infusion of a dose for therapeutic purposes that will permit the maintenance of a constant level of the hybrid polypeptide in serum.

The infusion of the recombinant peptide or peptide polymer of the invention may be conducted as follows. Intravenous (i.v.) tubing may be pretreated, e.g., with 0.9% NaCl and 5% human serum albumin and placed for intravenous administration. The prescribed dose of the recombinant peptide or peptide polymer may be infused as follows. Optionally, unlabeled recombinant peptide or peptide polymer may be infused initially. 30 minutes after completion of the unlabeled infusion, $^{111}$In-labeled and/or $^{90}$Y labeled recombinant peptide or peptide polymer may be infused. The i.v. infusion may comprise a total volume of 250 ml of 0.9% NaCl and 5% human serum albumin and be infused over a period of about 2 hours depending on any rate-dependent side effects observed. Vital signs should be taken every, e.g., 15 minutes during the infusion and every one hour post infusion until stable. A thorough cardiopulmonary physical examination may be done prior to, and at the conclusion, of the infusion. Medications including acetaminophen, diphenhydramine, epinephrine, and corticosteroids may be kept at hand for treatment of allergic reactions should they occur. The administration of the recombinant peptide or peptide polymer of the invention may be repeated as seen desirable by a practitioner.

Typically, once a first dose has been administered and imaging indicates that there could be a reduction in the size of the tumor, whether primary or metastasized, repeated treatments may be administered every about 1 to 100, and more preferably about 2 to 60 days. These repeated treatments may be continued for a period of up to about 2 years, and in some circumstances even for longer periods of time or until complete disappearance of the tumor(s). The administration of the recombinant peptides or peptide polymers of this invention is typically more useful for therapeutic purposes when a primary tumor has, for example, been excised. Thus, it is preferably, for mopping up after surgical intervention or in cases of cancerous metastases that the present method is of most use. Also provided herein is a nucleotide sequence (DNA or RNA) encoding an Mc3 variant polypeptide; and vectors comprising DNA encoding Mc3, operably linked to a suitable promoter for expression of the polypeptides. Typically, vectors capable of replication both in eukaryotic and prokaryotic cells are suitable. When the preparation of a glycosylated recombinant polypeptide is desired the vector is preferably suitable for transfection of eukaryotic host cells.

This invention also encompasses a host cell that has been transfected with the hybrid vector described above. Suitable hosts are prokaryotic and eukaryotic hosts such as bacteria, yeast, and mammalian cells such as insect cells and non-producing hybridoma cells, among others. Suitable vectors and/or plasmids for the transfection of each one of these types of hosts are known in the art and need not be further described herein. Also known in the art are methods for cloning DNA sequences into each one of these types of vectors and for transfecting the different types of host cells.

The recombinant peptide which specifically binds to any antigen, may be produced by a method that comprises cloning the recombinant polydeoxyribonucleotide of the invention into a vector to form a hybrid vector, transfecting a host cell with the hybrid vector and allowing the expression of the recombinant peptide, and isolating the polypeptide or mixtures thereof. The DNA segment encoding the recombinant polypeptide may be obtained by chemical synthesis or by site-specific modification of the sequence encoding the variable region of the xenogeneic species by PCR amplification with specifically designed primers as is known in the art. The fragment DNAs may also be prepared by PCR with primers that introduce a stop codon at a desired position as is known in the art. The method may further comprise allowing the expressed recombinant peptides to interact with one another to form double chain recombinant peptides, one or both recombinant peptide chain comprising at least one xenogeneic CDR or variable region of the light or heavy chain of the antibody or fragment thereof modified as described above. Still part of this invention is a method of producing a hybrid recombinant peptide comprising an effector peptide and a humanized region which specifically binds to the antigen, the method comprising transfecting a host cell with the hybrid vector of this invention carrying a DNA sequence encoding the humanized region and the effector peptide, allowing the expression of the recombinant peptide, and isolating the recombinant peptide or mixtures thereof. The techniques for obtaining mRNA, conducting reverse transcription and PCR amplification of DNA, chemical synthesis of primers, cloning DNA sequences into a vector, transfecting a host cell, and purifying polypeptides from a culture medium are known in the art and need not be further described herein.

As an illustration of the methods described herein, the present inventors have undertaken the cloning, sequencing, and humanization of the murine monoclonal antibody Mc3 which is likely to be particularly useful in the diagnosis and treatment of human breast cancer.

Mc3 is a murine antibody that reacts with the human milk fat globule antigen BA46. We first constructed a chimeric version of Mc3 as described in Examples 1-3 below. Next, we successfully humanized the variable regions of the Mc3 heavy and light chains using the BR-M technique as described herein.

The results described below confirmed that we could humanize Mc3 without sacrificing avidity. In particular, we detected no significant differences between the original and humanized forms of Mc3, as measured by their affinities ($3\times10^8$ vs. $6.2\times10^8$ $M^{-1}$, respectively) and by their ability to compete for antigen binding. In a mouse model for human breast cancer, single doses of radiolabeled humanized Mc3 were found to distribute to the tumor site and help prevent the growth of the tumor.

The examples presented below are provided as a further guide to the practitioner of ordinary skill in the art, and are not to be construed as limiting the invention in any way.

EXAMPLES

Example 1

Cloning of cDNAs Encoding the $V_L$ and $V_H$ Chains of the Murine Monoclonal Antibody Mc3

The cDNAs encoding the variable regions of Mc3 were cloned, using the polymerase chain reaction (PCR). The utilized PCR primers were specific for the leader peptides and for the constant regions, respectively. Thus, the variable regions were contained in the PCR products but did not overlap with the primers. The PCR primers were purchased from Novagen (Madison, Wis.). Novagen manufactures primer collections specifically for cloning cDNAs encoding variable regions of murine cDNAs. The substrate for the PCR was polyadenylated RNA isolated from Mc3 hybridomas (Ceriani, R. L., et al. (1983) *Somatic Cell Genet* 9(4): 415-27). The experimental details for cloning cDNAs encoding variable regions of antibodies, using PCR, have been previously described (Couto, J. R., et al. (1993) *Hybridoma* 12(1): 15-23; and Couto, J. R., et al. (1993) *Hybridoma* 12(4): 485-489).

In brief, the procedures utilized herein were for the reverse-transcription (RT) of RNAs encoding the variable regions and the subsequent amplification of the cDNAs by the polymerase chain reaction. The polyadenylated RNA was isolated with a FAST TRACK™) mRNA isolation kit (Invitrogen Corporation, San Diego, Calif.).

A PCR murine Ig primer set was purchased from Novagen (Madison, Wis.), and complementary DNA (cDNA) was prepared with an RNA PCR kit (Perkin Elmer-Cetus, Norwalk, Conn.).

Two different and degenerate "leader peptide" primers combined with a single degenerate "constant region" primer were utilized for each of the isolations, and in each case three independent isolations were performed. Thus, we isolated three independent cDNA clones encoding the variable region of the heavy chain ($V_H$), and another three independent clones encoding the variable region of the light chain ($V_L$). These PCR products were directly inserted into the TA cloning vector pCRII (Invitrogen). In each case both strands of the resulting inserts were sequenced. The sequences of the three $V_H$ independent isolates were all identical as were the sequences of the three independent $V_L$ isolates. The $V_H$ and $V_L$ DNA sequences and their derived protein sequences are shown in FIGS. 10 and 11, respectively.

Nucleotide Sequence of $V_H$-signal Peptide Region:

The following sequence encodes a functional signal peptide. This sequence, however, may not be the natural one since by using a PCR primer that is specific for the first part of the signal peptide, to clone the $V_H$ cDNA, we lost the original sequence information for that region. Thus, the first 26 nucleotides of the following sequence may be different in the natural gene.

```
ATG AAA TGC AGC TGG GTC ATT CTC TTC CTC CTG TCA
GGA ACT GCA GGT GTC CAC TCT
```

Derived Protein Sequence of $V_H$ Signal Peptide:

The first 9 amino acids of the following sequence may not be identical to the original ones. See note for signal peptide-encoding DNA above.

```
M K C S W V I L F L L S G T A G V H S
```

Nucleotide Sequence of $V_L$-signal Peptide:

The following sequence encodes a functional signal peptide. This sequence, however, may not be the natural one since by using a PCR primer that is specific for the first part of the signal peptide, to clone the $V_L$ cDNA, we lost the original sequence information for that region. Thus, the first 19 nucleotides of the following sequence may be different in the natural gene.

```
ATG GAG TTC CAG ACC CAG GTC TTT GTA TTC GTG TTT
CTC TGG TTG TCT GGT GTT GAC GGA
```

Protein Sequence of $V_L$ Signal Peptide:

The first 7 amino acids of the following sequence may not be identical to the original ones. See note for signal peptide-encoding DNA above.

```
M E F Q T Q V F V F V F L W L S G V D G
```

Complete Sequence of $V_H$ and $V_L$

The complete nucleotide and amino acid sequence for the variable region of the heavy chain of Mc3 is shown in FIG. 10. The complete nucleotide and amino acid sequence for the variable region of the light chain (kappa) of Mc3 is shown in FIG. 11. The identification of the sequences was done by comparing them with the databases published by Kabat et al, supra. Amino acids are shown in the one letter code. Lower case amino acids represent the leader peptides. Lower case nucleotides represent primer sequence overlaps and may, therefore, not correspond to the natural sequences.

Example 2

Construction of ChMc3 Genes, Chimeric Version of Mc3 with Human Constant Regions DNA fragments encoding the $V_H$ and $V_L$ regions as well as appropriate leader peptides were amplified, by PCR, directly from the respective pCRII clones described above, using primers that contained appropriate terminal restriction sites for insertion into expression vectors. The PCR primers used for this purpose were as follows:

Primer Name: JO65
Terminal Restriction site: SalI
Primer specificity: Kappa chain, J region
Primer direction: antisense.
Primer sequence:

```
GTCGACTTAC G TTT TAT TTC CAA GTT TGT CCC CGA GCC
```

Primer Name: JO66
Terminal Restriction site: NheI
Primer specificity: Heavy chain, J region
Primer direction: antisense.
Primer sequence:

```
GCT AGC TGA GGA GAC GGT GAC TGA GGT TC
```

Primer Name: JO67
Terminal Restriction site: EcoRV
Primer specificity: Kappa chain, signal peptide
Primer direction: sense
Primer sequence:

```
GATATC CACC ATG GAG TTC CAG ACC CAG GTC TTT GTA TT
```

Primer Name: JO68
Terminal Restriction site: HpaI
Primer specificity: Heavy chain signal peptide
Primer direction: sense
Primer sequence:

```
GTTAAC CACC ATG AAA TGC AGC TGG GTC ATT CTC TT
```

Vent DNA polymerase (New England Biolabs) was used in these PCRs because of its high fidelity. Reaction conditions were as described in the New England Biolabs catalog. The resulting $V_H$ and $V_L$-encoding PCR products were inserted first into pBLUESCRIPT II™ (Stratagene) that had been digested with EcoRV. The resulting intermediate clones were then digested with the appropriate restriction enzymes, see above, and the DNA inserts were transferred into vectors pAH4604 and pAG4622 respectively.

These vectors, which, encode either a human gamma 1 constant region or a human kappa constant region, were developed (Coloma, M. J., et al. (1992) *J Immunol Methods* 152(1): 89-104) and kindly provided by S. L. Morrison (Dept. of Microbiology and Molecular Genetics, UCLA). The inserts were again sequenced in both directions directly in the pAH4604 and pAG4622 vectors. Both vectors were derived from pSV2 (Mulligan, R. C., and Berg, P. (1980) *Science* 209:1422-1427), and contain genomic fragments encoding either the heavy or the light chain constant domains. The vectors accept cDNAs that encode the $F_v$ regions. To ligate the $F_v$ cDNAs to the vectors, restriction ends were added to the cDNAs in a set of PCR reactions, using the JO65, JO66, JO67 and JO68 primers.

The pAG4622 light chain vector contains the gene for the human K chain constant region, including the J-C intron. It encodes xanthine-guanine phosphoribosyl-transferase or gpt (Mulligan, R. C., and Berg, P. (1981) *PNAS* (USA) 78:2072-2076) as a dominant selectable marker. It accepts the murine $V_L$ cDNA between the ribosome binding site (Kozak, M. (1984) *Nucleic Acids Res.* 12:857-872), which is preceded by the $V_H$ promoter from the anti-dansyl murine monoclonal antibody 27.44 (Coloma, M. J., et al. (1992) *J Immunol Methods* 152(1): 89-104), and the J-C intron. The J-C intron contains the k chain enhancer (Potter, H., et al. (1984) *PNAS* (USA) 81:7161-7165; and Emorine, L., et al. (1983) *Nature* 304: 447449).

The pAH4604 heavy chain vector contains the gene for the heavy chain γ1 constant region, but no J-C intron. It encodes histidinol-dehydrogenase or hisD (Hartman, S. C. and Mulligan, R. C. (1988) *PNAS* (USA) 85: 8047-8051) as a dominant selectable marker. It accepts the murine $V_H$ cDNA between the dansyl promoter-ribosome binding site and the constant ~1 gene. The vector also contains an insert that encodes the heavy chain enhancer (Rabbitts, T. H., et al (1983) *Nature* 306: 806-809).

Example 3

Preparation and Characterization of Chimeric Mc3 (ChMc3) Antibodies

All the procedures utilized in this Example have been described in detail in previous publications (Couto, J. R., et al. (1993) *Hybridoma* 12(1): 15-23; and Couto, J. R., et al. (1993) *Hybridoma* 12(4): 485489). Tissue culture conditions were generally as follows: SP2/0-Ag14 cells (Shulman, M., et al. (1978), below) were cultured either in Dulbecco's modified Eagle's medium (DME): fetal bovine serum (FBS), 90:10 (v/v) or in a mixture of DME:RPMI:FBS, 45:45:10 (v/v/v) or RPMI:FBS, 90:10 (v/v). Penicillin and streptomycin were added to prevent bacterial growth. When serum-free medium was utilized, it contained an HL-1 supplement as directed by the manufacturer (Ventrex Labs., Portland, Me.). The freezing medium was 10% DMSO in bovine serum.

In brief, after sequence verification, both plasmid constructs were electroporated into SP2/0-Ag14 myeloma cells. Supernatants from stable transfectants were assayed for the presence of the chimeric antibody. The secreted chimeric antibody was first captured by plate-bound goat anti-human kappa chain polyclonal antibody, and subsequently developed with a radiolabeled secondary goat anti-human gamma chain polyclonal antibody. The chimeric antibody was also assayed for binding to a plate-bound human milk fat globule (HMFG) preparation.

Stable transfectants expressing chimeric antibody that bound to HMFG were first cloned and then cultured in serum-free protein-free medium (Sigma cat.#S2772). ChMc3 was then purified from the medium using a protein A column (BioRad). The purified antibody ran as a single wide band on 7.6% non-reducing SDSPAGE. Its migration on the gel matched that of other purified antibodies loaded on the same gel. Under reducing conditions this band resolved into two bands of approximately 53 kDa and 29 kDa respectively, and their migration matched those of other reduced antibodies loaded on the same gel.

Example 4

Determination of the Affinity of ChMc3 for HMFG

The antibody-antigen affinity constants for the murine-human chimeric (ChMc3) antibody were determined by obtaining the reciprocal value of the concentration of competing unlabeled monoclonal antibody giving 50% binding as described by Sheldon et al. (1987) *Biochem. Cell Biol.* 65: 423-428. The protocol for the assay was as follows.

Microtiter plates (Dynatech, Chantilly, Va.) were prepared with HMFG according to standard techniques (as described by Ceriani et al., in "Monoclonal Antibodies and Functional Cell Lines" (T. J. McKern et al. eds.), pp. 398-402, New York, Plenum Press, 1984). To each well was added 25 µl $^{125}$I-Mc3 in RIA buffer (10% bovine calf serum, 0.3% TRITON™ X-100, 0.05% sodium azide pH 7.4, in phosphate buffered saline), and competed with 25 µl of either unlabeled murine antibody or murine-human chimeric antibody in RIA buffer at final concentrations in the nanomolar range.

Iodinations were performed with $^{125}$I (17 Ci/mg, Nordion International Inc., Kanata, Ontario, Canada). 50 µg monoclonal antibody Mc3 was labeled (at a specific activity of ~10 mCi/mg) using the chloramine T method as described by Ceriani, R. L., and Blank, E. W. (1988) *Cancer Res.* 48: 4664-4672. When the cpm of bound radiolabeled murine Mc3 (MuMc3) antibody was plotted on the Y axis and the logarithm of the nanomolar (nM) concentration of competing unlabeled MuMc3 antibody or murine human chimeric (ChMc3) antibody was plotted on the X axis, the antibodies exhibited similar competition profiles (Figure not shown).

The affinity of the purified Chimeric antibody (ChMc3) for HMFG was determined to be $5 \times 10^8$ M$^{-1}$, which closely matches the observed affinity constant for the Mc3 murine antibody of $3 \times 10^8$ M$^{-1}$. Furthermore, we determined in competition experiments that ChMc3 competes as well as Mc3 against the binding of radiolabeled Mc3 to HMFG. Thus, both the affinity and the specificity of the original murine antibody were preserved in its chimeric counterpart. These affinity and competition results further indicate that the antibodies are authentic.

Example 5

Identification of a Human Consensus Model for Directing the Humanization of Mc3

We reasoned that the least immunogenic humanized version of Mc3 would be one in which the $V_L$ and $V_H$ sequences approximated the consensus sequences of human $V_L$ and $V_H$ subclasses, respectively. Thus, rather than choosing the $V_L$ and $V_H$ sequences of a particular antibody as targets, we chose the consensus sequences of the human $V_K$IV and $V_H$I subclasses, for $V_L$ and $V_H$ respectively (Kabat, E. A. et al. (1991). *Sequences of proteins of immunological interest*. U.S. Dept. Health and Human Services, NIH).

These human consensus variable regions are the most similar to the corresponding variable regions of Mc3. Most of the important framework residues were identical in the murine and in the human consensus frameworks, but some were not. The human consensus model for the variable region of the heavy chain of Mc3 is shown in FIG. 12 and that for the light chain variable region is shown in FIG. 13.

Positions in which the murine residue differed from the human consensus residue were then analyzed according to either the BR-R technique or the BR-M technique, to determine whether the residue should or should not be modified for humanization, as illustrated below.

Example 6

Application of the Buried-Residue-Modification (BR-M) Techniue to the Humanization of Mc3

Using the buried-residue-modification technique (or BR-M technique), "important" residues that are to be retained include: (i) residues within a CDR; (ii) residues that are likely to contact a CDR; (iii) residues that are likely to contact the opposite antibody chain. In contrast to the BR-R technique, the buried residues can be, and preferably are, humanized.

The probable sequence position of the "important" residues, was determined by applying a conservative positional consensus developed for application of the BR-M technique, as described above. The positional consensus for $V_L$ was as follows: 1-5, 7, 22, 23, 35, 36, 38, 43-46, 48, 49, 58, 60, 62, 66, 67, 69, 70, 71, 85, 87, 88, 98, and 100. For $V_H$, it was as follows: 1, 2, 4, 24, 27-30, 36-40, 43-49, 66-69, 71, 73, 78, 80, 82, 86, 91-94, 103, and 105.

The application of the BR-M method to the humanization of the Mc3 variable regions is illustrated on a residue-by-residue basis in FIG. 12 and FIG. 13, for the heavy and light chains of Mc3, respectively.

The BR-M humanization protocol can be summarized as follows (using the terms shown in FIG. 12 and FIG. 13):

Under the Heading "Murine Retained":

| | |
|---|---|
| Yes (same as human) | murine residue identical to human consensus, humanization not required |
| Yes (CDR) | murine residue differed from human consensus but residue appeared to be within CDR, murine retained |
| Yes (contact CDR) | murine residue differed from human consensus but residue likely to contact CDR, murine retained |
| Yes (interchain cont.) | murine residue differed from human consensus but residue likely to contact opposite chain, murine retained |
| No | residue did not fit any of the preceding categories and was humanized (by substituting human consensus residue) |

Under the Heading "Humanized":

| | |
|---|---|
| n/a | murine residue identical to human consensus, humanization not required |
| Humanized | humanized residues if they were not "important" murine residues (as described above) |
| Humanized (BR) | indicates that the humanized residue was likely to be a buried residue (such a residue would have been retained under the BR-R technique) |
| Not humanized | retained a murine residue that was considered "important" |

As shown in FIG. 13, the final humanized version of $V_K$ differs only at three FR positions from the corresponding $V_K$IV human consensus sequence (Kabat, E. A. et al. (1991). *Sequences of proteins of immunological interest*. U.S. Dept. Health and Human Services, NIH). The differences between the humanized heavy chain and the human consensus for $V_H$I are more numerous, 13 FR positions. Nevertheless, a considerable fraction of human antibodies belonging to this subfamily contain more differences in FR positions from their own consensus sequences than HuMc3 $V_H$ does. Thus, for example, we found certain human $V_H$I frameworks with as many as 29 differences from their own consensus sequences. The number of buried framework residues that were changed from murine to human were 7 in $V_K$ and 5 in $V_H$.

Example 7

Application of the Buried-Residue-Retention (BR-R) Technique to the Humanization of Mc3

Using the buried-residue-retention technique, all murine residues that are likely to be buried are retained.

In order to apply the BR-R technique to the humanization of Mc3, all of the residues labelled "Humanized (BR)" in FIGS. 12 and 13 would have been left in their original murine form. Other aspects of the humanization protocol would be identical.

The amino acid sequence of a BR-R humanized form of the Mc3 variable heavy region is shown in FIG. 14 (using the standard one-letter amino acid code; lower-case letters indicate leader peptide). The corresponding sequence for the Mc3 light chain is shown in FIG. 15.

Example 8

Construction of HuMc3 Genes. Humanized Versions of the Chimeric Mc3 Genes

The entire regions to be humanized were synthesized by the overlapping oligonucleotide PCR method (Ye, Q. Z. et al. (1992) *Biochem Biophys Res Commun* 186(1): 143-9). Oligonucleotides varying in size from 49 to 101 nucleotides, were synthesized on a PCR-Mate EP DNA synthesizer model 391 (Applied Biosystems, Foster City Calif.) using 40 nmole columns, cycle 1:63, with Trityl off. The oligonucleotides were not purified prior to their use and their concentrations were estimated using the formula $c=[(A_{260})/30]\mu g/\mu l$.

Primers used in the construction of HuMc3 genes are shown in FIGS. 16 and 17. PCR conditions were as follows: 150 nM each of four long (100-101'mers) internal oligonucleotides, 2 µM each of two short (49-66'mers) terminal primers, 200 µM each dNTP, 10 mM KCl, 20 mM Tris-HCl pH 8.8, 10 mM $(NH_4)_2SO_4$, 0.1% TRITON™ X-100, 6 mM $MgSO_4$. Vent DNA polymerase (New England Biolabs), 2 units per 100 µl reaction was added after File 2, below, (hot start). A GENEAMP™ PCR system 9600 (Perkin Elmer Cetus) was programmed with the following series of linked files: File 1=[(95°, 5 min), (1 min ramp to 70°), (5 min pause)]; File 2=[(96°, 5 sec) (55°, 10 sec) (72°, 30 sec)]×3; File 3=[(96°, 5 sec) (60°, 10 sec) (72°, 30 sec)]×29; File 4=[(72°, 10 minutes)]; File 5=[(5°, forever)]. File 4 was repeated at the end of the PCR, after adding extra dNTPs (to 120 µM each) and 1 unit of Vent DNA polymerase (per 100 µl reaction).

The synthetic DNA fragments were first inserted into EcoRV-digested pBLUESCRIPT II™ (Stratagene). Once the sequences of the synthetic DNA cassettes were confirmed in the small intermediate plasmids, appropriate restriction fragments were then transferred into the expression plasmids. $V_H$, encoded in an EcoRV-NheI fragment was inserted into pAH4604 and $V_K$, encoded in an EcoRV-SalI fragment was inserted into pAG4622 (Coloma, M. J. et al. (1992) *J Immunol Methods* 152(1): 89-104; Couto, J. R. et al. (1993) *Hybridoma* 12(1): 15-23; and Couto, J. R. et al. (1993). *Hybridoma* 12(4): 485-489).

The nucleotide and corresponding polypeptide sequences of the humanized $V_H$ region of HuMc3v2 are shown in FIG. 18. The nucleotide and corresponding polypeptide sequences of the humanized $V_L$ region of HuMc3v2 are shown in FIG. 19.

Example 9

Preparation of Humanized Mc3 (HuMc3) Antibody

The humanized variable regions from Example 5 (HuMc3) were cloned into the expression vectors pAG4622 and pAH4604. As described in Example 2 above, these vectors were used to express the resulting recombinant antibody. The construction and expression of the humanized antibody genes were performed as described for the chimeric antibody in Example 3 (as well as Couto, J. R. et al. (1993) *Hybridoma* 12(1): 15-23; and Couto, J. R. et al. (1993). *Hybridoma* 12(4): 485-489). The non-producer myeloma cell line SP2/0-Ag14, ATCC:CRL 1581 was transfected, and antibody-producing clones were isolated as described in Example 3 and in Couto, J. R. et al. (1993) *Hybridoma* 12(1): 15-23; and Couto, J. R. et al. (1993). *Hybridom* 12(4): 485-489. Antibody production was boosted by the standard method of adding OPTIMAB™ (Gibco catalog 680-191 OSD) to the culture medium at a concentration of 1% of each of the components A and B.

Colonies that secreted the highest levels of antibody into the supernatants were subcloned into serum-free protein-free medium. Antibody levels in the medium were measured by standard radioimmunodetection techniques (Couto J. R. et al. (1993), *Hybridoma* 12:15-23). A plate-bound goat anti-human-K capturing antibody was used with a $^{125}$I-labeled goat anti-human-K secondary antibody, and the values obtained were compared with those from a standard dilution curve obtained in parallel using an unrelated human $IgG_1\kappa$ immunoglobulin (Sigma catalog 1-3889).

Antibody was purified from the culture supernatant of Sp2/0-Ag14 transfectants by a method similar to that of Example 3: The secreted monoclonal antibodies were concentrated through an Amicon DIAFF™ YM30 ultrafiltration membrane and purified using a protein A column (Ceriani et al. (1992), Anal Biochem 201:178-184). Purity was verified by SDS-PAGE. Purified HuMc3 ran as a single wide band on 7.6% non-reducing SDS-PAGE. Under reducing conditions, two bands were observed with apparent molecular weights of approximately 53 kDa and 29 kDa.

Example 10

Functional Comparison of HuMc3 and MuMc3

The affinity of HuMc3 for HMFG was measured similar to the method described in Example 3, to confirm that it had comparable binding activity to the mouse and chimera antibodies from which it had been derived.

MuMc3, HuMc3, and a human $IgG_1\kappa$ of unrelated specificity were radiolabeled as in Example 4. Specific activities obtained were between 6 and 20 mCi/mg.

Binding studies were conducted as outlined earlier. Briefly, microliter plates were prepared using successive layers of methylated BSA (bovine serum albumin), glutaraldehyde, and a preparation of delipidated HMFG (Ceriani R. L. et al. (1977) PNAS (USA) 74:582-586). Each well was coated with 100 ng of HMFG. Competition experiments were conducted by adding to each well a standard amount of $^{125}$I-MuMc3 and an appropriate dilution of unlabeled MuMc3 or HuMc3 in RIA buffer (10% bovine calf serum, 0.3 TRITON X-100™), 0.05% sodium azide pH 7.4, in PBS). For the determination of affinity constants, each antibody was tested in competition against itself. The affinity constant was calculated as the reciprocal of the concentration of competing unlabeled monoclonal antibody that gave 50% maximal binding.

The observed affinities of the MuMc3 and HuMc3 for a preparation of human milk fat globule were respectively $3\times10^8$ $M^{-1}$ and $6\times10^8$ $M^{-1}$. These numbers confirm that the recombinant antibodies retain binding activity for HMFG, and that the humanization procedure did not substantially alter the affinity of the original antibody.

Differences in the epitopes recognized by two related antibodies can be detected when both compete for binding to their common antigen. FIG. 20 shows results obtained when radiolabeled MuMc3 was used in competition experiments against either unlabeled MuMc3 (open circles) or unlabeled HuMc3 (filled circles). Values on the Y-axis represent the amount of $^{125}$I-MuMc3 bound in the presence of competing unlabeled antibody, relative to the binding in the absence of competing antibody. The results show that MuMc3 and HuMc3 compete equally well against labeled MuMc3, indicating that they bind to identical or closely related epitopes.

Example 11

Biodistribution Studies

HMFG antigen is known to be associated with human breast cell cancers, and has been used as a target for antibody-mediated detection and therapy. As described earlier, HuMc3 was designed to be a useful targeting agent to carry pharmacological effectors, such as radioisotopes, to tumor sites. In this Example, radioiodinated HuMc3 antibody and the MuMc3 control were used in biodistribution studies in a mouse model of human breast carcinoma to confirm that the binding activity demonstrated in the microtiter plate assays was also observable in vivo.

Athymic nu/nu mice, 11 to 12 weeks old, were purchased from Simonsen (Gilroy, Calif.). They were maintained in sterilized caging and bedding, and fed irradiation-sterilized Purina mouse chow 5058 and sterilized tap water acidified to pH 2.5. The mice were kept at a temperature of 25.6° C. to 28.9° C. on a cycle of 12 h light and 12 h dark.

The transplantable human mammary tumor MX-1 was obtained from the EG&G Mason Research Institute (Worcester, Mass.) (Inoue K. et al. (1983). Chemother Pharmacol 10:182-186). The tumor was established in nu/nu mice at our facility according to standard protocols. Tumors were grown for 22 days, and experimental radioimmunotherapy was begun on mice whose mean tumor volume was approximately 100 mm$^3$. Tumor volumes were measured with a caliper, and calculated by multiplying the length×width×height of the tumor mass and dividing by 2. Tumors were ranked according to tumor volume, and the mice were grouped so that each group had approximately the same mean tumor volume.

MuMc3, HuMc3, and a human $IgG_1\kappa$ control antibody (Sigma 1-3889) were labeled with $^{131}$I as described in Examples 4 and 10, except that Na$^{131}$I was used in place of Na$^{125}$I. The specific activities were 12.15 mCi/mg, 9.0 mCi/mg, and 11.2 mCi/mg, respectively. Mice were injected with 10 μCi of labeled antibody as a single bolus. The tissues were dissected, weighed, and counted at various times after injection, and the percent of injected dose/gram of tissue was calculated, taking into account radioisotopic decay.

Figure 21:
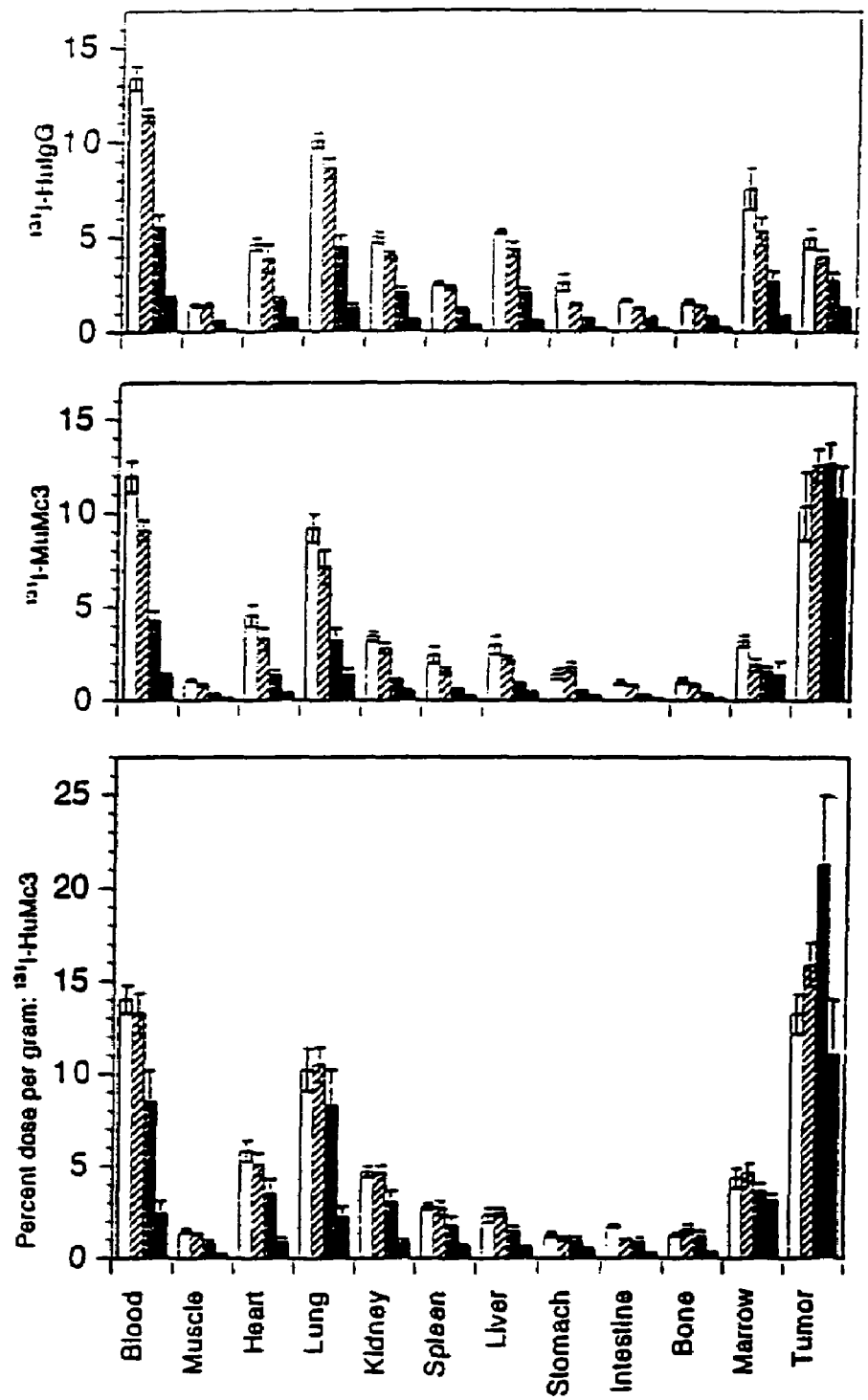
FIG. 21 illusrates the results of biodistribution studies in nude mice bearing the human MX-1 transplantable breast tumor, showing the location of $^{125}$I-labeled control IgG, MuMc3, and HuMc3 at 1, 2, 4, and 8 days after injection.

FIG. 21 shows the results of the biodistribution studies. The four bars for each tissue site show the activity present after 1, 2, 4, and 8 days, respectively (mean±standard error for 5 animals sacrificed at each time point). $^{131}$I-labeled MuMc3 and HuMc3 antibodies persisted in the tumor increased over a period of at least 4 days (middle and lower panels). In all other tissues, bound antibody decreased steadily over this period. In comparison, the amount of $^{131}$I-labeled non-specific antibody that localized to the tumor site was much smaller (upper panel).

Thus, HuMc3 showed the same tumor specificity as MuMc3. At 4 days after injection, the percent of injected HuMc3 at the tumor site was 21.3%, and at 8 days was 11.1%. Relative specific activity in the tissues was 2.5:1 (tumor:lung) and 25:1 (tumor:muscle) at 4 days. The relative specific activity was higher 8 days after injection.

Example 12

HuMc3 as a Targeting Agent for Radiotherapy of Breast Cancer

Since the HuMc3 antibody binds and homes effectively to the BA46 antigen, it is a suitable carrier to convey a therapeutic dose of radioactivity to a tumor site. This was demonstrated directly in the murine MX-1 tumor model of Example 11, using a larger dose of radioactivity.

$^{131}$I was a useful radioisotope for this purpose for two obvious reasons: it is easy to work with for experimental purposes, and it has the properties that are known to be suitable for radioimmunotherapy. In particular, it emits particles with higher energy than $^{125}$I and $^{99m}$Tc and is therefore capable of providing a greater radiation dose per mCi; furthermore, the radiation is partly in the form of beta particles, which is readily absorbed by nearby tissues. Other radioisotopes frequently used for radioimmunotherapy include $^{111}$In and $^{90}$Y.

Thus, HuMc3 antibody was radiolabeled with $^{131}$I as in Example 11, to a specific activity of 9.0 mCi/mg. MX-1 bearing nu/nu mice were prepared as before. Five MX-1 tumor-bearing athymic nu/nu mice were given a single i.p. injection of 500 µCi of $^{131}$I-HuMc3, diluted in PBS (phosphate buffered saline) containing 0.1% BSA. Tumor volumes were followed for 30 days after injection, using the caliper method outlined in the previous Example. Six mice served as a control group, and were not injected with labeled antibody.

Figure 22:
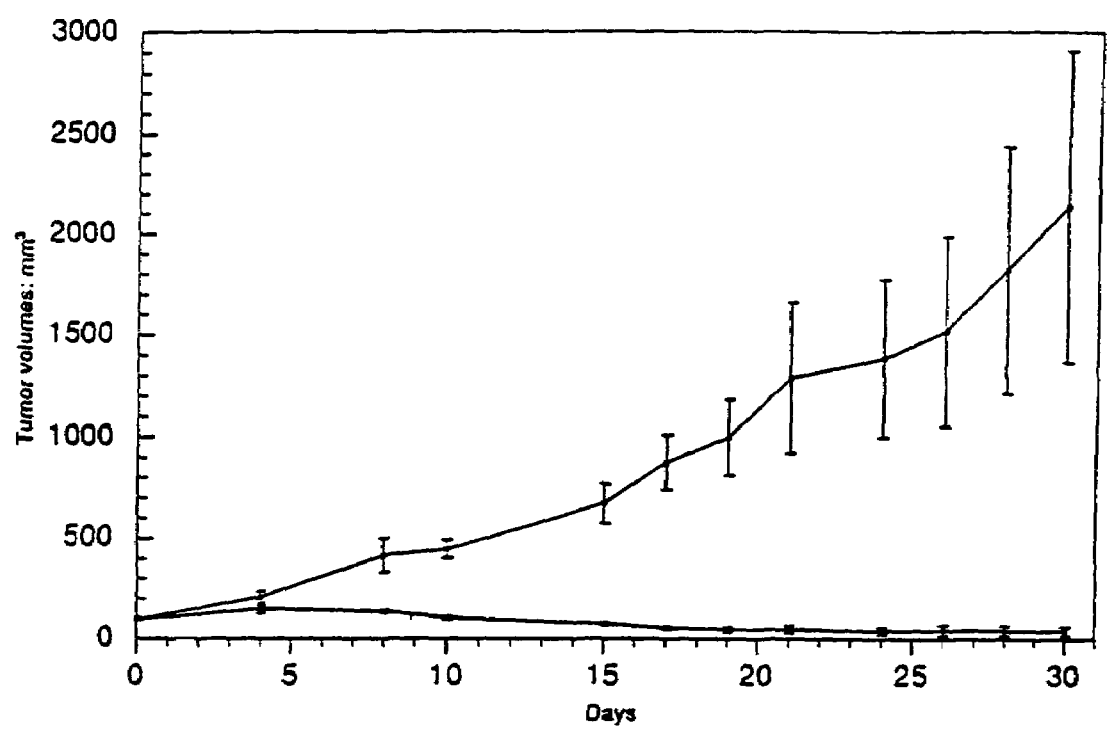
FIG. 22 illustrates the results of radioimmunotherapy studies in mice bearing the MX-1 tumor. $^{131}$I-labeled HuMc3 contained or reduced tumor mass in treated animals, while the tumor in untreated animals grew to ~20 times the original size.

As shown in FIG. 22, the initial tumor size for both treated and untreated groups was approximately 100 mm$^3$. In the treated mice, the average tumor size decreased to 42 mm$^3$ at day 30 (lower line). In contrast, tumors in the uninjected group grew continuously to reach a final average size of 2,100 mm$^3$ (upper line). No deaths occurred in either of the groups in the first 30-days after therapy. At 61 days, all five treated animals were still alive, and one animal had no detectable tumor. These results suggest that HuMc3 is more effective in experimental radioimmunotherapy than monoclonal antibodies specific for other BA46 epitopes (Peterson et al. (1994) 353:1-8 in Antigen and Antibody Molecular Engineering in Breast Cancer Diagnosis and Treatment, Plenum Press NY).

Example 13

Efficacy of HuMc3 Radiolabeled Using a Chelating Agent

Still further experiments were conducted to demonstrate the suitability of humanized Mc3 as a targeting agent for radiotherapy.

As is known to a practitioner of ordinary skill in the art, when the antibody is to be used in a clinical setting or with an isotope that has a short half life, it is generally preferable to provide the antibody pre-conjugated to a linking group, which in turn is capable of receiving the radioisotope shortly before use. Preferred examples of such linking groups are chelators. See, generally, Brechbiel, M W et al. (1991), Bioconjugate Chem 2:187-194. An example of a preferred chelator linking group is MXDTPA. The chelator can be provided in purified form and conjugated to the antibody using buffers that are essentially free of metal ions. The conjugate is generally stored in a metal-free environment to avoid occupying the binding site in the chelator. Just before use, the conjugate can be mixed with a suitable radioisotope, such as $^{111}$In or $^{90}$Y, under conditions and at a molar ratio that permit essentially all the radioisotope to be captured and retained tightly by the conjugate.

Experiments were conducted to confirm that HuMc3 could be labeled with a chelator without perturbing the binding activity for HMFG, as observed in the previous Examples.

MXDTPA was obtained from O. Gansow at the NIH, Bethesda, Md. MXDTPA was conjugated to antibody according to standard protocols (Brechbiel M W et al. (1986), Inorg. Chem. 25:2272-2281), as follows: About 3-5 mg recombinant antibody or human IgG$_1$κ control antibody were prepared by dialyzing overnight at 4° C. against 1 liter of 0.15 M NaCl and 0.05 M Hepes buffer, pH 8.6. The MXDTPA was dissolved in metal-free water in a volume of 50 µL for each 5 mg. The conjugation was carried out by combining the antibody with the MXDTPA solution, and incubating for 19 h at room temperature. Free MXDTPA was removed from the conjugated antibody by dialysis against 3 changes of ammonium acetate buffer, pH 6.8, for 24 h each.

Pharmaceutical grade $^{111}$In was obtained from Amersham, Arlington Heights, Ill. Labeling was performed by adding the $^{111}$In to the conjugated antibody as previously described (Blank E W et al. (1992) Cancer J 5:38-44). Specific activities were 6 mCi/mg and 1.7 mCi/mg for the MuMc3 and HuMc3, respectively.

The integrity of $^{111}$In-labeled antibody was determined by high-pressure liquid chromatography (HPLC). Perkin Elmer model 250 HPLC pump was used with a 600×7.5 mm TSK 250 gel filtration column. 0.1 mL samples comprising 1×10$^5$ cpm were run in a buffer of 0.15 M NaCl and 30 mM phosphate, pH 6.5 at 0.5 ml/min and a pressure of 70 bar. Fractions of 0.5 mL were collected and counted. Essentially all of the radioactivity eluted at a position corresponding to that of an IgG$_1$ standard.

Biodistribution studies were conducted using $^{111}$In labeled antibody in the MX-1 human breast tumor mouse model, as in Example 11. Each mouse received a single dose of 10 µCi (diluted in PBS containing 0.1% BSA) through the tail vein.

Results are shown in FIG. 23. Both the MuMc3 antibody (upper panel) and HuMc3 antibody (lower panel) concentrated at the tumor site, and persisted there throughout the period of the experiment. This confirms that the ability of HuMc3 to localize to the tumor site is comparable to that of the murine antibody from which it was derived, and that localization is independent of the method of labeling or the radioisotope used.

The invention claimed is:

1. A method of humanizing a non-human antibody comprising replacing one or more framework amino acid residues in a variable region of said antibody with corresponding framework amino acids from a human variable region wherein non-human framework residues, as defined by the buried-residue-modification technique, are retained in their original form, wherein the antibody comprises both:
   (i) a light chain variable region, and
   (ii) a heavy chain variable region;
   wherein said variable regions are humanized in a region that is neither contained in a CDR, nor in contact with a CDR, nor in contact with an opposing variable region of Mc3 antibody,
   with the further proviso that the humanized Mc3 heavy chain variable region has the amino acid sequence shown in SEQ ID NO: 78 and the humanized Mc3 light chain variable region has the amino acid sequence shown in SEQ ID NO: 81.

2. A method of humanizing a non-human antibody comprising replacing one or more framework amino acid residues in a variable region of said antibody with corresponding framework amino acids from a human variable region wherein non-human framework residues, as defined by the buried-residue-modification technique, are retained in their original form, wherein the resulting antibody binds to BA46 antigen of human milk fat globule (HMFG), wherein the sequence of the parent Mc3 heavy chain variable region is SEQ ID NO: 76 and the sequence of the parent Mc3 light chain variable region is SEQ ID NO: 79, said humanized antibody comprising both:
   (i) a light chain variable region, and
   (ii) a heavy chain variable region;
   wherein the humanized Mc3 heavy chain variable region has the amino acid sequence shown in SEQ ID NO: 78 and the humanized Mc3 light chain variable region has the amino acid sequence shown in SEQ ID NO: 81.

3. The method of claim 1, wherein the humanized variable chain amino acids are selected from the amino acid sequence of a single human heavy chain variable region, a single human light chain variable region, a consensus human heavy chain variable region, or a consensus human light chain variable region.

4. The method of claim 1, wherein the antibody comprises human immunoglobulin heavy and light chain constant regions.

5. The method of claim 1, wherein the antibody comprises an effector component selected from the group consisting of an enzyme, a toxin, a cytokine, a radiolabel, and a fluorescent label.

* * * * *